United States Patent
Gonye et al.

(10) Patent No.: US 6,716,582 B2
(45) Date of Patent: Apr. 6, 2004

(54) CELLULAR ARRAYS FOR THE IDENTIFICATION OF ALTERED GENE EXPRESSION

(75) Inventors: Gregory E. Gonye, Wilmington, DE (US); Michael K. Hanafey, Wilmington, DE (US); Robert A. LaRossa, West Chester, PA (US); J. Antoni Rafalski, Wilmington, DE (US); Tina K. Van Dyk, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/832,419

(22) Filed: Apr. 11, 2001

(65) Prior Publication Data

US 2003/0219736 A1 Nov. 27, 2003

Related U.S. Application Data

(60) Provisional application No. 60/197,348, filed on Apr. 14, 2000.

(51) Int. Cl.[7] .............................. C12Q 1/68; C12Q 1/02
(52) U.S. Cl. .............................................. 435/6; 435/29
(58) Field of Search ........................................ 435/6, 29

(56) References Cited

U.S. PATENT DOCUMENTS

| 5,569,588 A | 10/1996 | Ashby |
| 5,683,868 A | 11/1997 | LaRossa |
| 6,025,131 A | 2/2000 | LaRossa |

*Primary Examiner*—Terry McKelvey

(57) ABSTRACT

The present invention relates to the generation and use of a cellular array or a cellular array in combination with other genome-registered arrays (an array of arrays) for the determination of gene function and/or perturbation mode of action. Each cellular array consists of a number of microbial strains. Each strain comprises one reporter gene fusion made up of a gene or gene fragment operably linked to a reporter gene. Each gene or gene fragment has been "registered" or mapped to a specific location in the genome of the organism. The genome-registered collection of the invention may be used to determine alterations in gene expression under a variety of conditions. Such collections are amenable to rapid assay and may be used to confirm, correct or augment data generated from DNA micro array technology.

7 Claims, 19 Drawing Sheets

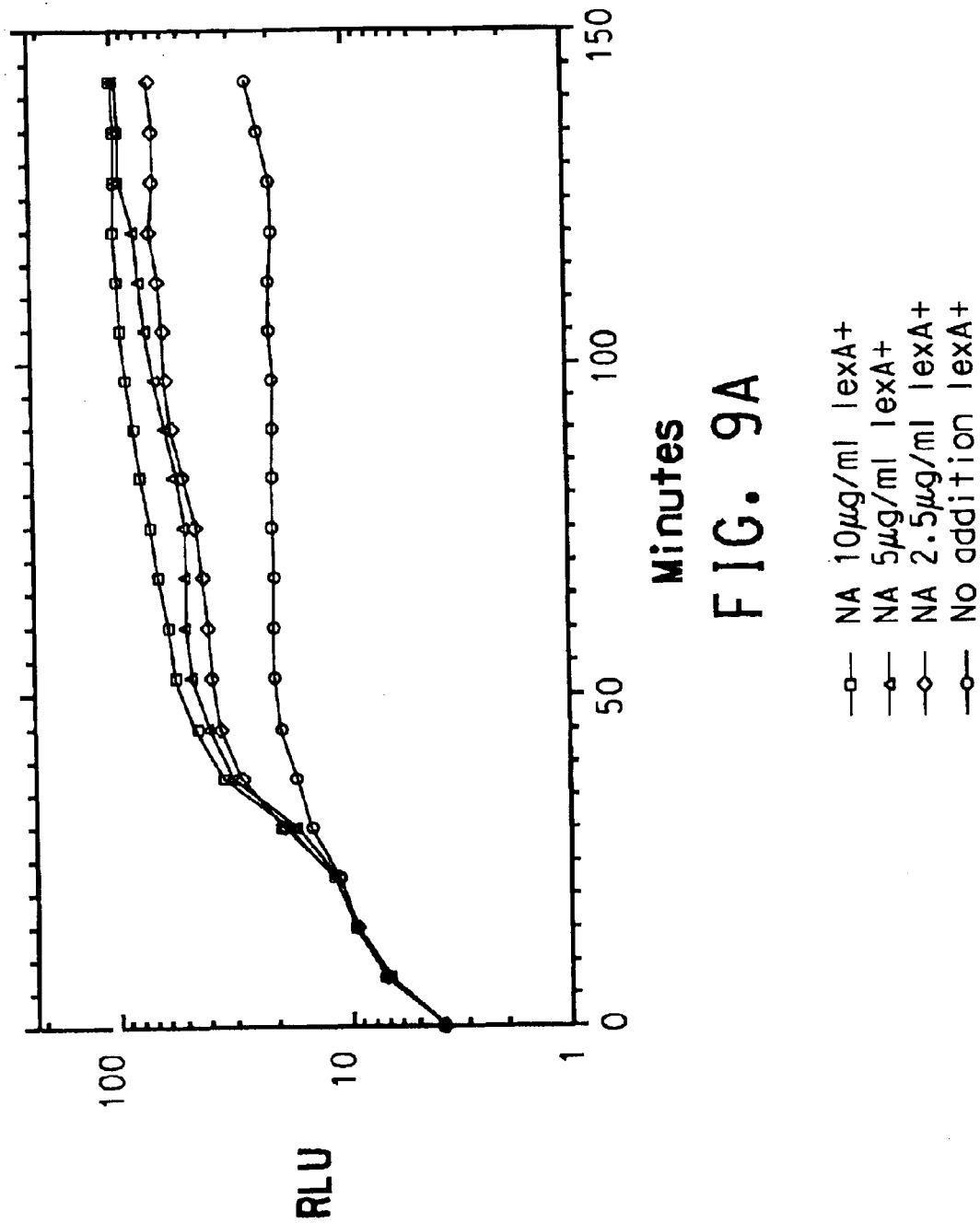

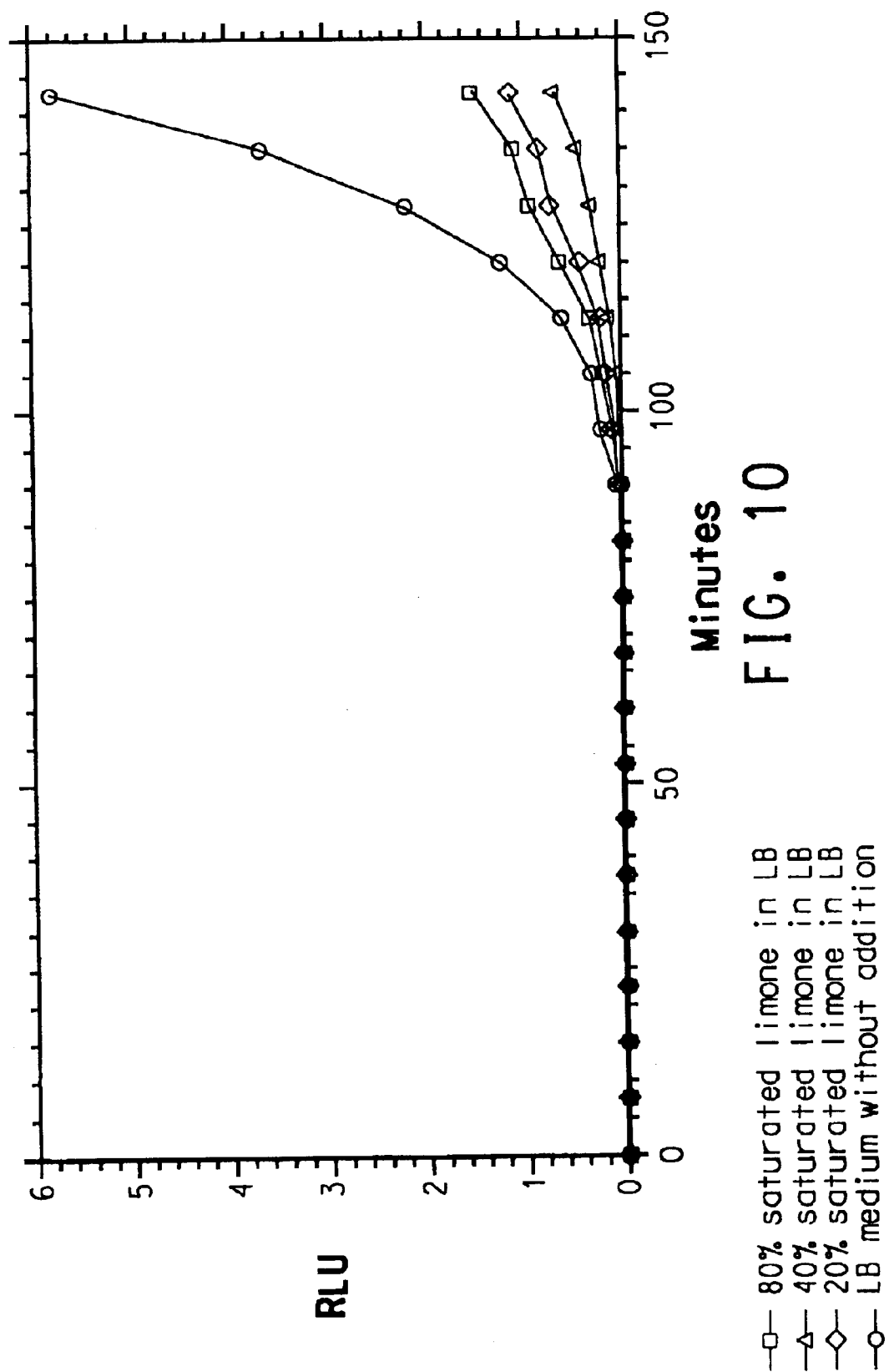

CELLULAR ARRAYS FOR THE IDENTIFICATION OF ALTERED GENE EXPRESSION

This application claims the benefit of U.S. Provisional Application No. 60/197,348 filed Apr. 14, 2000.

FIELD OF THE INVENTION

This invention is in the field of bacterial gene expression. More specifically, this invention describes a method to monitor transcriptional changes on a genome-wide scale using a genome-registered gene fusion collection.

BACKGROUND OF THE INVENTION

DNA array analysis is a powerful method for comprehensive genome analysis of gene expression. Currently, this approach is the only available method for massively parallel analyses that allow the expression of each gene of a bacterial genome to be characterized simultaneously (Richmond et al., (1999) *Nucleic Acids Res.* 27:3821–3835., 17, 25; Tao et al., (1999), *J. Bacteriol.* 181:6425–6440; Wilson et al., (1999) *Proc. Natl. Acad. Sci. U.S.A.* 96:12833–12838).

Richmond et al. ((1999) *Nucleic Acids Research*, 27:3821–3835) has recently reported genome-wide expression profiling of *E. coli* at the single ORF level of resolution. Changes in RNA levels after exposure to heat shock or IPTG were analyzed using comprehensive low density blots of individual ORFs on a nylon matrix and comprehensive high density arrays of individual ORFs spotted on glass slides. The results of the two methods were compared. Richmond et al. states that radioactive probe/spot blots are inferior to fluorescent probe/micro-arrays. Moreover, the comparison of heat shock treatment between the two methods is fundamentally flawed since the RNA analyzed with spot blots were derived from broth grown cultures while those analyzed with micro-arrays were derived from cells grown in defined media. Despite the power of this new methodology, there are several problems that limit the reliability of results. For example, artifacts may arise during the isolation of microbial RNA (Tao et al., (1999) *J. Bacteriol.* 181:6425–6440) or from cross hybridization to paralogous genes (Richmond et al., (1999) *Nucleic Acids Res.* 27:3821–3835, 17, 25).

Another limitation of DNA array methodology is that RNA must be isolated, converted into DNA by reverse transcriptase with concomitant incorporation of fluorescent labels. These steps make it unlikely that facile high throughput screens could be developed based on DNA array technology. Thus, there exists a need for a method that adapts results from DNA array technology into high throughput screens. For the reasons mentioned above and others, alternative genome-wide expression profiling method as well as rapid methods to independently verify results from DNA array experiments are needed.

Gene fusion technology is an established method for gene expression monitoring. For example, the initial discovery of the SOS (DNA damage responsive) regulon of *E. coli* was done by Kenyon and Walker ((1980) *Proc. Natl. Acad. Sci. U.S.A.* 77:2819–2823) by comparing the transcriptional responses of *Escherichia coli* to mitomycin C (MMC), a DNA damaging agent that intercalates into and forms a covalent attachment with double-stranded DNA. While these early experiments attempted to scan the bulk of the *E. coli* genome by using a transposon that put the lacZYA operon under the control of many promoter regions, it was not known if the entire genome had been surveyed because of the random nature of transposition and unknown location of the majority of transposition events. Accordingly, additional SOS regulon genes have been identified since these early experiments (Lomba et al., (1997) *Microbiol Lett* 156:119–122; Walker, (1996) In *Escherichia coli and Salmonella*: Cellular and Molecular Biology. ASM Press, pp 1400–1416).

LaRossa et al. (U.S. Pat. No. 5,683,868) has transformed *E. coli* with at construct comprised of luxCDABE operably linked to a variety of stress promoters. They have used the microorganisms to detect a variety of environmental insults such as Ethanol, $CdCl_2$ and toluene. The presence of sublethal concentration of insults is indicated by an increase in bioluminescence. However, in order to generate the transformed host, the stress promoters has to be identified and characterized. Furthermore, this method is limited to the stress response only.

Ashby and Rine (U.S. Pat. No. 5,569,588) reported a method to measure the transcriptional responsiveness of an organism to a candidate drug by detecting reporter gene product signals from separately isolated cells of a target organism on genome-wide bases. Each cell contains a recombinant construct with the reporter gene operatively linked to a different endogenous transcriptional regulatory element of the target organism When cells were treated with a candidate drug, the transcriptional responsiveness of the organism to the candidate drug was measured by the detecting the reporter signal from each cells. However, this method is useful with the organism only after the majority of transcriptional regulatory elements of the target organism are known and mapped. Furthermore, the reporter signals are measured only after cells reached homeostasis in the presence of drug. The initial transcriptional responses to chemicals are not considered.

The Lux-A Collection of random *E. coli* genomic DNA fused to the luxCDABE had been used to screen for those gene fusions for which expression was induced by treatment with the herbicide sulfometuron methyl. The DNA sequence of 19 of these sulfometuron methyl inducible gene fusions (smi-lux) was determined and used to identify the promoter controlling expression of the luxCDABE reporter (Van Dyk et al., (1998) *J. Bacteriol.* 180:785–792); the remaining 8047 gene fusions remained unidentified.

LaRossa and Van Dyk (U.S. Pat. No. 6,025,131) developed a method for the identification of gene regulatory regions, responsive to a particular cellular stress, such as that produced by herbicides or crop protection chemicals by randomly fusing regulatory regions to a bacterial luminescent gene complex where contacting the fusion in a suitable host with a cellular insult producing a cellular stress results in detection of that cellular stress by an increase in cellular luminescence. However, this method was limited to the perturbations in liquid media; luminescent responses were not detected on solid medium following overnight growth in the presence of a chemical stress. Furthermore, it did not allow regulatory region activity analysis in genome-wide scale.

The problem to be solved therefore is to provide a way to measure and follow the changes in gene expression using a genome-registered collection of reporter gene fusions in a manner that allows detection of initial transcriptional responses, and provide a way to cross-validate the results from other method (i.e., microarray) as well as to determine promoter and operon structure of genes, and further provide a way to test cellular responses to various environmental and genetic changes in high throughput manner.

SUMMARY OF THE INVENTION

A new method for the use of genome registered collection of reporter gene fusion is disclosed. Fragments of genomic DNA of host organism were fused to promoterless reporter gene. The reporter gene fusions were generated using restriction enzyme digestion, physical shearing of the genomic DNA, PCR, and transposition techniques. The reporter gene complexes were genome registered against the host genome on the basis of homology. Gene expression of each reporter gene complex is measure as reporter gene activity. The present invention provides a means to measure the changes in gene expression profiles in genome wide scale under various conditions in high throughput manner. In addition to being a stand-alone high throughput method, the present invention also provides a way to validate other genome-wide assays such as DNA microarray. The present invention also provides a method to confirm the response of several promoters to a particular insult (a condition or chemical of interest) as well as to identify a number of previously unknown operons responsive to that insult. Comparison of the gene expression patterns of two samples differing in one variable is also possible using this method. The present invention also provides the method to use an array of arrays by generating gene expression profiles that yield information relevant to understanding gene function and modes of chemical action. Such information can be gained by analysis of genetic alterations resulting in loss of function, reduced levels of gene products, or over-expression of gene products. Thus, an array of arrays can be used to enhance both mode of action studies and functional genomics.

In this invention, the sequencing and genome-registering of the majority of the Lux-A Collection members were completed. Lux fusions in the Lux-A Collection were fragments of $E.\ coli$ genomic DNA fused to promoterless luxCDABE gene. The genome-registered collection of lux fusions were examined for the biological responses measured by changes in bioluminescence. The present invention provides a means to measure the changes in gene expression profiles under various conditions.

In addition to being a stand-alone high throughput method, the present invention also provides the way to validate or detect false-positive result from other genome wide assays such as microarray.

The present invention provides a method to confirm the response of several promoters to a particular insult as well as to identify a number of previously unknown operons responsive to that insult.

The present invention provides a method for comparing the gene expression patterns of two samples differing in one variable. The variables may include but not limited to genotype, media, temperature, depletion or addition of nutrient, addition of an inhibitor, physical assault, biological assaults, irradiation, heat, cold, elevated or lowered pressure, desiccation, low or high ionic strength, and growth phases.

The present invention also provides the method to use an "array of arrays" by generating gene expression profiles that yield information relevant to understanding gene function and modes of chemical action. Such information can be gained by analysis of genetic alterations resulting in loss of function, reduced levels of gene products, or over-expression of gene products. Thus, an array of arrays can be used to enhance both modes of action studies and functional genomics.

Thus the invention provides a method for identifying altered gene expression between at least two genome-registered collections comprising:

(a) assembling at least two genome-wide scale, genome-registered collections;

(b) perturbing each collection from (a) with at least one perturbation;

(c) measuring the response of each collection to each perturbation of (b);

(d) analyzing the results of the at least one perturbation to identify genetic differences between the at least two genome-registered collections.

Additionally the invention provides a method for generating a genome-registered collection of reporter gene fusions comprising the steps of:

(a) generating a set of gene fusions comprising:
  1) a reporter gene or reporter gene complex operably linked to
  2) a genomic fragment from an organism of which at least 15% of the genomic nucleotide sequence is known;

(b) introducing in vitro the reporter gene fusions from step (a) into a host organism;

(c) registering the reporter gene fusions on the basis of sequence homology to the genomic sequence of the organism;

(d) repeating (a), (b), and/or (c) until reporter gene fusions have been made to at least 15% of the known genomic nucleotide sequence of said organism.

Similarly the invention provides a method for generating a genome-registered collection of reporter gene fusions comprising:

(a) generating random nucleic acid fragments from the DNA of an organism of which at least 15% of the nucleotide sequence is known;

(b) operably linking the random nucleic acid fragments generated in (a) to a vector containing a promoterless reporter gene or reporter gene complex;

(c) introducing the vector (b) containing the gene fusions into a host organism;

(d) determining the nucleic acid sequence of the distal and the proximal ends of the random nucleic fragments relative to the reporter gene or reporter gene complex;

(e) registering the sequenced fusions of step (d) on the basis of sequence homology to the genomic sequence of the host organism;

(d) repeating (a), (b), and/or (c) until reporter gene fusions have been made to at least 15% of the known genomic nucleotide sequence of said organism. Generation of the random nucleic acid fragments of step may incorporate restriction enzyme digestion, physical shearing of the genome and polymerase chain reaction.

In another embodiment the invention provides a method for generating a genome-registered collection of reporter gene fusions comprising steps of:

(a) introducing one or more transposons into the genome of an organism of which at least 15% of the nucleotide sequence is known, each transposon containing a promoterless reporter gene or reporter gene complex;

(b) determining the nucleic acid sequence of the junction between the proximal end of the genomic DNA and the transposon containing the reporter gene or reporter gene complex and registering the reporter gene fusions relative to the genomic sequence of the organism, (c) repeating (a) and (b) until reporter gene fusions have been made to at least 15% of the known genomic nucleotide sequence of said organism.

Alternatively the invention provides a method for identifying a profile of inducing conditions for a reporter gene fusion comprising:

(a) obtaining a gene expression profile of an organism under induced and non-induced conditions wherein induced genes are identified;

(b) providing a genome-registered collection of reporter gene fusions, said fusions registered to the genome of the organism of (a);

(c) selecting the reporter gene fusions of (b) that correspond to the induced genes of (a) to create a subset of the genome-register collection;

(d) contacting the subset of the genome-register collection of (c) with the inducing conditions of (a) to identify at least one representative reporter gene fusion whose expression was altered in a similar manner as in (a);

(e) contacting the at least one representative reporter gene fusion of (d) in a high throughput manner with a multiplicity of different inducing conditions to identify a profile of inducing conditions for that reporter gene fusion.

In another embodiment the invention provides a method for generating a genome-registered collection of reporter gene fusions comprising:

(a) providing a genome from an organism wherein at least 15% of the nucleotide sequence is known;

(b) providing a series of amplification primers having homology to specific known regions of the genome of (a);

(c) amplifying portions of the genome of (a) with the primers of (b) to create a collection of nucleic acid amplification products;

(d) operably linking the amplification products of (c) to a vector containing a promoterless reporter gene or reporter gene complex;

(e) introducing the reporter gene fusions into a said organism;

(f) repeating (a)–(e) until, until reporter gene fusions have been made to at least 15% of the known genomic nucleotide sequence of said organism.

In another embodiment the invention provides a method for identifying a profile of inducing conditions for a reporter gene fusion comprising:

(a) obtaining a gene expression profile for each of mutant strain and a parental strain organism under induced and non-induced conditions wherein induced genes are identified;

(b) providing a genome-registered collection of reporter gene fusions, said fusions registered to the genome of the organism of (a);

(c) selecting the reporter gene fusions of (b) that correspond to the induced genes of (a) to create a subset of the genome-register collection;

(d) contacting the subset of the genome-register collection of (c) with the inducing conditions of (a) to identify at least one representative reporter gene fusion whose expression was altered in a similar manner as in (a);

(e) contacting the at least one representative reporter gene fusion of (d) in a high throughput manner with a multiplicity of different inducing conditions to identify a profile of inducing conditions for that reporter gene fusion.

Similarly it is an object of the invention to provide a method to validate results from comprehensive genome analysis comprising the steps of:

(a) analyzing a genome-wide, gene expression assay of an organism treated with a condition or chemical of interest to identify genes with altered expression;

(b) selecting from a genome-registered collection of reporter gene fusions those reporter gene fusions containing promoter regions operably linked to genes corresponding to the altered genes from (a) or genes co-regulated with genes corresponding to the altered genes from (a);

(c) testing expression of the reporter gene fusions selected from (b) with the conditions or chemicals of interest used in (a); and (d) comparing the gene expression results from (c) to the gene expression result of (a).

The invention additionally provides a method to determine operon structure comprising steps of:

(a) selecting a subset of reporter gene fusions from a genome-registered collection of reporter gene fusions that map to the region of a possible operon;

(b) assaying the subset for the reporter gene function; and (c) determining a putative operon structure based on the quantities of reporter gene function.

Alternatively the invention provides a method for constructing a cellular array containing reporter gene fusions comprising:

(a) generating a set of gene fusions comprising:
1) a reporter gene or reporter gene complex operably linked to
2) a genomic fragment from an organism of which at least 15% of the genomic nucleotide sequence is known;

(b) selecting a non-redundant subset of reporter gene fusions from the set of (a) representative of at least 15% of known or suspected promoter regions from a genome-registered collection of reporter gene fusions, each containing a known or suspected promoter region operably linked to a reporter gene or reporter gene complex; and (c) fixing the non-redundant subset of reporter gene fusions of (b) in an array format.

In a preferred embodiment the invention provides a method for measuring gene expression responses to perturbation comprising:

(a) constructing at least 2 identical cellular arrays, each cellular array comprising a reporter gene fusion comprising:
1) a reporter gene or reporter gene complex operably linked to
2) a genomic fragment from an organism of which at least 15% of the genomic nucleotide sequence is known;

wherein at least one cellular array is a control array and at least one cellular array is an experimental array;

(b) contacting the experimental array of (a) with a perturbing condition;

(c) comparing the differences between the gene expression activity of the control and the experimental array wherein gene expression response to a perturbing condition is determined.

Organisms amenable to the present method include prokaryotes and fungi and particularly enteric bacterium.

Reporters useful in the present method include luxCDABE, lacZ, gfp, cat, galK, inaZ, luc, luxAB, bgaB, nptII, phoA, uidA and xylE.

BRIEF DESCRIPTION OF THE DRAWINGS

FIGS. 3 (A–C) describes generally the Luxarray 0.5 luminescence during solid phase growth.

FIG. 10 represents uhpT-lux upregulation by limonene.

Figure 1:
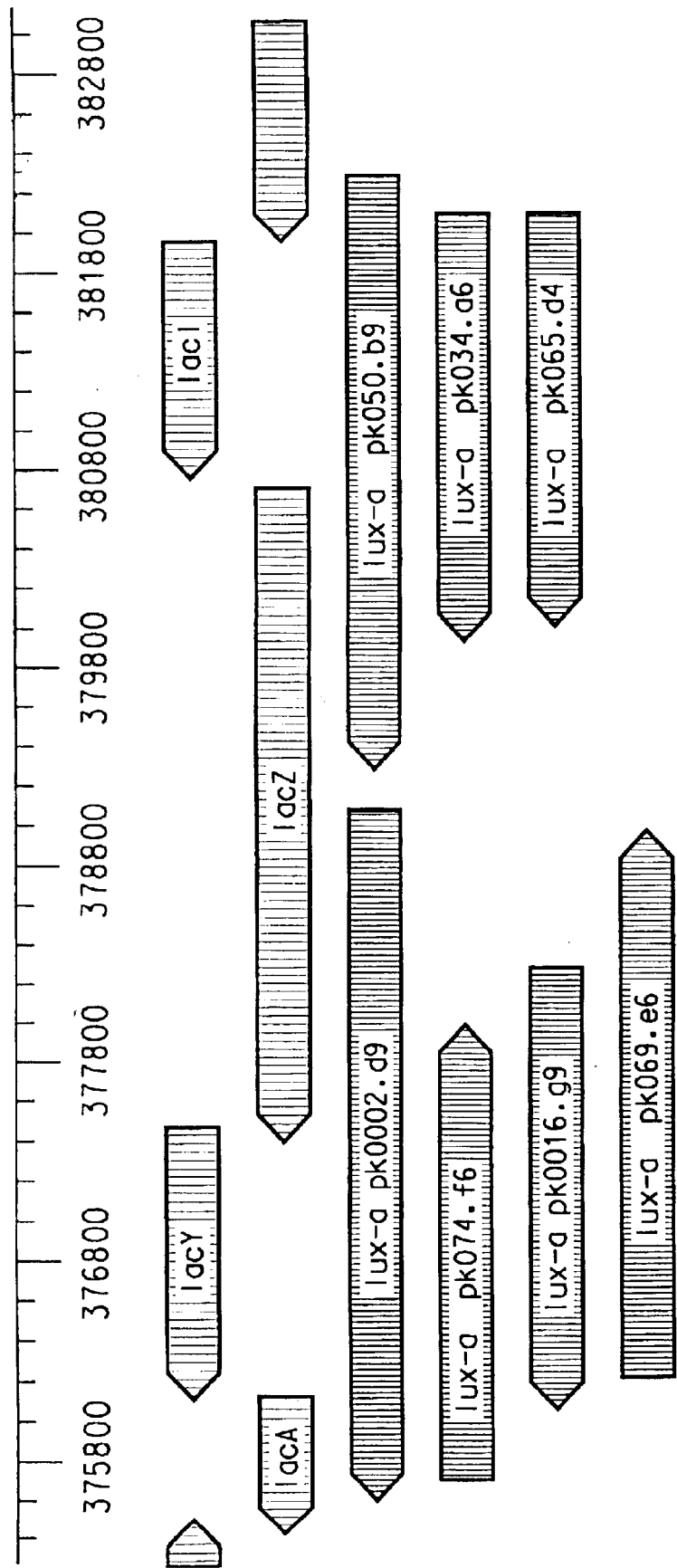
FIG. 1 is a diagram of fusions to the lac operon from the Lux-A Collection. The direction of the arrowhead indicates if the DNA of the cloned chromosomal segment is oriented such that a promoter, if present, would be driving expression of genes on the direct (arrowhead to the right) or complementary (arrowhead to the left) strand.

The invention can be more fully understood from the following detailed description and the accompanying sequence descriptions which form a part of this application.

DETAILED DESCRIPTION OF THE INVENTION

The present invention relates to the generation and use of a cellular array or a cellular array in combination with other genome-registered arrays (an array of arrays) for the determination of gene function and/or perturbation mode of action. Each cellular array consists of a number of microbial strains. Each strain comprises one reporter gene fusion made up of a gene or gene fragment operably linked to a reporter gene. Each gene or gene fragment has been "registered" or mapped to a specific location in the genome of the organism. Cellular arrays of the present invention are those that contain reporter gene fusions to at least 15% of the genome of the organism being analyzed. Cellular arrays containing these reporter gene fusions are referred to herein as "registered collections".

The genome-registered collection of the invention may be used to determine alterations in gene expression under a variety of conditions. Such collections are amenable to rapid assay and may be used to confirm, correct or augment data generated from DNA micro array technology.

In this disclosure, a number of terms and abbreviations are used. The following definitions are provided.

"Open reading frame" is abbreviated ORF. The term "ORF" is refers to a gene that specifies a protein.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase. Wherein the primer contains a sequence complementary to a region in one strand of a target nucleic acid sequence and primes the synthesis of a complementary strand, and a second primer contains a sequence complementary to a region in a second strand of the target nucleic acid and primes the synthesis of complementary strand; wherein each primer is selected to hybridize to its complementary sequence, 5' to any detection probe that will anneal to the same strand.

A "cellular array" means a set of strains differing from one another only in the chromosomal fragment fused to a reporter gene or reporter gene complex.

The term "array of arrays" refers to a collection of cellular arrays wherein each individual cellular array contains reporter gene fusions responsive to a specific inducing condition or set of conditions.

The terms "global scale" or "genome-wide scale" when applied to reporter gene fusions refer to a minimum 15% representation of the transcription units of an organism. For example, there is predicted to be 2328 transcription units (t.u.s) in *E. coli* (RegulonDB Database v.3.0, http://www.cifn.unam.mx/Computational_Biology/*E. coli*-predictions/). Thus a set of unique fusions representing 329 t.u.s (15% of 2328) is at "global scale". The term "global scale" or "genome-wide scale" when applied to mutations or overexpression refers to a minimum 15% representation of the open reading frames of an organism.

The term "genome register" refers to a procedure of precisely locating or mapping a defined nucleic acid sequence within a genome.

The term "genome-registered collection" refers to a set of strains containing reporter gene fusions, loss of gene function mutations, altered gene function mutations, or overexpressed genes that have been "registered" or mapped by homology to the nucleic acid sequence of the genome of the organism. These genome-registered collections include reporter gene fusions to at least 15%, more preferably at least 20%, and most preferably at least 50% of all known or predicted promoter regions, loss of gene function mutations in at least 15%, more preferably at least 20%, and most preferably at least 50%, of all known or predicted ORFs, altered gene function mutations in at least 15%, more preferably at least 20%, and most preferably at least 50%, of all known or predicted ORFs, or overexpression of in at least 15%, more preferably at least 20%, and most preferably at least 50%, of all known or predicted ORFs.

As used herein the term "known" as applied to a gene or ORF within the context of a genome means that the sequence of the gene or ORF is known and should not be limited to knowledge of the function of that gene or ORF.

The term "reporter gene fusion" refers to a chimeric gene consisting, in one part, of a gene or genes that are useful to detect transcription and/or translation initiated in the other part.

The term "reporter gene complex" refers to any set of two or more genes that together are useful to generate a measurable signal.

The term "reporter gene activity" or "reporter construct activity" refers to the accumulation of the limiting component(s) of the reporter system in use which results in the measurable signal associated with that reporter system. The measured activity is the sum result of the de novo production, ongoing degradation or deactivation, and/or activation of the limiting component(s).

The term "Lux-A Collection" refers to a specific set of *E. coli* strains containing plasmid-borne luxCDABE fusions.

The term "lux fusion" or "luxCDABE fusion" refers to a chimeric gene consisting, of a genomic sequence joined to luxCDABE genes.

The term "congenic strains" refer to two or more strains that differ from one another by a single mutation or a strain differing in only one gene to denote genes whose expression differ as a function of the allele.

The term "DNA microarray" or "DNA chip" means assembling PCR products of a group of genes or all genes within a genome on a solid surface in a high density format or array. General methods for array construction and use are available (see Schena M, Shalon D, Davis R W, Brown P O., Quantitative monitoring of gene expression patterns with a complementary DNA microarray. *Science*. Oct. 20, 1995; 270(5235): 467–70 and http://cmgm.stanford.edu/pbrown/mguide/index.html). A DNA microarray allows the analysis of gene expression patterns or profile of many genes to be performed simultaneously by hybridizing the DNA microarray comprising these genes or PCR products of these genes with cDNA probes prepared from the sample to be analyzed. DNA microarray or "chip" technology permits examination of gene expression on a genomic scale, allowing transcription levels of many genes to be measured simultaneously. Briefly, DNA microarray or chip technology comprises arraying microscopic amounts of DNA complementary to genes of interest or open reading frames on a solid surface at defined positions. This solid surface is generally a glass slide, or a membrane (such as nylon membrane). The DNA sequences may be arrayed by spotting or by photolithography (see http://www.affymetrix.com/). Two separate fluorescently-labeled probe mixes prepared from the two sample(s) to be compared are hybridized to the microarray and the presence and amount of the bound probes are detected by fluorescence following laser excitation using a scanning confocal microscope and quantitated using a laser scanner and appropriate array analysis software packages. Cy3 (green) and Cy5 (red) fluorescent labels are routinely used in the art, however, other similar fluorescent labels may also be employed. To obtain and quantitate a gene expression profile or pattern between the two compared samples, the ratio between the signals in the two channels (red:green) is calculated with the relative intensity of Cy5/Cy3 probes taken as a reliable measure of the relative abundance of specific mRNAs in each sample. Materials for the construction of DNA microarrays are commercially available (Affymetrix (Santa Clara Calif.) Sigma Chemical Company (St. Louis, Mo.) Genosys (The Woodlands, Tex.) Clontech (Palo Alto Calif.) and Corning (Corning N.Y.). In addition, custom DNA microarrays can be prepared by commercial vendors such as Affymetrix, Clontech, and Corning.

The basis of gene expression profiling via micro-array technology relies on comparing an organism under a variety of conditions that result in alteration of the genes expressed. A single population of cells may be exposed to a variety of stresses that will result in the alteration of gene expression. Alternatively, the cellular environment may be kept constant and the genotype may be altered. Typical stresses that result in an alteration in gene expression profile will include, but is not limited to conditions altering the growth of a cell or strain, exposure to mutagens, antibiotics, UV light, gamma-rays, x-rays, phage, macrophages, organic chemicals, inorganic chemicals, environmental pollutants, heavy metals, changes in temperature, changes in pH, conditions producing oxidative damage, DNA damage, anaerobiosis, depletion or addition of nutrients, addition of a growth inhibitor, and desiccation. Non-stressed cells are used for generation of "control" arrays and stressed cells are used to generate an "experimental", "stressed" or "induced" arrays. Induced arrays are those that demonstrate "altered gene expression".

"Altered gene expression" refers to the change in the level of a transcription or translation products. If the gene is "up-regulated", the level of transcription or translation products is elevated. If the gene is "down-regulated" the level of transcription or translation products is decreased. Conditions under which gene expression is altered is also known as an "inducing condition". In some instance a number of different conditions may result in the same transcriptional effect on a single gene. Thus a number of inducing conditions will either up-regulate or down regulate the same gene. This collection of like inducing conditions is known as a "profile of inducing conditions". Similarly the term "perturbation" as used herein in reference to a cellular array or a DNA micro array is any alteration of environment or genotype the results in altered gene expression.

The terms "high density" or "comprehensive" micro array refers to a high-density DNA micro-array containing at least 75% of the open reading frames of the organism.

The term "expression profile" refers to the expression of groups of genes.

The term "gene expression profile" refers to the expression of individual gene and suite of individual genes.

The "comprehensive expression profile" refers to the gene expression profile of more than 75% of genes in the genome. In "comprehensive gene expression analysis" at least >75% of gene expression of the organism is analyzed.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The terms "print" or "printing" refer to transferring one or more cultures from one locale, most often a multiwell culture plate, to a substrate or solid surface by physical contact transfer or any of a plurality of technologies.

The term "regulon" refers to groups of operons sharing similar regulation.

The term "operon" refers to a unit of bacterial gene expression and regulation, including structural genes and control elements in DNA recognized by regulator gene product(s) that in combination support the production of an mRNA.

The term "probe" refers to a single-stranded nucleic acid molecule that can base pair with a complementary single stranded target nucleic acid to form a double-stranded molecule.

The term "genotype" refers to the genetic constitution of an organism as distinguished from its physical appearance.

The term "genomic DNA" refers to a single complete set of genetic information carried in the chromosomes of an organism.

The term "total RNA" refers to non-fractionated RNA from an organism.

The terms "protein specifying RNA" or "protein specifying transcript" refer to RNA derived from an ORF.

The terms "transposon" and "transposable element" are used interchangeably and mean a region of nucleic acid that is capable of moving from one position to another where this movement is catalyzed by the element itself.

The term "transposition" means a biochemical reaction that catalyzes the movement of a transposable element from one site into different site within a DNA molecule. Transposition can be carried out in vivo or in vitro.

The term "in vitro transposition" means a biochemical reaction initiated outside the cell that catalyzes the movement of a transposable element from one site into different site within a DNA molecule.

The term "in vivo transposition" means a biochemical reaction that takes place within the cell that catalyzes the mobilization of a transposon from of site to another within the genome of the host.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 12.1 therein (entirely incorporated herein by reference). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). Furthermore, the skilled artisan will recognize that the temperature and wash solution salt concentration may be adjusted as necessary according to factors such as length of the probe.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Gene" refers to a nucleic acid fragment that expresses a specific protein, including regulatory sequences preceding (5' non-coding sequences) and following (3' non-coding sequences) the coding sequence, unless mentioned otherwise. For example, "reporter genes" used in gene fusion does not include regulatory (promoter) sequences unless specified otherwise. "Native gene" refers to a gene as found in nature with its own regulatory sequences.

The terms "chimeric gene", "gene fusion", or "fusion" refer to any non-native gene or genes comprising two or more genomic or artificial DNA fragments that are not found in nature. Accordingly, a chimeric gene, gene fusion or fusion may comprise regulatory sequences and coding sequences the are derived from different sources, or regulatory sequences and coding sequences derived from the same source but arranged in a manner that different than that is found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

The term "promoter" refers to a DNA sequence to which RNA polymerase can bind to initiate the transcription. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. "Promoter region" is promoter and adjacent areas whose function may be modulate promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the acquisition of new genes in a cell after the incorporation of nucleic acid.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "restriction endonuclease" or "restriction enzyme" refers to an enzyme which binds and cuts within a specific nucleotide sequence within double stranded DNA.

The term "bioluminescence" refers to the phenomenon of light emission from any living organism.

The term "relative light unit" is abbreviated "RLU" and refers to a measure of light emission as measured by a luminometer, calibrated against an internal standard unique to the luminometer being used.

The term "stress" or "environmental stress" refers to the condition produced in a cell as the result of exposure to an environmental insult.

The terms "insult" or "environmental insult" refers to any substance or environmental change that results in an alteration of normal cellular metabolism in a bacterial cell or population of cells. Environmental insults may include, but are not limited to, chemicals, environmental pollutants, heavy metals, changes in temperature, changes in pH as well as agents producing oxidative damage, DNA damage, anaerobiosis, changes in nitrate availability or pathogenesis.

The term "stress response" refers to the cellular response resulting in the induction of either detectable levels of stress proteins or in a state more tolerant to exposure to another insult or an increased dose of the environmental insult.

The term "stress gene" refers to any gene whose transcription is induced as a result of environmental stress or by the presence of an environmental insults.

The terms "log phase", "log phase growth", "exponential phase", or "exponential phase growth" refer to cell cultures of organisms growing under conditions permitting the exponential multiplication of the cell number.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

In this invention, a random set of fragments of *E. coli* genome was generated by partially digesting *E. coli* genome with the restriction enzyme Sau3A1, and separating the fragments by size fractionation. The fraction with an average size of 1.8 KB was isolated and ligated to the plasmid pDEW201 which contains the origin of replication and bla from pBR322, four transcription terminators upstream of the promoterless luxCDABE gene. The ligation products were transformed into *E. coli* XL2Blue cells. Approximately 24000 resulting transformants were pooled and used AS the source of heterologous plasmid DNA. This plasmid DNA pool was used to transform *E. coli* DPD1675 cells. A total of 8066 individual transformants were isolated and labeled as Lux-A Collection. A homology search for the sequence from beginning and end of clones from Lux-A Collection was performed against complete *E. coli* sequence. The location and orientation of each chimeric gene fusion with respect to the *E. coli* genome was determined based on the computed homology. Additional sequences for the collection can be added by more random fusions or inverting the orientation of DNA in the fusion to put the promoter regions in the right orientation for the inserted DNA by using the method that is routine in the art.

Preferred organisms for use in the present invention are those whose genomes are being sequenced or that have completely sequenced genomes and are amenable to introduction of gene fusions by transduction, transformation, or conjugation. They include but are not limited to the 113 organisms listed on the WEB page, http://www.ncbi.nlm.nih.gov/PMGifs/Genomes/bact.html as of Feb. 15, 2000. In addition to the organisms mentioned above, any microbial organism with at least 15%, preferably 20%, and most preferably 50% of its genome sequence known that is amenable to introduction of gene fusions by transduction, transformation, or conjugation can be used in this invention to generate reporter gene fusions.

Within the context of the present invention prokaryotes and fungi having at least 15% of their genome sequence are particularly suitable. Of the prokaryotes, enteric bacteria such as Escherichia and Salmonella are preferred and *E. coli* is most preferred as it is well characterized and its genome has been sequenced it is most preferred prokaryotic organism for this invention.

It will be appreciated that for the purposes of the present invention that the teachings with respect to *E. coli* are particularly adaptable to any of the enteric bacteria. Enteric bacteria are members of the family Enterobacteriaceae, and include such members as Escherichia, Salmonella, and Shigella. They are gram-negative straight rods, 0.3–1.0×1.0–6.0 $\mu$m, motile by peritrichous flagella, except for Tatumella, or nonmotile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of *Shigella dysenteriae* 0 group 1 and *Xenorhabdus nematophilus*, catalase positive. Nitrate is reduced to nitrite except by some strains of Erwinia and Yersina. The G+C content of DNA is 38–60 mol % ($T_m$, Bd). DNAs from species from species within most genera are at least 20% related to one another and to *Escherichia coli*, the type species of the family. Notable exceptions are species of Yersina, Proteus, Providenica, Hafnia and Edwardsiella, whose DNAs are 10–20% related to those of species from other genera. Except for *Erwinia chrysanthemi* all species tested contain the enterobacterial common antigen (Bergy's Manual of Systematic Bacteriology, D. H. Bergy, et al., Baltimore: Williams and Wilkins, 1984).

As for the reporter gene or gene complex, luxCDABE is most preferred for its sensitivity and simplicity of assay conditions. Other reporter genes well known in the art also can be used in this invention. The preferred reporter genes include but are not limited to lacZ, gfp, cat, galK, inaZ, luc, luxAB, bgaB, nptII, phoA, uidA, and xylE.

Methods to introduce fusions into such strains are well known in the art. Fusions can be introduced by transduction, transformation or conjugation as appropriate for each specific organism. They can be constructed in vitro by techniques including but not limited to transposon (e.g., Tn7) mediated transposition, ligating of random fragments to a reporter gene construct containing a vector, or ligating of PCR products to the same vector. They can be constructed by in vivo transposition where the transposon is introduced into the cell by transduction, transformation, or conjugation. Kits for in vitro transposition are commercially available (see for example The Primer Island Transposition Kit, available from Perkin Elmer Applied Biosystems, Branchburg, N.J., based upon the yeast Ty1 element (including the AT2 transposon); The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

The preferred methods to generate a set of fragments of the genome include but are not limited to, the partial digestion with a restriction enzyme, physical shearing, polymerase chain reaction (PCR) amplification, the combination of restriction enzyme digestion and PCR, the combination of restriction enzyme digestion and physical shearing, the combination of physical shearing and PCR, and the combination of all three. Above methods for generating fragments are well known in the art. For example PCR is well described in (U.S. Pat. No. 4,683,202 (1987, Mullis, et al.) and U.S. Pat. No. 4,683,195 (1986, Mullis, et al.), and restriction enzyme digestion and physical shearing is well described in Sambrook et al., supra.

When using PCR to generate fragments several approaches may be taken. In one instance random primers may be used to amplify portions of the genome. In this situation the fragments, (amplification products) generated will be random in nature. In the alternative, where portions of the sequence of the genome are known primers may be designed to specific loci within the genome. This is a directed fragment generation approach.

Furthermore, chimeric reporter gene fusions can be also made by using transposition at the genome level. The above-described methods for generating transpositions are well known in the art.

After the sequencing and genome-registering the majority of the Lux-A Collection members were completed the biological responses of the strain collection containing luxCDABE fusions to members of well-characterized regulatory circuits were examined. Thus, gene fusions to the lac operon, and members of the heat shock, SOS, SoxRS, and OxyR regulons were selected from the Lux-A Collection and the responses to known inducers of each of these global regulatory circuits were determined.

Appropriate biological responses were demonstrated for each of regulons mentioned above. The Lux-A Collection contained 3 members that are fusions of luxCDABE to the lac operon (FIG. 1). These cultures were grown in the presence of glucose and bioluminescence was measured and compared to the cultures grown in the absence of glucose. Cultures grown in the absence of glucose were much more highly bioluminescent than the ones in the presence of glucose.

Four out of twelve heat shock promoters were found as lux fusions. A total of 6 fusion containing strains were isolated and tested for the stress response in the presence of various concentration of ethanol. The heat shock regulon gene fusions from the Lux-A Collection confirmed induction of heat shock response by ethanol.

For SOS regulon, 7 lux fusion were found in the Lux-A Collection. When these stains were tested with DNA damaging chemical nalidixic acid, increased level of bioluminescence was observed. However, treatment with ethanol did not induce bioluminescence in the same culture.

In a similar fashion, although SoxR/S and OxyR regulons were not fully represented in the Lux-A Collection, the biologically appropriate response was observed.

Thus, while the Lux-A Collection is not comprehensive in containing a fusion controlled by each promoter in *E. coli*, it nonetheless provides a genomic-wide overview of transcriptional responses to imposed stresses and can be adapted to optimize responses.

The effect of mitomycin C (MMC), a known DNA damaging agent, was tested with DNA microarray and the resulting gene expression pattern was compared with the gene expression data from the treated cells of the Lux-A Collection. As expected, the expression of the known SOS genes was elevated in micro array data. However the expression of several SOS regulon genes was elevated less than 2-fold (Table 12) and as such were within a large group of 792 genes the expression of which was elevated by 20% or more. Because most of these are likely due to artifacts in the array data rather than to actual biologically relevant responses, the group of genes with less than two fold increase in expression were considered MMC non-inducible genes. Had these experiments been conducted using a compound with an otherwise unknown mode of action, some biologically relevant gene expression events would have been missed with the DNA micro array approach. To test if strains carrying luxCDABE gene fusions would yield the expected positive result, the three gene fusions that were available in the Lux-A Collection of reporter gene fusions were tested for mitomycin C responses. In all three cases, mitomycin C induced increased bioluminescence. Thus, this demonstrates that negative results from DNA microarrays can be questioned by contradictory positive results with corresponding gene fusions.

The genes not previously known to be upregulated with mitomycin C, provide an opportunity to further examine the correlation of DNA array and gene fusion experimental data. For this class of genes, four fusions were available in the Lux-A Collection of reporter gene fusions. The corresponding luxCDABE fusions to these four genes provided no evidence of increased gene expression induced by MMC. Thus, the positive results from the array were classified as false-positive.

Figure 2:
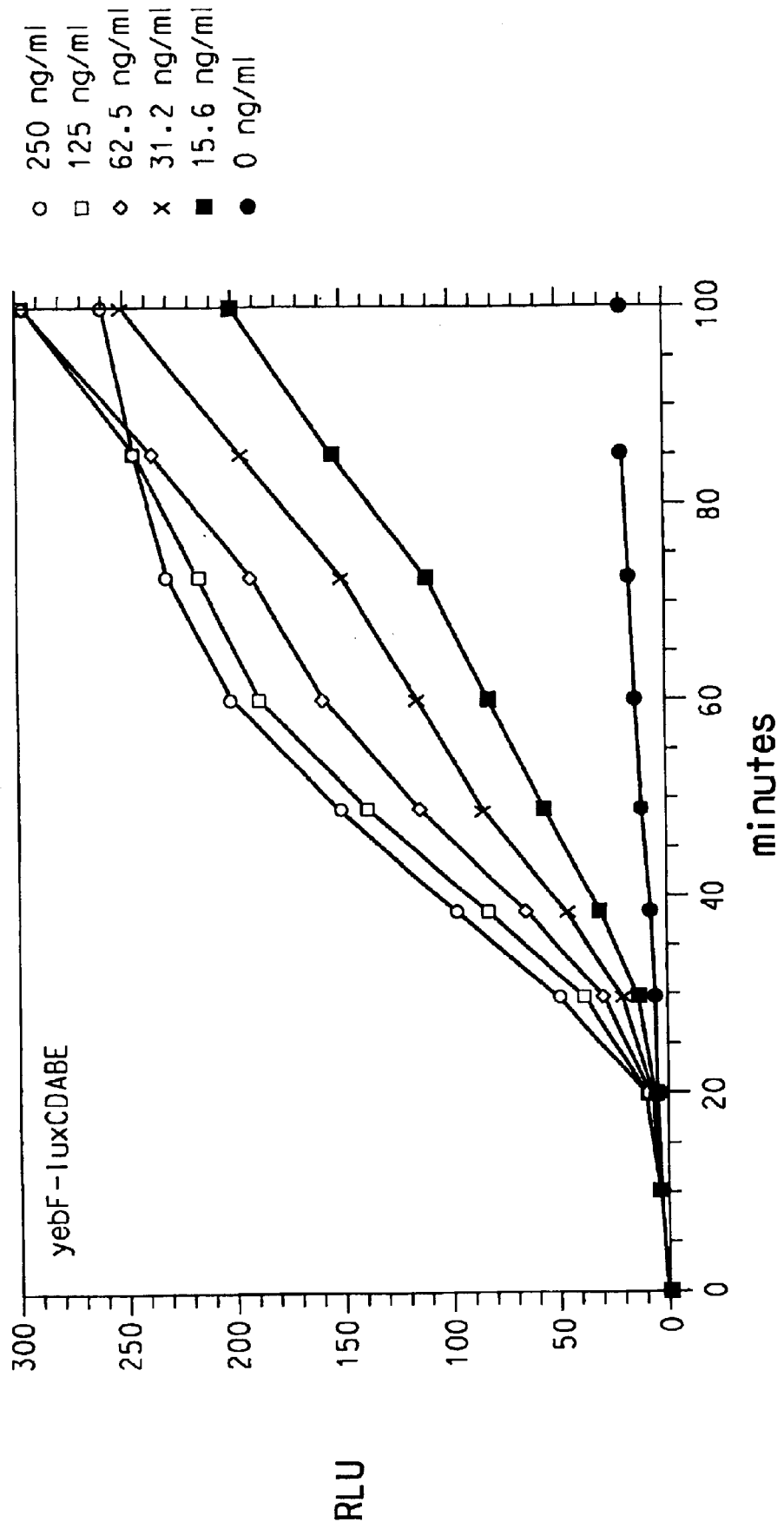
FIG. 2 describes kinetics of induction of increased bioluminescence from *E. coli* strain DPD3232 containing a yebF-luxCDABE fusion treated with various concentrations of MMC.

One gene fusion in the Lux-A Collection of gene fusions was found to have a genomic fragment that when inverted would result in a fusion to yebF, a gene observed to be upregulated by mitomycin C in DNA micro array experiments. When the genomic DNA fragment was released and inserted back into the vector, bioluminescence from some of the transformed colonies were found to be highly inducible by another DNA damaging agent, nalidixic acid, strongly suggesting that the inversion of DNA might have occurred. Furthermore, induction of bioluminescence by MMC was demonstrated as shown in FIG. 2.

The induction of increased gene expression from the yebF-lux fusion not only validates the data from the DNA array study, but furthermore, allows facile dose response and kinetic analyses and provides a biosensor strain for a high throughput screen. It is possible that the DNA damage response reported by yebF-lux fusion might be mediated by the well-characterized SOS response because there is a LexA box upstream of yebG (Lomba et al., (1997) *FEMS Microbiol Lett* 156:119–122), which is just upstream of yebF. However, there is also suggested to be a promoter that drives transcription of the yebF gene (Blattner et al., (1997) *Science* 277:1453–1462), therefore the induction of yebF expression by MMC was unexpected. Thus, these results demonstrate the concept that a previously unknown gene expression event can be discovered with a DNA microarray, then a corresponding lux gene fusion can be used to validate and extend the results. Furthermore, such a lux fusion strain can form the basis of a high throughput screen based on gene expression changes.

The yebF-luxCDABE gene fusion mentioned in the Example 3 can be used as a high throughput screen for compounds other than MMC and nalidixic acid that result in DNA damage. The use of the luxCDABE bioluminescent reporter fusion allows facile detection of reporter gene activity in a manner that does not require cell lysis or addition of enzymatic substrates. Thus development of a high throughput screen only requires an instrument to quantitate light production (of which there are many available commercially) and a source of bacterial cell cultures containing the gene fusion of choice. Such bacterial cell cultures can be supplied by one of several methods. A basic way to use bacterial strains containing gene fusions is simply with freshly grown bacterial cell cultures. An alternative to daily cultivation is the use of frozen culture aliquots, such as has been successfully demonstrated with an *E. coli* bioluminescent sensor that is competent for gene expression assays immediately after thawing, having been previously stored at $-80°$ C. using a cryoprotectant such as glycerol (Sticher et al., (1997) *Appl. Environ. Microbiol.* 63:4053–4060). Two other common methods of handling bacteria, lyophilization and continuous culture, have also proven to be useful sources of lux fusion strains for testing purposes. Lyophilization has been successfully applied to metal responsive and heat shock responsive cellular biosensor strains (Corbisier et al., (1996) *Environ. Toxicol. Water Qual.* 11:171–177; Tauriainen et al., (1998) *Biosensors & Bioelectronics* 13:931–938; Tauriainen et al., (1997) *Appl. Environ. Microbiol.* 63:4456–4461; Van Dyk and Wagner (1998) U.S. Pat. No. 5,731,163; Wagner and Van Dyk (1998), Methods in Molecular Biology: Bioluminescence Methods and Protocols, vol. 102. Humana Press Inc p.: 123–127). Continuous cultivation of *E. coli* bioluminescent biosensors in mini bioreactors has been shown to yield reproducible detection of stress responses (Gu et al., (1996), *Biotechnol. Prog.* 12:393–397; Gu et al., (1999) *Biosens. Bioelectron.* 14:355–361).

Other possible methods to supply cellular biosensors for high throughput screens are immobilization by entrapment in a carrier material or use of a bioluminescent bioreporter integrated circuit (BBIC). Strontium alginate immobilization of a lux fusion containing bacterial strain has been demonstrated for use as a probe for waste streams (Heitzer et al., (1994)*Appl. Environ. Microbiol.* 60:1487–1494; Matrubutham et al., (1997) *Appl. Microbiol. Biotechnol.* 47:604–609; Webb et al, (1997) *Biotechnol. Bioeng.* 54:491–502). In another example of immobilization, calcium alginate beads, harboring an SOS responsive lux fusion strain, stored in a $CaCl_2$ solution at 4° C. were found to give useful DNA damage induction responses for up to one month after formation (Davidov et al., in press). Likewise, calcium alginate immobilization of a copper-responsive biosensor results in superior stability of the biosensor relative to the immobilization of the same biosensor in agarose (de Lorenzo et al., (1999)*Anal. Chim. Acta* 387:235–244). Furthermore, combining of immobilized cells and light detection equipment is possible for sensors that produce visible light as a signal. In one such case, an *E. coli* luc fusion strain is immobilized on the end of fiber optic monitoring device (Ikariyama et al., (1997) *Anal. Chem.* 69:2600–2605). Finally, in the BBIC approach, which takes advantage of the cellular signal generated by the five gene luxCDABE reporter, a bioluminescent biosensor strain is deposited onto a micro-luminometer fabricated within an integrated circuit; the light produced by the biosensor is detected by the integrated circuit, which then processes and communicates the results (Simpson et al., (1998) *Soc. Opt. Eng.* 3328 (Smart Electronics and MEMS):202–212; Simpson et al., (1998) TIBTECH 16:332–338).

Therefore, development of a DNA damage responsive high throughput screen based on the newly discovered yebF-luxCDABE fusion is readily accomplished by choosing one of the above known methods to provide an active cellular biosensor and combining it, if necessary, with an instrument that measures visible light production. Other promoters from a stress response gene may be used to generate high throughput screens using a lux fusion. Stress response gene promoters from both prokaryotic and eukaryotic cells may be used, however promoters from bacteria are preferred and promoters from *E. coli* are most preferred. Suitable stress response gene promoters may be selected from but are not limited to the list of genes under the heading "responding genes" given in Table 1 below, and other newly discovered regulatory circuits.

TABLE 1

| STIMULUS | REGULATORY GENE(S) | REGULATORY CIRCUIT | RESPONDING GENES* |
|---|---|---|---|
| Protein Damage[a] | rpoH | Heat Shock | grpE, dnaK, lon, rpoD, groESL, lysU, htpE, htpG, htpI, htpK, clpP, clpB, htpN, htpO, htpX, etc. |
| DNA Damage[b] | lexA, recA | SOS | recA, uvrA, lexA, umuDC, uvrA, uvrB, uvrC, sulA, recN, uvrD, ruv, dinA, dinB, dinD, dinF etc. |
| Oxidative Damage[c] | oxyR | Hydrogen Peroxide | katG, ahp, etc. |
| Oxidative Damage[d] | soxRS | Superoxide | micF, sodA, nfo, zwf, soi, etc. |
| Membrane Damage[e] | fadR | Fatty Acid Starvation | fabA |
| Any[f] | ? | Universal Stress | uspA |
| Stationary Phase[g] | rpoS | Resting State | xthA, katE, appA, mcc, bolA, osmB, treA, otsAB, cyxAB, glgS, dps, csg, etc. |
| Amino Acid Starvation[h] | relA, spoT | Stringent | his, ilvBN, ilvGMEDA, thrABC, etc. |
| Carbon Starvation[i] | cya, crp | Catabolite Activation | lac, mal, gal, ara, tna, dsd, hut, etc. |
| Phosphate Starvation[j] | phoB, phoM, phoR,phoU | P Utilization | phoA, phoBR, phoE, phoS, aphA, himA, pepN, ugpAB, psiD, psiE, psiF, psiK, psiG, psiI, psiJ, psiN, psiR, psiH, phiL, phiO, etc. |
| Nitrogen Starvation[k] | glnB, glnD, glnG, glnL | N Utilization | glnA, hut, etc. |

*Genes whose expression is increased by the corresponding stimulus and whose expression is controlled by the corresponding regulatory gene(s).
[a]Neidhardt and van Bogelen in *E. coli* and *Salmonella typhimurium*; Cellular and Molecular Biology (Neidhardt, F. C., et al. Eds., pp. 1334–1345, American Society of Microbiology, Washington, DC (1987))
[b]Walker in *E. coli* and *Salmonella typhimurium*; Cellular and Molecular Biology (Neidhardt, F. C., et al. Eds., pp. 1346–1357, American Society of Microbiology, Washington, DC (1987))
[c]Christman et al. Cell 41: 753–762 (1985); Storz et al. Science 248: 189–194 (1990); Demple Ann. Rev. Genet. 25: 315–337 (1991)
[d]Demple, Ann. Rev. Genet. 25: 31 337 (1991)
[e]Magnuson et al. Microbiol. Rev 57: 522–542 (1993)
[f]Nystrom and Neidhardt, J. Bacteriol, 175: 2949–2956 (1993); Nystrom and Neidhardt (Mol. Microbiol. 6: 3187–3198 (1992)
[g]Kolter et al. Ann. Rev. Microbiol. 47: 855–874 (1993)
[h]Cashel and Rudd in *E. coli* and *Salmonella typhimurium*; Cellular and Molecular Biology (Neidhardt, F. C., et al. Eds., pp. 1410–1438, American Society of Microbiology, Washington, DC (1987)); Winkler in *E. coli* and *Salmonella typhimurium*; Cellular and Molecular Biology (Neidhardt, F. C., et al. Eds., pp. 395–411, American Society of Microbiology, Washington, DC (1987))
[i]Neidhardt, Ingraham and Schaecter. Physiology of the Bacterial Cell: A Molecular Approach, Sinauer Associates, Sunderland, MA (1990), pp 351–388; Magasanik and Neidhardt in E. coil and *Salmonella typhimurium*; Cellular and Molecular Biology (Neidhardt, F. C., et al. Eds., pp. 1318–1325, American Society of Microbiology, Washington, DC (1987))
[j]Wanner in *E. coli* and *Salmonella typhimurium*; Cellular and Molecular Biology (Neidhardt, F. C., et al. Eds., *E. coli* and *Salmonella typhimurium*; Cellular and Molecular Biology (Neidhardt, F. C., et al. Eds., pp. 1326–1333, American Society of Microbiology, Washington, DC (1987))
[k]Rietzer and Magasanik in *E. coli* and *Salmonella typhimurium*; Cellular and Molecular Biology (Neidhardt, F. C., et al. Eds., pp. 1302–1320, American Society of Microbiology, Washington, DC (1987)); Neidhardt, Ingraham and Schaecter. Physiology of the Bacterial Cell: A Molecular Approach, Sinauer Associates, Sunderland, MA (1990), pp 351–388

Fusions to lux reporter genes can also be used to support identification of the operonic structures, newly discovered regulatory circuits, and promoter sites. Since the random library of *E. coli* genomic DNA was fused to the promoterless lux gene, the strength of bioluminescence in the resulting fusions should depend on the promoter from the *E. coli*. For example, if the fusion contains the complete promoter, lux gene expression would be stronger than the fusion that contains a partial region of same promoter. If the promoter is truncated to the point that it is non-functional, the lux gene expression would be absent. Such result can support the postulated operonic structures and dependence of promoter function in host (Example 4).

The construction and sequencing of a random library of *E. coli* genomic fragments in plasmid pDEW201 has generated a genome-registered set of promoter activity reporter constructs. A highly parallel, solid phase cellular assay has been developed utilizing a subset of these reporters by combining bioinformatic analysis and robotic manufacturing of arrays and high throughput culture production. This assay has the capacity, utilizing standard robotic tools, to monitor promoter activity of entire microbial genomes in duplicate, or alternatively entire genomes of different microbes on the same array. The output of the assay is a grayscale image and is compatible with commercial products for image analysis and data analysis developed specifically of DNA microarray technologies.

Briefly, the assay involves creating a nonredundant collection of clones containing reporter constructs. These cells are grown to stationary phase and robotically printed at high density onto a porous membrane (e.g., Biodyne B Nunc).

Any contact or non contact printing robot (e.g., Biomek 2000, Beckman) may be used for printing. The membrane is in close contact with solid media. A key aspect of this invention is the ability to move the membrane from one surface to another surface containing different media. The ability to measure the luminescence as a function of regulatory region activity from the cells grown in the solid surface was surprising and unexpected. Previously, LaRossa and Van Dyk (U.S. Pat. No. 6,025,131) reported that the method to detect the activity of regulatory regions as reporter gene activity in suitable hosts was restricted to the cells grown in the liquid media. Growth in solid media allows one to grow the cells to a desired density prior to perturbation then follow the kinetics of the response. Experimental protocols often involve perturbations that prohibit long term exposure due to cell death or other irreversible effects. The ability to move the entire array to new growth conditions allows one a great variety of experimental schemes including, but not limited to pulsed or pulse/chase exposures, reversibility, and short term kinetic studies. Effects of perturbants can be determined by comparison of luminescence generated by treated and control cultures.

Several important characteristics of the assay system needed to be evaluated. In particular, growth density and conditions, sensitivity, reproducibility, and the ability to perturb the reporters and detect changes were major focus points.

Figure 4A:
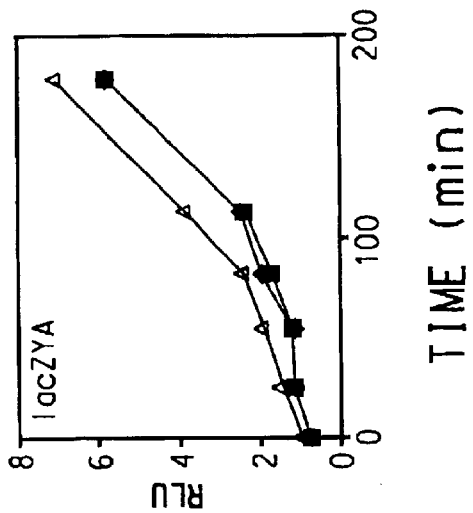
FIG. 4A represents results from strains containing the parental plasmid and two non-responding reporters, osmY, and lacZYA
Figure 4B:
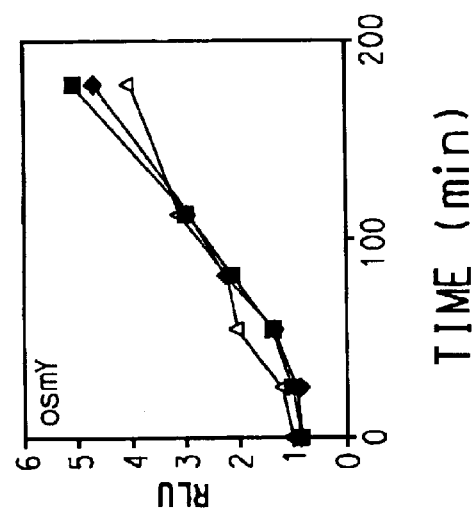
FIG. 4B represents the results from three DNA damage responsive reporters, uvrA, recA, dinG.
Figure 4C:
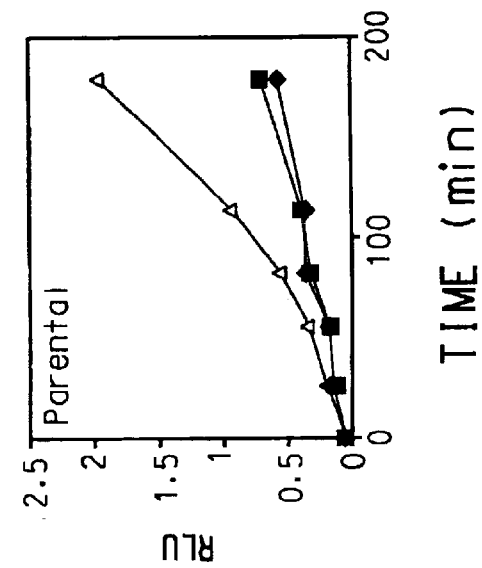
FIGS. 4 (A–D) describes generally the Luxarray 0.5 perturbation with nalidixic acid (NA).
Figure 4F:
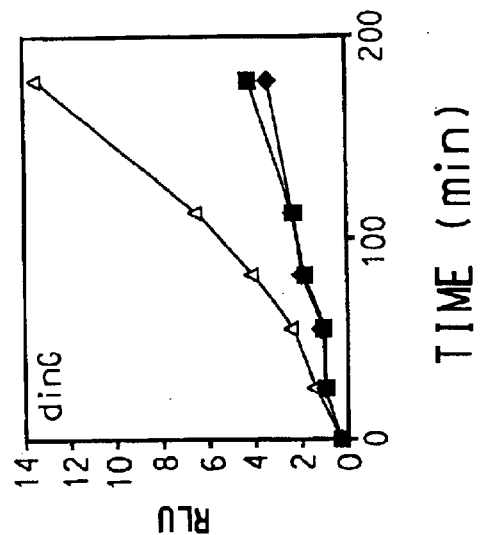
Figure 4E:
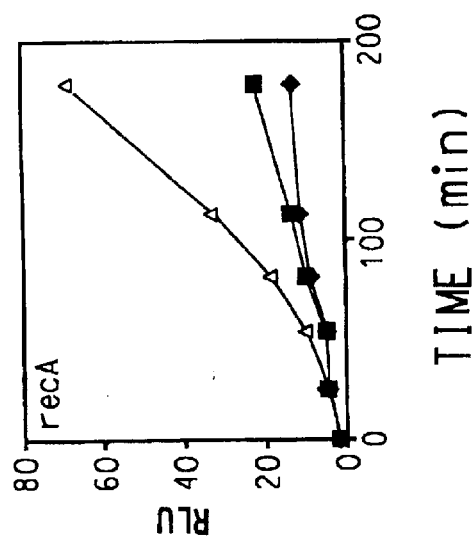
Figure 4D:
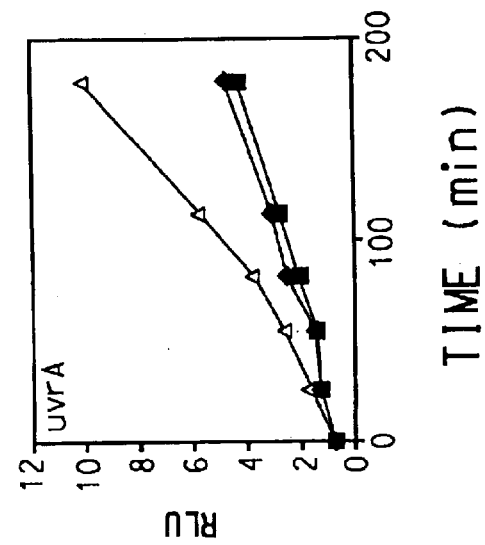
Figure 5B:
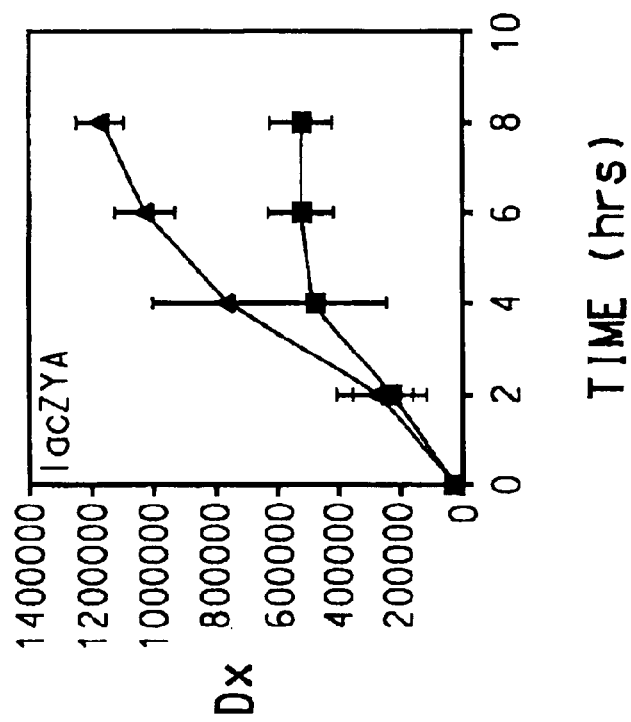
FIG. 5 describes High density Luxarray 0.5 perturbation with nalidixic acid. The squares represent reporter gene response from nalidixic acid treated cultures and the circles represent reporter gene activity from untreated cultures.
Figure 5A:
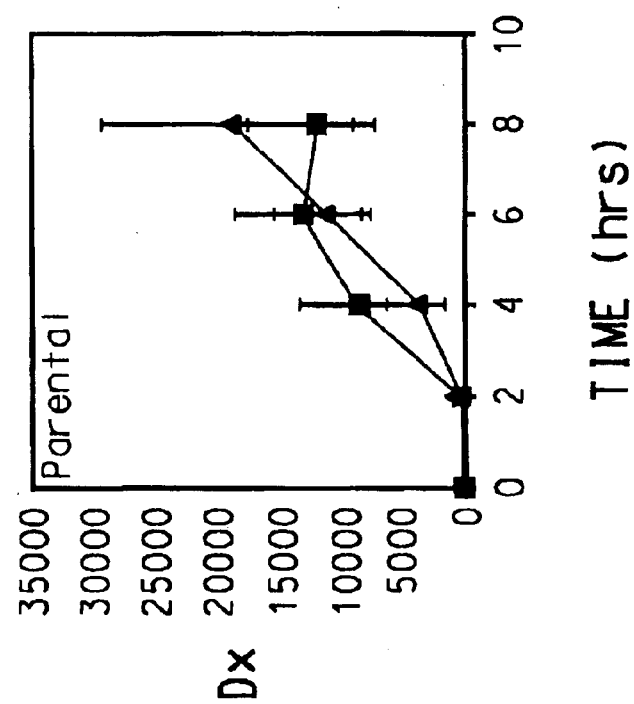
Figure 5D:
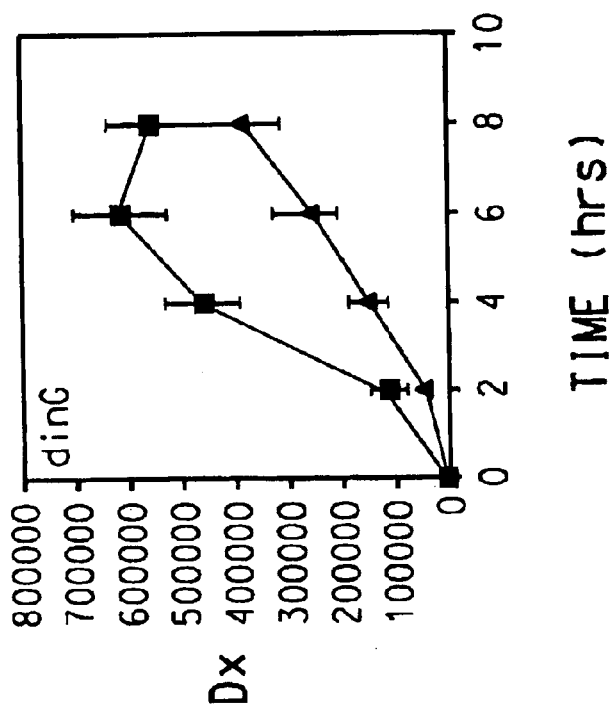
Figure 5C:
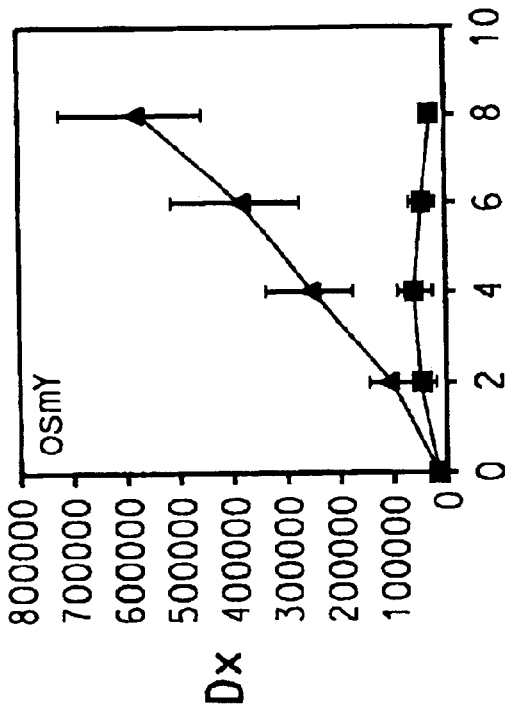
Figure 5F:
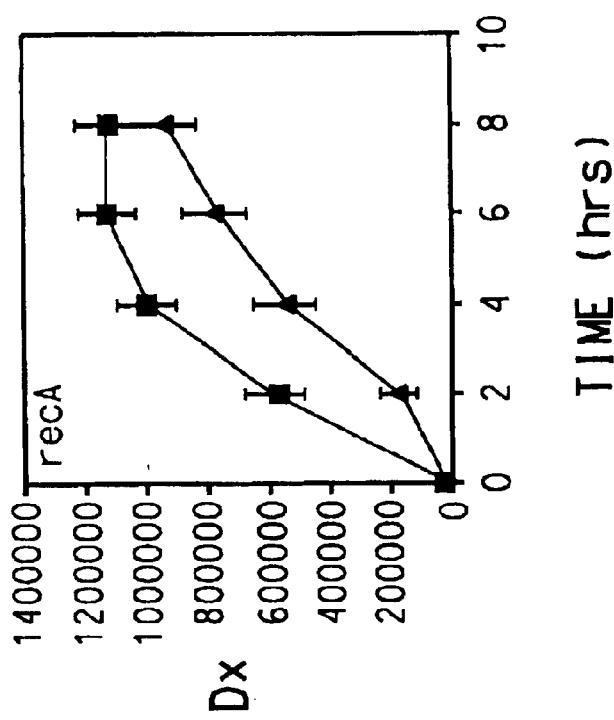
Figure 5E:
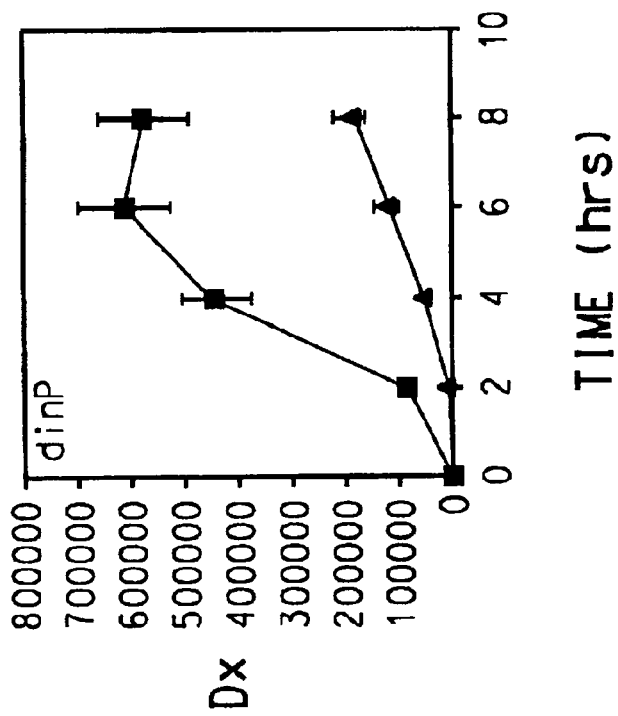

Using DNA damage in *E. coli* as a model system, the assay was first developed with a small set of well characterized clones to evaluate the robustness of the approach. The set of 10 clones were tested for the response to DNA damaging agent, nalidixic acid. The expected nalidixic induced upregulation of genes in the SOS regulon was detected as increased bioluminescence (FIG. 4B). The level of bioluminescence from the strains containing fusions to genes that are not responsive to DNA damage were not affected by the nalidixic acid treatment (FIG. 4A).

The clone set of Luxarray 0.5 was used to develop a highly parallel solid phase assay by printing the clones at high density. This invention allows collection of an image of the signal generated from reporter constructs such that the signal intensity can be subsequently quantified. This requires not only that the collection parameters (focal plane, magnification, integration time, and algorithm) are constant but also that the downstream image analysis software has the ability to process the images generated. Chemical perturbation, one of the utility of this invention, requires physically relocating a membrane from one culture plate to another. This results in images with minimal X-Y positional registration. Several commercially available products can efficiently process these images. ArrayVision™ (Imaging Research, Toronto, Canada) and ImageQuant (Molecular Dynamics, Sunnyvale, Calif.) are two examples of appropriate software packages. It is preferred that a cooled CCD camera is used to capture the data.

Computational filters were applied to the genome-registered clone collection to generate a nonredundant set of reporter constructs representing approximately 28% of the promoters in the genome. Even at this level of coverage, it is likely that at least one representative promoter of all the regulons in *E. coli* is present in the collection. This large set was used in DNA damage perturbation experiments to confirm the response of several promoters. As found with the low density experiments quantified with the luminometer, the expected responses for each clone were well demonstrated. The five documented DNA damage-responsive reporter constructs clearly show an upregulation of expression. In contrast, light production from the strain carrying the lac promoter fusion as well as several strains carrying other promoter fusions was decreased.

A high density cellular array (Lux array 1.0) in this invention was also used to identify a number of putative previously unknown DNA damage-responsive operons. When treated with the DNA damaging chemical, nalidixic acid, in addition to the expected promoter activity (i.e., SOS regulon), several previously undescribed promoters demonstrated a similar behavior. This invention can be used to monitor transcriptional changes in high throughput manner.

This invention also provides a method to identify the fusions that would be useful except that the orientation of the chromosomal DNA is inverted relative to the reporter genes, such that the promoter regions of interest are not operably linked to the reporter genes. Selecting such fusions and inverting the orientation of the insert DNA can significantly enhance the utility of a sequenced collection by adding many more operable linked fusion to the collections. A simple way to do this is to digest the plasmid DNA with a single restriction enzyme that cuts just outside the cloned region and religate the pieces. Although a mixture of plasmids results from this procedure, in many cases the correctly oriented plasmid can be found because cells containing it, but not other possible products, will produce light. This inverting method was also used to add gene fusions to the Lux-A Collection. Other methods besides light production can be used (notably PCR) to identify the orientation or size of the insert.

Additionally, specific PCR primers can be designed for any region of interest on the chromosome for which sequence data is available. For *E. coli* the entire genome is available. Therefore by utilizing positional and directional coordinates for known and predicted promoters, specific primers were designed for the purpose of generating a PCR product containing each promoter. The actual promoter was assumed to lie in a 400 basepair genomic fragment ending at the translational start codon position of the first open reading frame in the operon. Primer pairs were selected from this region for each operon such that the "right" primer was forced to include the start codon of the first open reading frame of the operon (Primer3, Rozen and, Skaletsky (1996, 1997, 1998). Code available at http://www-genome.wi.mit.edu/genome_software/other/primer3.html). Acceptable PCR primer pairs were identified for 80% of the operons using the default Primer3 parameters with an optimal melting temperature, Tm, of 68° C. Primer pairs for the remaining operons can be identified by either relaxing one or more parameters, expanding the search area or by using a different algorithm. The final version of the primers also includes addition of appropriate EcoRI and SacI endonuclease cleavage sites (left and right primers respectively) such that the PCR products can be directionally cloned into pDEW201.

Still other methods to generate gene fusions for a genome-registered collection result in chromosomal rather than plasmid-borne gene fusions. Transposable genetic elements carrying reporter genes can be used to generate gene fusions. If this is done by random transposition into the chromosome of the host organism, the subsequent gene fusions can be genome-registered with respect to the chromosomal DNA sequence by determining the sequence of the junction between the transposable element and the hromosome (Nichols et al., (1998) *J. Bacteriol.* 180:6408–6411). Alternatively, transpositions done in vitro using a defined (and thus genome-registered) segment of chromosomal DNA can be recombined by homologous recombination into the host chromosome. Furthermore, gene fusions formed in vitro by other methods, such as clones in plasmid DNA, can be recombined into the chromosome of the host by homologous recombination (Balbas et al., (1996) *Gene* 172:65–69; Lloyd and Low (1996) In *Escherichia coli* and Salmonella: Cellular and Molecular Biology. ASM Press, pp 2236–2255), site specific recombination (Nash H. (1996) In *Escherichia coli* and Salmonella: Cellular and Molecular Biology. ASM Press, pp 2363–2376) or both (Boyd et al., (2000) *J. Bacteriol.* 182:842–847).

The preferred methods to generate gene fusions include are but not limited to the use of plasmid DNA from clones requiring reorientation as template for the PCR to generate inversion, use of specific PCR primers when sequence data is available, or use of transposition to generate gene fusions in chromosome (Kenyon and Walker (1980) *Proc. Natl. Acad. Sci. U.S.A.* 77:2819–2823). The most preferred method to generate genomic fragments is using restriction enzyme or physical shearing. The genomic fragments are then ligated to promoterless reporter gene to generate gene fusion. The above methods to generate fusions are well known in the art.

This invention also provides a method to use the genome registered collection of gene fusions in a liquid format to discover gene fusions useful as biosensors. For example, 39 gene fusions were found to be upregulated when exposed to limonene for 135 minutes (Example 7). By use of these gene fusion in a strain to be used as the production organism for limonene, the presence of limonene, or the optimum conditions for the limonene production can be measured by the upregulation of bioluminescence.

Gene expression profiles yield useful information relevant to understanding gene function and modes of chemical action. Likewise, such information can be gained by analysis of genetic alterations resulting in loss of function, reduced levels, or over-expression of gene products. Thus, an "array of arrays" can be used to enhance both mode of action studies and functional genomics. Flow diagrams I and II depict two ways such arrays of arrays can be used.

Flow diagram I represents the several tests can be performed on a given perturbation that changes the environment of the cell.

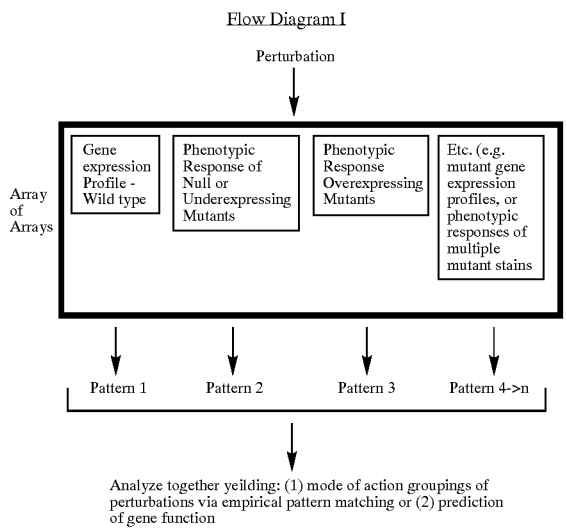

Flow diagram II describes that as data from arrays of arrays is analyzed, altered responses of interest can be further analyzed by selected tools in the array of arrays.

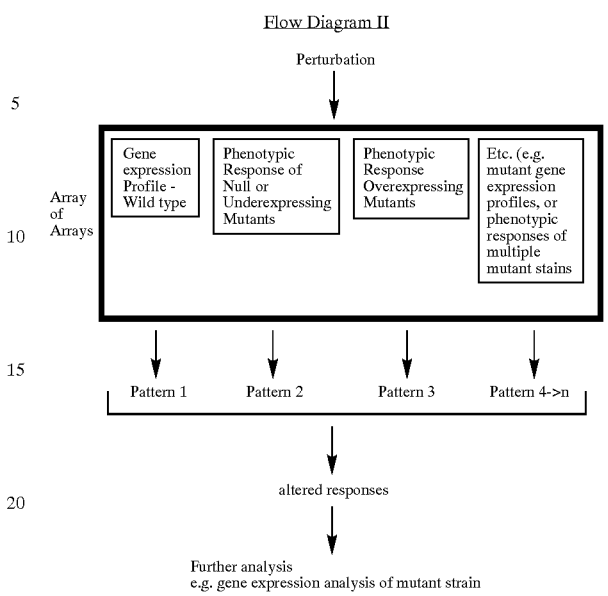

These arrays of arrays can be built by generating large collections of genome-registered mutations in genes of an organism. Several methods are available including but not limited to classical radiation and chemical induced mutagenesis as well as more modern genomic-based techniques including random in vivo transposition followed by sequencing of junctions to determine the gene disrupted, targeted in vitro transposition into individual genes followed by homologous recombination in vivo to generate disruptants, and primer oligonucleotide generated deletion insertion alleles generated in vitro by PCR and subsequently recombined into the genome. Spontaneous mutants can also be selected by a variety of methods (LaRossa, R. A. (11996) In *Escherichia coli* and Salmonella: Cellular and Molecular Biology. ASM Press, p. 2527–2587.). Likewise, a large collection of genome-registered genetic alterations that result in over-expression can be generated. This can be accomplished in several ways including but not limited to genetic selection (LaRossa, R. A. (1996), In *Escherichia coli* and Salmonella: Cellular and Molecular Biology. ASM Press, p. 2527–2587), cloning on multicopy plasmids, placement of the gene to be over-expressed behind a strong promoter, and placement of the gene to be over-expressed behind a regulated promoter.

Perturbations are any alteration of environment or genotype. Perturbations that change the environment include but are not limited to physical properties, such as radiation fluence, radiation spectrum, humidity, substratum, or temperature; nutritional properties, such as carbon source, energy source, nitrogen source, phosphorus source, sulfur source, or trace element sources; biological properties, such as presence of competitors, predators, commensals, pathogens such as phage and other viruses, the presence of toxins, or bacterocins; and chemical properties, such as presence of chelators, inhibitors, toxicants or abnormal levels of normal metabolites.

Several tests can be performed on a given perturbation that changes the environment of the cell (Flow Diagram I). Responses include patterns of gene expression (e.g., reporter gene expression, presence or absence of specific protein or intermediates) and phenotypic effects of genetic alterations; these responses can be analyzed concomitantly. Examples of phenotypes that may be screened for in the present method include but are not limited to metabolic capacity (e.g., carbon source requirement, auxotroph requirement, amino acid requirement, nitrogen source requirement, and purine requirement); Resistance to inorganic chemicals (e.g., acid, arsenate, azide, heavy metals, and peroxide); Resistance to organic and biological chemicals (e.g., antibiotics, Acridine, actinomycin, amino purine, amino phenylalanine, colicin, ethanol, fluoroacetate, mitomycin C, and nalidixic acid); Resistance to biological agents (e.g., phages); Resistance to physical extremes (e.g., temperature, pH, osmotolerance and radiation). The phenotypes amenable to detection by the present invention are numerous and a full review may be found in, Robert LaRossa: *Escherichia coli and Salmonella: Cellular and Molecular Biology* (1996) ASM press p. 2527–2587). This will yield an enhanced empirical matching of one perturbation to another. For instance if one chemical yields a very similar pattern of effects in all tests to another chemical, then the likelihood of a similar mode of action of the two chemicals is high. Secondly, such concomitant analysis of several patterns will enhance understanding of gene function. For example, if a group of genes is regulated similarly by environmental perturbation and genetic perturbation (i.e., mutation) in this group of genes have similar phenotypic effects, then similar function can be hypothesized.

Flow Diagram II depicts that as data from arrays of arrays is analyzed, altered responses of interest can be further analyzed by selected tools in the array of arrays. For example, one can evaluate any perturbation by asking which mutants are hypersensitive or hyper-resistant to the environmental change. Look at the gene expression profile of wild type and the altered mutants in response to the environmental change and in its absence. Another approach to examine genetic changes is to compare the genome-registered collection of mutants to the wild type by examining how growth characteristics vary between the mutants and wild type with changes in a wide range of environmental parameters. Differences of interest are then followed up with gene expression profiling.

As arrays of arrays are utilized, the massive amount of data on phenotypes, which results from interactions between genotypes and the environment and found by changing either the genetic composition or the culture conditions, will allow interpretation of the interplay between mutants and gene expression profiles. Analysis of such interactions will be also useful for discovery of gene function and determining the modes of chemical action. Furthermore, these analyses may lead to identification of useful targets for pharmaceuticals, antimicrobials, or agrochemicals, development of environmental diagnostic tests, or development of high throughput screen based on modes or sites of chemical action.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "KB" means kilobase(s) "hr" means hour(s), "min" means minute(s), "sec" means second(s), "d" means day(s), "ml" means milliliter(s), "$\mu$l" means microliter(s), "nl" means nanoliter(s), "$\mu$g" means microgram(s), "ng" means nanogram(s), "mM" means millimolar, "$\mu$M" means micromolar.

Media and Culture Conditions:

Materials and methods suitable for the maintenance and growth of bacterial cultures were found in *Experiments in Molecular Genetics* (Jeffrey H. Miller), Cold spring Harbor Laboratory Press (1972), *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, D.C. or Thomas D. Brock in *Biotechnology: A Textbook of Industrial Microbiology*, Second Edition (1989) Sinauer Associates, Inc., Sunderland Mass. All reagents and materials used for the growth and maintenance of bacterial cells were obtained from Aldrich Chemicals (Milwaukee, Wis.), DIFCO Laboraoties (Detroit, Mich.), Gibco/BRL (Gaithersburg, Md.), or Sigma Chemical Company (St. Louis, Mo.) unless otherwise specified.

LB medium contains following per liter of medium: Bacto-tryptone (10 g), Bacto-yeast extract (5 g), and NaCl (10 g).

Vogel-Bonner medium contains the following per liter: 0.2 g $MgSO_{40} \cdot 7H_2O$, 2 g citric acid. 1 $H_2O$, 10 g $K_2HPO_4$ and 3.5 g $NaHNH_4PO_4 \cdot 4H_2O$.

Minimal M9 medium contains following per liter of medium: $Na_2HPO_4$ (6 g), $KH_2PO_4$ (3 g), NaCl (0.5 g), and $NH_4Cl$ (1 g).

Above media were autoclaved for sterilization then 10 ml of 0.01 M $CaCl_2$ and 1 ml of 1 M $MgSO_{40} \cdot 7H_2O$ were added to M9 mediums. Carbon source and other nutrient were added as mentioned in the examples. All additions were pre-sterilized before they were added to the media.

Molecular Biology Techniques:

Restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR) techniques were found in White, B., *PCR Protocols: Current Methods and Applications*, Volume 15(1993) Humana Press Inc.

Example 1

Construction Sequencing and Registering a Random Library of *E. coli* Genomic Fragments Fused to a luxCDABE Reporter The random library of *E. coli* genomic fragments in plasmid pDEW201, which contains the origin of replication and bla from pBR322, four transcription terminators upstream of the promoterless *P. luminescens* luxCDABE genes, and a multiple cloning site that lies between the terminators and luxCDABE were constructed as previously described (Van Dyk et al., (1998) *J. Bacteriol.* 180:785–792;

Van Dyk and LaRossa (1998) Methods in Molecular Biology: Bioluminescence, Methods and Protocols, Humana Press Inc. vol. 102:85–95).

Briefly, chromosomal DNA isolated from *E. coli* strain W3110 (Ernsting et al., (1992) *J. Bacteriol.* 174:1109–1118) was partially digested with the restriction enzyme Sau3A1, size fractionated by agarose gel electrophoreses, and a fraction with an average size of approximately 1.8 KB isolated. This fraction was ligated to pDEW201 that had previously been digested with BamHI and treated with calf intestinal alkaline phosphatase. The ligation products were used to transform ultracompetent *E. coli* XL2Blue cells (Stratagene) to ampicillin resistance using the protocol provided by Stratagene. Preliminary characterization of individual XL2Blue transformants that were picked in random indicated that a large percentage (16 of 16) contained insert DNA with sizes ranging from 0.9 to 3.0 KB. Approximately 24,000 of these transformants were pooled and used as a source of heterogeneous plasmid DNA isolated using Qiagen tip20 columns (Qiagen Corp). This plasmid DNA pool was used to transform *E. coli* DPD1675 (Nishimura et al. (1990). Nucleic Acids Res. 18:6169; Van Dyk and LaRossa (1998) Methods in Molecular Biology: Bioluminescence Methods and Protocols, Humana Press inc. vol. 102:85–95) selecting for ampicillin resistance and using a 30 minute phenotypic expression time to minimize the presence of siblings. A total of 8066 individual transformants were used to inoculate the 96-wells of sterile Microtest III™ Tissue Culture Plates (Falcon®) each containing 190 $\mu$l of Vogel-Bonner medium (Davis et al., (1980) Advanced bacterial genetics. Cold Spring Harbor Laboratory, Cold Spring Harbor, N.Y.) with glucose as a carbon source and supplemented with thiamine, uracil, proline, and 25 $\mu$g/ml of ampicillin. These plates were covered and incubated overnight without shaking at 37° C. The overnight cultures in 96-well plates were used for permanent cryogenic storage in duplicate at −80° C. (Menzel, R., (1989) *Anal. Biochem.* 181:40–50). These 8066 individual cultures are called the Lux-A Collection.

For DNA sequence analysis, one of the duplicate sets of the Lux-A Collection was thawed and used as an inoculum for cultures grown to saturation in Terrific Broth (Gibco-BRL, Inc) containing 100 $\mu$g/ml ampicillin in 96 well deep-well plates. Plasmid DNA was extracted from the cultures using the Qiagen R.E.A.L.™ prep method with the following modification: after lysis of cells, the plates were placed in a boiling water bath for 5 minutes and then rapidly chilled in an ice-water bath before precipitation with Buffer 3. This modification prevented degradation of the plasmid DNA by the nucleases present in the non-end A host strain, DPD 1675. DNA sequencing reactions were performed with approximately 11 $\mu$g of plasmid DNA under standard ABI Prism™ DyeTerminator Reaction Ready conditions with the primers pDEW201.forward (SEQ ID NO: 1, 5'-GGATCGGAATTCCCGGGGAT-3') and pDEW20.reverse (SEQ ID NO:2, 5'-CTGGCCGTTAATAATGAATG-3') to obtain sequence information from each end of the insert. DNA sequences were determined on ABI377™-XL 96-lane upgraded Sequencers under 4x run conditions on 5% PAG (polyacrylamide gel) LongRanger™ (FMC, Inc.) gels and analyzed with ABI software. DNA sequences were transferred to a UNIX based utility for further analysis. A homology search for the sequence from the beginning and end of each Lux-A clone (in both orientations) was performed against the complete *E. coli* sequence (Genbank accession U00096) using Pearson's FASTA program (fasta3, Version 3.1t13). The essential Fasta options were -nQH-m 10-z 0.

The essential data about each highly significant alignment (FASTA score>1000, minimum overlap length>200, and minimum identity>70%) was stored in a relational database (Sybase System 11, Sybase Inc.).

The location of Lux-A clone on the *E. coli* genome was then based on the above computed homologies for both the beginning and end of the insert, using the following rules:

i) Both distal and proximal ends of the insert must have an unambiguously high sequence homology with *E. coli*, ii) the relative location and orientation of the matches of the sequence determined from the beginning and end of the clone implied a reasonable length for the clone, which were known to fall in a fairly narrow distribution.

In many cases the above procedure gave a single probable location, but in others there were multiple possible locations. The results were stored in the relational database.

A table of open reading frame annotations for *E. coli* was downloaded using NCBI's Entrez facility, and this data was stored in the relational database.

A web based, tabular interface to the data was created. This allows one to see the Lux-A clones in relation to the functional annotation. A Java based graphical interface was also created to make positional and directional relationships easy to visualize. Thus the Lux-A Collection was registered to the *E. coli* genome.

Example 2

Validation of Lux-A Collection by Verification of Selected Global Regulatory Responses With the sequencing of Lux-A Collections and registering of the majority of the LuxA members, it was possible to further examine the biological responses of strains containing luxCDABE fusions to other members of well-characterized regulatory circuits. Gene fusions to the lac operon, and members of the heat shock, SOS, SoxRS, and OxyR regulons were selected from the Lux-A Collection and the responses to known inducers of each of these global regulatory circuits were tested.

Growth Media and Chemicals.

A rich liquid medium, LB (Miller, J. H., (1972) Experiments in molecular genetics. Cold Spring Harbor Laboratory Press, Cold Spring Harbor, N.Y.), was used. When specified, ampicillin (Amp) was added at 150 $\mu$g/ml. Ethanol (200 proof, Quantum Chemicals) was diluted directly into LB medium. A stock solution of 20 mg/ml nalidixic acid (Sigma Chemical Co.) in 1 M NaOH was further diluted into LB medium. Likewise, a stock solution of 100 mg/ml methyl viologen (Sigma Chemical Co.) in water was further diluted into LB medium. A 30% solution of hydrogen peroxide (EM Science) was diluted into LB medium to the desired concentrations.

Re-Isolation from Microplates, Growth of Cultures and Testing Stress Responses.

Selected strains were reisolated from the Lux-A Collection microplates stored at −80° C. by streaking for single colonies on LB-Amp plates. The purity of the cultures in the wells was tested by inoculating four single colonies into 100 $\mu$l of LB medium in a 96 well luminometer plate (Microlite, Dynex Technologies). Consistent bioluminescence of each set of four isolates provided evidence of clonal purity.

To test the stress responses, one or two single colonies of each selected strain were used to inoculate 5.0 ml of LB medium containing 150 $\mu$g/ml of ampicillin. These cultures were grown overnight at 37° C. then diluted by adding 50 μl 3or 100 μl of the overnight culture into 10.0 ml of fresh LB medium (without ampicillin) and grown with agitation at 37° C. until the culture was in exponential phase with readings on a Klett-Summerson colorimeter containing the red filter of between 10 and 40. These actively growing cultures were immediately used to initiate a stress response experiment by adding 50 μl of cultures to 50 μl of LB medium containing various concentrations of chemical in the wells a 96 well luminometer plate. This division of the actively growing culture at the time of chemical addition ensured identical populations were present when the stress was imposed. Light production was measured in a Dynex ML3000 luminometer at 37° C. The dimensionless units of light production, relative light units (RLU), are obtained by comparison with the light reading from an internal light-emitting diode. The cycle mode of the ML3000 luminometer, similar to previous descriptions (Van Dyk et al., *Appl. Environ. Microbiol.* 60:1414–1420) was used.

Gene Fusions to the lacZYA Operon.

Transcription of the very well characterized lac operon is regulated by both specific and global regulatory circuits. Specific, negative regulation is mediated by the lacI-encoded repressor (Choy and Adhya, (1996) In *Escherichia coli* and Salmonella: Cellular and Molecular Biology. ASM Press pp 1287–1299). Global regulation in response to glucose availability is mediated by positive transcriptional activation of cAMP-CRP (Botsford and Harman (1992) Cyclic AMP in prokaryotes. *Microbiol Rev.* 56:100–122). The Lux-A Collection contains three members that are fusions of luxCDABE to the lac operon as shown in FIG. 1. To test for the appropriate response of these gene fusions to glucose, each was reisolated and tested for bioluminescence when grown in the presence or absence of glucose in LB medium. The results are shown in Table 2.

TABLE 2

Fusions to the lac operon in the Lux-A Collection.
RLU of 100 μl overnight cultures

| Lux Clone | LBAmp[150] + 0.4% glucose | LBAmp[150] |
|---|---|---|
| lux-a.pk034.a6 (a) | 0.002 | 23.0 |
| lux-a.pk034.a6 (b) | 0.001 | 18.8 |
| lux-a.pk050.b9 (a) | 0.001 | 26.0 |
| lux-a.pk050.b9 (b) | 0.001 | 0.007 |
| lux-a.pk065.d4 (a) | 0.001 | 19.1 |
| lux-a.pk065.d4 (a) | 0.001 | 19.6 |

Two isolated single colonies of each culture were tested by growing overnight in the specified medium then measuring the bioluminescence of 100 μl in an ML3000 luminometer. LBAmp medium is LB medium containing ampicillin at 150 mg/ml concentration.

With one exception, each of the isolated colonies from the cultures in the Lux-A Collection was much more highly bioluminescent in the absence of glucose than in its presence. One colony from the lux-a.pk050.b9 that was not highly bioluminescent might be due to contamination of the culture in that well. Other putative cross contamination events have not been observed. Each of the lacZ-luxCDABE fusion strains had at least one reisolated colony that gave the expected response to glucose. Thus, the appropriate biological response of these Lux-A Collection members was verified.

Heat Shock Regulon Gene Fusions.

The Lux-A Collection was examined to find fusions to genes in the $\sigma^{32}$-controlled heat shock regulon (Gross, C. A., (1996) In *Escherichia coli* and Salmonella: Cellular and Molecular Biology, Second ed. ASM Press, pp. 1382–1399). Table 3 shows the genes or operons for which the Lux-A Collection was searched and the number of gene fusions found for each gene.

TABLE 3

Lux-A Collection Gene Fusions
to Heat Shock Regulon members

| Heat shock gene or operon | Number of Fusions in the Lux-A Collection |
|---|---|
| grpE | 0 |
| lon | 1 |
| clpPX | 0 |
| dnaKJ | 0 |
| groESL (mopAB) | 0 |
| rpoD | 3 |
| htpG | 0 |
| clpB | 1 |
| htpX | 0 |
| htgA (htpY) | 0 |
| hslT (ibpA) | 0 |
| rfaDFCL (htrM) | 1 |

While there was not complete representation of the each member of the heat shock regulon, lux fusions to four of twelve heat shock promoter (33%) were found. Thus, the Lux-A Collection contains members that should report on activation of this stress response. In addition, strains with the previously constructed grpE-luxCDABE gene fusion in parental plasmid pDEW201 (Van Dyk et al., (1998) *J. Bacteriol.* 180:785–792) had been placed in selected wells of the Lux-A Collection plates as a control. One of these was also selected for testing. Table 4 summarizes the information on the six strains that were reisolated from wells of the frozen Lux-A Collection.

TABLE 4

Heat shock regulon gene fusions

| Lux clone | Strain name | insert size | fusion to: | Genes in cloned DNA | Basal RLU* | 3% Ethanol Response ratio# |
|---|---|---|---|---|---|---|
| lux-a.pk057.h1 | DPD2241 | 581 | grpE | yfjB' grpE' | 61.1 | 5.2 |
| lux-a.pk021.g11 | DPD2242 | 2154 | lon | 'clpP clpX lon'[1] | 6.71 | 5.6 |
| lux-a.pk089.e7 | DPD2246 | 1989 | rpoD | 'dnaG rpoD'[2] | 9.49 | 2.4 |
| lux-a.pk054.c3 | DPD2243 | 2319 | clpB | 'sfhB yfiH clpB'[3] | 38.5 | 4.7 |
| lux-a.pk040.e4 | DPD2244 | 2650 | rfaDFCL | yibB' rfaD rfaF' | 33.1 | 1.4 |

*From zero time point of control (untreated) actively growing cultures in Vogel-Bonner minimal medium that had been obtained during the screen for sulfometuron methyl responses (Van Dyk et al., J. Bacteriol. 180: 785–792).
The ratio of the bioluminescence from the culture treated with 3% ethanol at 40 minutes after ethanol addition to LB divided by the bioluminescence of the untreated control in LB at the same time point.
[1]clpP and clpX are cotranscribed; thus, there is not expected to be a promoter upstream of clpX.
[2]This fragment should contain only the rpoD specific promoter (Tylor et al., (1984) Cell 38: 371–381)

TABLE 4-continued

Heat shock regulon gene fusions

| Lux clone | Strain name | insert size | Genes in cloned fusion to: | Basal DNA RLU* | 3% Ethanol Response ratio# |
|---|---|---|---|---|---|

³There is no intergenic space between sfhB and yfiH, thus there is unlikely to be a promoter upstream of yfiH.
The mark ('or') is used to designate that the *E. coli* gene in the chimeric reporter gene fusion is truncated.
If the ' is at the start of the gene name (e.g. 'lacZ), it means the 5' end is missing.
If the ' is at the end of the gene (e.g. lacZ') it means the 3' end of the gene is not present.

The light production from each of these strains in the absence of stress is consistent with each of these chromosomal DNA fragments containing an active promoter because these values are much greater than that from a culture carrying the parental plasmid pDEW201, which had 0.002 RLU under the same conditions (Van Dyk et al., (1998) *J. Bacteriol.* 180:785–792). These strains were tested for their ability to report on the heat shock stress response by using 5, 4, 3, and 2 (v/v)% ethanol, a known, potent chemical inducer. For each of the six strains, at least two concentrations of ethanol resulted in increased bioluminescence as compared with the control, untreated culture. Table 4 contains the response ratio for each strain to 3% ethanol at 40 minutes of treatment. These data demonstrate that these heat shock regulon gene fusions from the Lux-A Collection report the induction of the heat shock response.

SOS Regulon Gene Fusions.

In a like fashion as described above, the Lux-A Collection was examined to find fusions to genes in the SOS DNA damage response regulon (Kim et al., (1997) *Proc Natl Acad Sci USA* 94(25):13792–7; Walker, G. C. (1996) In *Escherichia coli* and Salmonella: Cellular and Molecular Biology. ASM Press pp. 1400–1416). Table 5 shows the genes or operons for which the randomly generated Lux-A Collection was examined and the number of gene fusions present for each gene.

TABLE 5

Quantities of Lux-A Collection
Gene Fusions to SOS Regulon members

| SOS gene or operon | Number of Fusions in the Lux-A Collection |
|---|---|
| umuDC | 0 |
| recA | 2 |
| uvrA | 1 |
| uvrB | 0 |
| sulA (sfiA) | 0 |
| uvrD | 1 |
| recN | 0 |
| polB (din A) | 0 |
| dinP (dinB) | 1 |
| dinD | 0 |
| dinF | 1 |
| dinG | 1 |
| dinI | 0 |
| ruvAB | 1 |

Of the fourteen SOS regulon genes or operons examined, seven (50%) were found to be represented by useful fusions in the Lux-A Collection. Thus, this collection contains members that should report on activation of the SOS stress response. Table 6 summarizes the information on the eight strains that were reisolated from wells of the frozen Lux-A Collection.

TABLE 6

SOS regulon gene fusions

| Lux clone | Strain name | insert size | fusion to: | Genes in Insert DNA | Basal RLU* | Nalidixic acid response ratio# |
|---|---|---|---|---|---|---|
| lux-a.pk085.a5 | DPD2247 | 2840 | dinF | plsB(−)' dgkA(+) lexA(+) dinF(+)' | 0.224 | 2.2 |
| lux-a.pk0024.f5 | DPD2248 | 2022 | dinG | 'rhlE(+) ybiA(−) dinG(+)' | 32.8 | 2.0 |
| lux-a.pk055.a3 | DPD2249 | 2125 | dinP | fhiA(−)'mbhA(+) dinP(+)' | 4.41 | 5.0 |
| lux-a.pk022.d4 | DPD2250 | 1789 | recA | 'mtlB(−) ygaD(−) recA(−)' | 97.5 | 1.8 |
| lux-a.pk085.b5 | DPD2251 | 1782 | recA | 'mtlB(−) ygaD(−) recA(−)' | 99.5 | 2.8 |
| lux-a.pk01.b6 | DPD2253 | 2105 | uvrA | yjcC(+)' yjcB(−) ssb(+) uvrA(−)' | not done | 1.4 |
| lux-a.pk052.b6 | DPD2254 | 1632 | uvrD | 'xerC(+) yigB(+) uvrD(+)' | 15.7 | 1.2 |
| lux-a.pk058.f2 | DPD2293 | 1890 | ruvA(−) | 'yebC(−) ruvC(−) yebB(+) ruvA(−)' | 14.3 | 4.6 |

*From zero time point of control (untreated) actively growing cultures in Vogel-Bonner minimal medium that had been obtained during the screen for sulfometuron methyl responses (Van Dyk et al., (1998) J. Bacteriol. 180-78–792).
The ratio of the bioluminescence from the culture treated with 5 μg/ml of nalidixic acid at 110 minutes after nalidixic acid addition to LB divided by the bioluminescence of the untreated control in LB at the same time point.
The mark ('or') is used to designate that the *E. coli* gene in the chimeric reporter gene fusion is truncated.
If the ' is at the start of the gene name (e.g. 'lacZ), it means the 5' end is missing.
If the ' is at the end of the gene (e.g. lacZ') it means the 3' end of the gene is not present.

Each of these strains that were tested for basal bioluminescence in defined medium had a greater level of light production than did a strain containing the parental plasmid, indicating the presence of a promoter driving expression of the luxCDABE reporter. The ability of these promoter-luxCDABE fusions to report activation of the SOS stress response was tested using nalidixic acid, a known, potent chemical inducer. The final concentrations of nalidixic acid were 1, 5, 25, and 125 μg/ml for all but strain DPD2293, which was tested at 80, 40, 20, 10, 5, 2.5, and 1.25 μg/ml. For each of the eight strains, at least three concentrations of nalidixic resulted in increased bioluminescence. Table 6 gives the response ratio to 5 μg/ml of nalidixic acid at 110 minutes after addition. These data demonstrate that induction of the SOS response is reported by increased bioluminescence for these SOS regulon gene fusion in the Lux-A Collection.

Specificity of responses was tested by measuring the effect of ethanol on these SOS regulon gene fusions. In each case there was little to no increased bioluminescence induced by 5, 4, or 3% (v/v) ethanol treatment. For example, the treatment with 3% ethanol at 40 minutes after addition, a condition which resulted in increased light production from all the heat shock regulon gene fusions (Table 4), for strain DPD2249 containing a dinP-luxCDABE gene fusion yielded a response ratio was 0.80. Similarly, when strain DPD2243 containing a heat shock regulon clpB-luxCDABE fusion was tested with nalidixic acid, no increase in bioluminescence was observed; at 110 minutes after addition of 5 μg/ml nalidixic acid, the response ratio was 0.40. Thus, the specificity of the heat shock response to ethanol and the SOS response to nalidixic acid was shown.

SoxS-Regulated Oxidative Damage Regulon Gene Fusions.

The Lux-A Collection was also examined for the presence of fusions to genes in the SoxR and SoxS regulated oxidative stress response regulon (Koh et al., (1999) *Mol. Gen. Genet.* 261:374–380; Rosner and Storz (1997) *Curr. Top. Cell. Regul.* 35:163–177; Van Dyk et al., (1998) *J. Bacteriol.* 180:785–792). Table 7 below shows results.

TABLE 7

Quantities of Lux-A Collection Gene Fusions to the SoxR/S regulon members

| SoxR/A regulon gene or operon | Number of Fusions in the Lux-A Collection |
|---|---|
| sodA | 0 |
| nfo | 0 |
| fumC | 0 |
| achA | 0 |
| fpr | 0 |
| zwf | 3 |
| micF | 0 |
| acrAB | 0 |
| inaA | 1 |
| pqiAB | 0 |
| ribA | 1 |
| poxB | 1 |

In a similar fashion to the heat shock and SOS regulons, the SoxR/S regulon was not fully represented in the Lux-A Collection. Nevertheless, the collection contained gene fusions to 33% of the SoxR/S regulon gene or operons that would be expected to report on the activation of this stress response. Table 8 summarizes the information on the six strains that were reisolated from wells of the frozen Lux-A Collection.

TABLE 8

SoxR/S regulon gene fusions

| Lux clone | Strain name | insert size | fusion to: | Genes in Insert DNA | Basal RLU* | Methyl viologen response ratio |
|---|---|---|---|---|---|---|
| lux-a.pk053.b1 | DPD2278 | 1708 | zwf | pykA(+)' yebK(+) zwf(−)' | 5.0 | Not tested |
| lux-a.pk082.g7 | DPD2272 | 1708 | zwf | pykA(+)' yebK(+) zwf(−)' | 16.9 | 3.6 |
| lux-a.pk088.e1 | DPD2279 | 1709 | zwf | pykA(+)' yebK(+) zwf(−) | 4.2 | Not tested |
| lux-a.pk078.d2 | DPD2286 | 2308 | ribA | yciM(+)' o102(+) pgpB(+) ribA(−)' | 5.8 | 4.7 |
| lux-a.pk014.a9 | DPD2087 | 1583 | inaA | 'glpQ yhaH inaA' | 9.8 | 9.0 |
| lux-a.pk071.a11 | DPD3509 | 1131 | poxB | 'b0872 poxB' | 1.5 | 15.0 |

*From zero time point of control (untreated) actively growing cultures in Vogel-Bonner minimal medium that had been obtained during the screen for sulfometuron methyl responses (Van Dyk et al., (1998) J. Bacteriol. 180: 785–792).
The ratio of the bioluminescence from the culture treated with 250 μg/ml of methyl viologen at 120 minutes after methyl viologen addition to LB divided by the bioluminescence of the untreated control in LB at the same time point.
The mark ('or') is used to designate that the E. coli gene in the chimeric reporter gene fusion is truncated.
If the ' is at the start of the gene name (e.g. 'lacZ), it means the 5' end is missing.
If the ' is at the end of the gene (e.g. lacZ') it means the 3' end of the gene is not present.

Like the SOS and heat shock regulon fusions, these had basal light production greater than the promoterless parental plasmid indicating the presence of a promoter. Responsiveness of four of these strains to a known inducer of the SoxR/S regulon, methyl viologen, was tested at 1000, 500, 250, 125, 62, 31 and 16 μg/ml. Each of these seven methyl viologen concentrations induced increased bioluminescence from each of the four strains. Table 8 gives the response ratio for 250 μg/ml at 120 minutes of treatment for the four tested strains. Here again, the biologically appropriate response was observed.

OxyR-Regulated Oxidative Damage Regulon Gene Fusions.

Fusions to OxyR regulated genes (Rosner and Storz. (1997) Curr. Top. Cell. Regul. 35:163–177) were found in the Lux-A Collection as summarized in Table 9.

TABLE 9

Quantities of Lux-A Collection Gene Fusions to the OxyR regulon members

| OxyR regulon gene or operon | Number of Fusions in the Lux-A Collection |
|---|---|
| katG | 0 |
| gorA | 0 |
| dps | 0 |
| ahpCF | 3 |

Of these four genes or operons controlled by OxyR, fusions to one (25%) was available in the Lux-A Collection. Table 10 summarizes the information on the three strains, each containing a fusion of the ahpCF operon regulatory region to the luxCDABE reporter, that were reisolated from wells of the frozen Lux-A Collection.

in Environmental Chemical Sensors and Biosensors. ACS Symposium Series). Mutations in this gene result in reduced plasmid copy number for plasmids with origins of replication like that in pBR322 (Lopilato et al., (1986) Mol. Gen. Genet. 205:285–290), thus resulting in reduced basal expression of gene fusions carried on such plasmids. Accordingly, to test if reducing the copy number of the ahpC-luxCDABE fusions would also yield more reliable detection of the OxyR-mediated stress response, plasmid DNA taken from two of these Lux-A Collection strains was moved by transformation into a pcnB⁻ mutant host strain. The two resulting strains were tested for responses to hydrogen peroxide at 0.004, 0.002, 0.001, 0.0005, 0.00025, 0.00012, 0.00006%. Each of these seven concentrations dramatically induced increased bioluminescence from both ahpC-luxCDABE fusion strains in the pcnB⁻ host. The last column of Table 10 gives the response ratio to treatment with 0.002% hydrogen peroxide at 30 minutes. Thus, the appropriate biological response from these fusions to a highly expressed gene was obtained when the copy number of the gene fusion was reduced.

In one instance where the response from the plasmid-borne gene fusion to a highly expressed gene was weak, it was demonstrated that reduction of plasmid copy number with a pcnB mutation resulted in more potent induction.

TABLE 10

OxyR regulon gene fusions

| Lux clone | Strain name | insert fusion size to: | Genes in Insert DNA | RLU initial screen* | $H_2O_2$ response ratio# | $H_2O_2$ response ratio in pcnB- host‡ |
|---|---|---|---|---|---|---|
| lux-a. pk051.d5 | DPD2283 | 1184 ahpC | dsbG' ahpC(+)' | 92.2 | 1.3 | 16.5 |
| lux-a. pk051.e3 | DPD2284 | 1184 ahpC | dsbG' ahpC(+)' | 68.3 | 1.6 | 15.3 |
| lux-a. pk03.d6 | DPD2285 | 1182 ahpC | dsbG' ahpC(+)' | 47.2 | 1.2 | not done |

*From zero time point of control (untreated) actively growing cultures in Vogel-Bonner minimal medium that had been obtained during the screen for sulfometuron methyl responses (Van Dyk et al. (1998) J. Bacteriol. 180: 785–792).
The ratio of the bioluminescence from the culture treated with 0.002% hydrogen peroxide at 30 minutes after hydrogen peroxide addition to LB divided by the bioluminescence of the untreated control in LB at the same time point.
‡The ratio of the bioluminescence from the culture of E. coli host strain DPD2228 [F-lac4169 rpsL pcnB80 zad-2084::Tn10] containing the plasmid DNA from the original Lux-A Collection strain listed treated with 0.002% hydrogen peroxide at 30 minutes in LB after hydrogen peroxide addition divided by the bioluminescence of the untreated control in LB at the same time point.
The mark ('or') is used to designate that the E. coli gene in the chimeric reporter gene fusion is truncated.
If the ' is at the start of the gene name (e.g. 'lacZ), it means the 5' end is missing.
If the ' is at the end of the gene (e.g. lacZ') it means the 3' end of the gene is not present.

The high level of light production from these three strains containing ahpC-luxCDABE gene fusions indicates that they each contained a very active promoter. To test if these strains would report on activation of the OxyR-controlled oxidative stress response, each was treated with hydrogen peroxide at 0.016, 0.008, 0.004, 0.002, 0.001, 0.0005, 0.00025%. At best, the bioluminescence was minimally induced. Table 10 shows the response ratio to treatment with 0.002% hydrogen peroxide at 30 minutes after treatment.

Previously, another luxCDABE fusion in plasmid pDEW201 to a gene in the OxyR regulon, katG had been shown to yield larger response ratios to hydrogen peroxide when the plasmid was moved to an E. coli host strain containing a pcnB mutation (Van Dyk et al., (2000) in press. In A. Mulchandani and O. A. Sadik (ed.), Recent Advances Other fusions to highly expressed genes can also be moved to a host strain with reduced copy number, such a pcnB mutant, or integrated into the chromosome at a gene dosage of one (Elsemore, D. A. (1998) Methods in Molecular Biology: Bioluminescencent Protocols., vol. 102, p:97–104, Humana Press, Inc).

Example 3

Use of a Genome-Registered Collection of Reporter Gene Fusions to Confirm or Question Results from DNA Array Analysis and to Develop High Throughput Screens Based on Gene Expression DNA Microarray Experiment with Mitomycin C (MMC)

The E. coli strain MG1655 (rph-1) was used. Cultures grown in LB at 37° C. overnight were diluted 1 to 250 into fresh LB and grown at 37° C. with aeration. Each subculture was split into two 100 ml cultures when the reading on a Klett-Sammerson calorimeter with the red filter reads 20 Klett units. MMC (Sigma, dissolved in ddH$_2$O) at a final concentration of 250 ng/ml, a sub-lethal dose, was added to one of the split cultures. The other culture was a no addition control. Incubation at 37° C. continued for another 40 minutes, then cells were collected for preparing total RNA. The MMC treated culture and its control reached 60 and 55 Klett units, respectively after 40 minute treatment.

Total RNA purification, first-strand cDNA labeling, preparation of the *E. coli* whole genome high-density microarray chips, hybridization and data analysis were done as previously described (Wei et al. (2001) *J. Bacteriol.* 183: 545–556). Both cy3 and cy5 were used in probe labeling, and the hybridization experiments were repeated by swapping the fluorescence cy dyes between each pair of MMC treated sample and its blank control.

Ratios of expression in the mitomycin C treated samples vs. controls were calculated for all genes in the DNA array. Ratios greater than or equal to 2 were considered induced genes, while those with ratios less than 2 fold were considered uninduced. The known SOS genes (Kim et al., (1997) *Proc Natl Acad Sci USA* Dec. 9, 1997; 94(25):13792–7; Lomba et al., (1997) *FEMS Microbiol Lett* 156:119–122; Walker, G. C. (1996). In *Escherichia coli* and Salmonella: Cellular and Molecular Biology. ASM Press pp.1400–1416) fell into both the induced (Table 11) and uninduced classes (Table 12). In addition, 20 genes not previously known to be induced by MMC were observed to be induced in the array experiment (Table 13).

TABLE 11

Known SOS genes induced by MMC in array experiment

| Gene | Fold induction/ array experiment | Available Lux Fusion | Induction of Fusion |
|---|---|---|---|
| recN | 8.3 | NO | |
| recA | 3.0 | YES | YES |
| lexA | 3.6 | NO | |
| dinI | 6.7 | NO | |
| dinD | 2.2 | NO | |
| uvrA | 2.3 | YES | YES |
| uvrB | 2.1 | NO | |
| ruvA | 2.0 | YES | YES |
| sulA | 5.8 | NO | |
| umuC | 2.1 | NO | |
| dinB (dinP) | 2.0 | YES | YES |
| b1848 (yebG) | 5.8 | NO | |

TABLE 12

Known SOS genes NOT induced by MMC in array experiment

| Gene | Fold induction/ array experiment | Available Lux Fusion | Induction of Fusion |
|---|---|---|---|
| uvrD | 1.4 | YES | YES |
| polB (dinA) | 1.2 | NO | |
| dinG | 1.4 | YES | YES |
| dinF | 1.8 | YES | YES |
| himA | 1.3 | NO | |
| ruvB | 1.5 | NO | |
| umuD | 1.2 | NO | |

TABLE 13

Genes not previously known to be DNA damage-inducible found induced by MMC in array experiment

| Gene | Fold induction/ array expt | Available Lux Fusion | Induction of Fusion |
|---|---|---|---|
| mioC | 2.1 | NO | |
| xseA | 2.0 | NO | |
| insB_2 | 2.2 | NO | |
| insB_1 | 2.1 | NO | |
| insA_4 | 2.1 | NO | |
| secG | 2.2 | NO | |
| exbD | 2.2 | YES | NO |
| trkH | 2.1 | YES | NO |
| infA | 2.3 | NO | |
| hslS | 6.7 | NO | |
| hslT | 4.0 | NO | |
| cspA | 2.9 | NO | |
| dniR | 2.1 | YES | NO |
| b0531 | 3.3 | NO | |
| b1847 (yebF) | 3.3 | YES (when inverted) | YES |
| b1228 | 2.5 | NO | |
| b2940 | 2.3 | NO | |
| b0571 (ylcA) | 2.2 | YES | NO |
| b2559 | 2.0 | NO | |
| b3199 | 2.0 | NO | |

Verification of Expected Responses of MMC Induction of Known SOS Genes

The Lux-A Collection of reporter gene fusions was examined for presence of fusions to the genes in Table 11. Four were found to be present in the collection. Each of these was tested for induction by MMC at several doses over a time course of 100 minutes. The expected induction response of a lag period with no change in gene expression followed by an induction of increased bioluminescence was observed in all four cases at several doses of MMC. Thus, this demonstrates that results from DNA array experiments can be verified by using corresponding gene fusions.

Questioning the Negative Result of Non-Induction of Known SOS Genes

As expected, the expression of the known SOS genes was elevated; however the expression of several was elevated less than 2-fold (Table 12) and as such were within a large group of 792 genes the expression of which was elevated by 20% or more. Most of these are likely due to artifacts in the array data rather than to actual biologically relevant responses. To test if strains carrying luxCDABE gene fusions would yield the expected positive result, the three gene fusions that were available in the Lux-A Collection of reporter gene fusions were tested for mitomycin C responses. In all three cases, mitomycin C induced increased bioluminescence. Thus, this demonstrates that negative results from DNA arrays can be questioned by contradictory positive results with corresponding gene fusions.

Questioning or Confirmation of Induction of Previously Unknown MMC Inducible Genes The genes that were not previously known to be induced with mitomycin C were further examined for correlation of DNA array and gene fusion experimental data. For this class of genes, four fusions were available in the Lux-A Collection of reporter gene fusions.

The corresponding luxCDABE fusions to these four genes provided no evidence of increased gene expression induced by MMC.

An additional gene fusion in the Lux-A Collection of gene fusions was found to have a genomic fragment that when inverted would result in a fusion to yebF. In this case, a divergent promoter to the purT gene was present in the chromosomal fragment and strains containing the backward yebF fusion produced light. Following isolation of plasmid DNA, XmaI digestion that releases the insert DNA from the vector, religation and transformation, 10% of the transformants produced light. Of these, 20% (or 2% of the initial transformants) were found to be highly induced by nalidixic acid, another DNA damaging agent. This result strongly suggested that inversion of the insert DNA had occurred in these nalidixic-acid inducible gene fusions. The orientation of the inserted segment to yield a fusion of yebF to the luxCDABE operon was confirmed by DNA sequence analysis. Furthermore, induction by mitomycin C was demonstrated, as shown in FIG. 2.

Example 4

Functional Definition of Postulated Promoter Regions

Figure 8A:
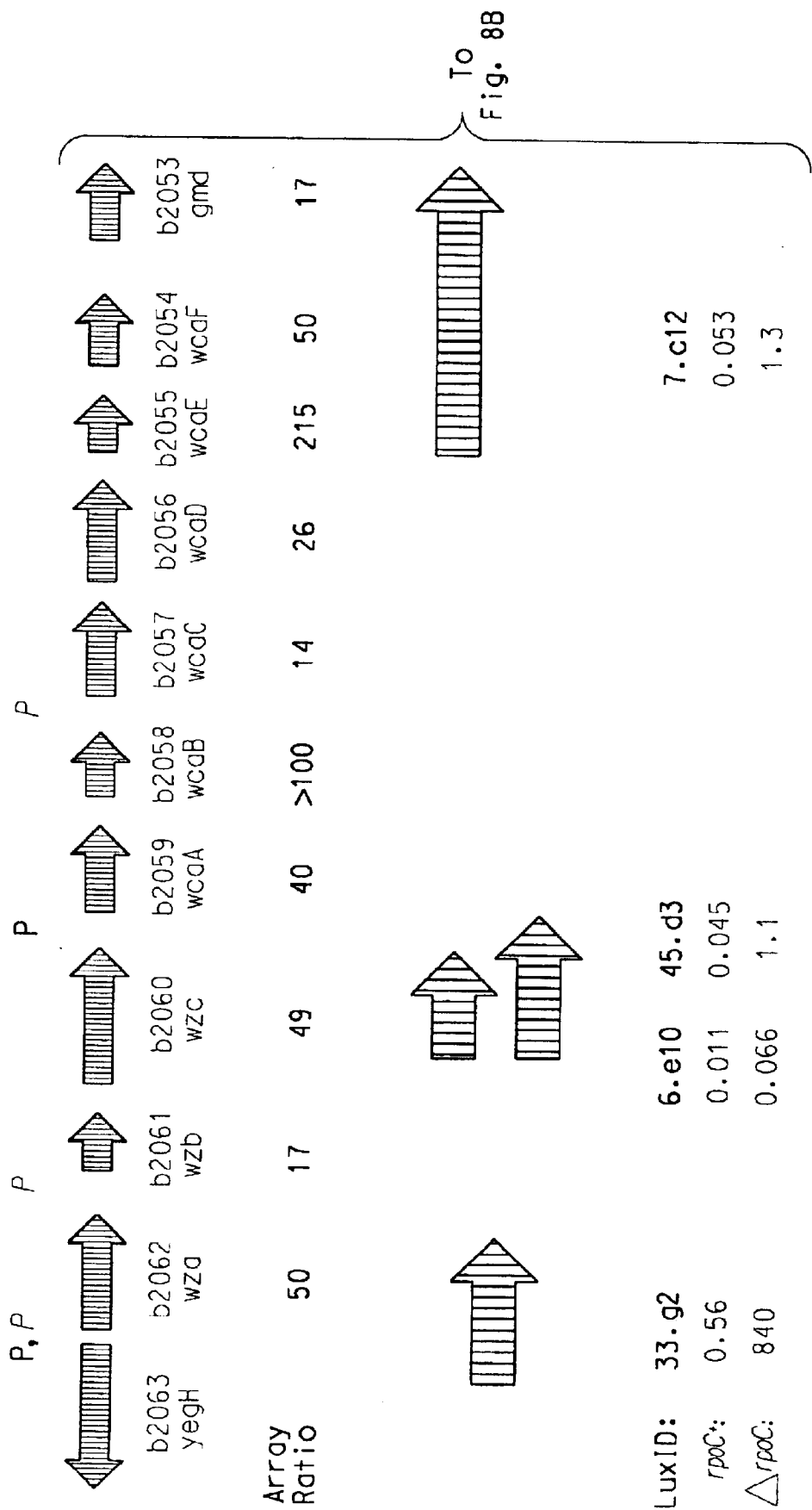
FIG. 8 describes the predicted promoters in a gene cluster of 20 genes for typeI extracellular polysaccharide in *E. coli* and the promoter activity of luxCDABE gene fusions from the region encoding production of type I extracellular polysaccharide. The *E. coli* genes in this region are shown with the top set of arrows. Above this line are the predicted promoters regions from two sources (P, Blattner et al., (1997) *Science* 277:1453–1462); P, Thieffry et al. (1998) *Bioinformatics* 14:391–400). The two promoters supported by DNA array and gene fusion data presented here are shown in bold type. The b designation and common name for each gene is shown. The ratios of the deduced mRNA level in the rpoC mutant strain to the deduced mRNA level in the rpoC+ strain determined by the micro array method are shown on the next line. The mapped location of the chromosomal inserts of selected luxCDABE gene fusions in this region are shown with the second set of thicker arrows. Below these are the lux clone identification number and bioluminescence data (RLU/$10^9$ cfu) for each plasmid in the rpoC+ *E. coli* host strain and the host strain carrying an rpoC mutation. In the case of overlapping gene fusions, the shorter one is listed first.
Figure 8B:
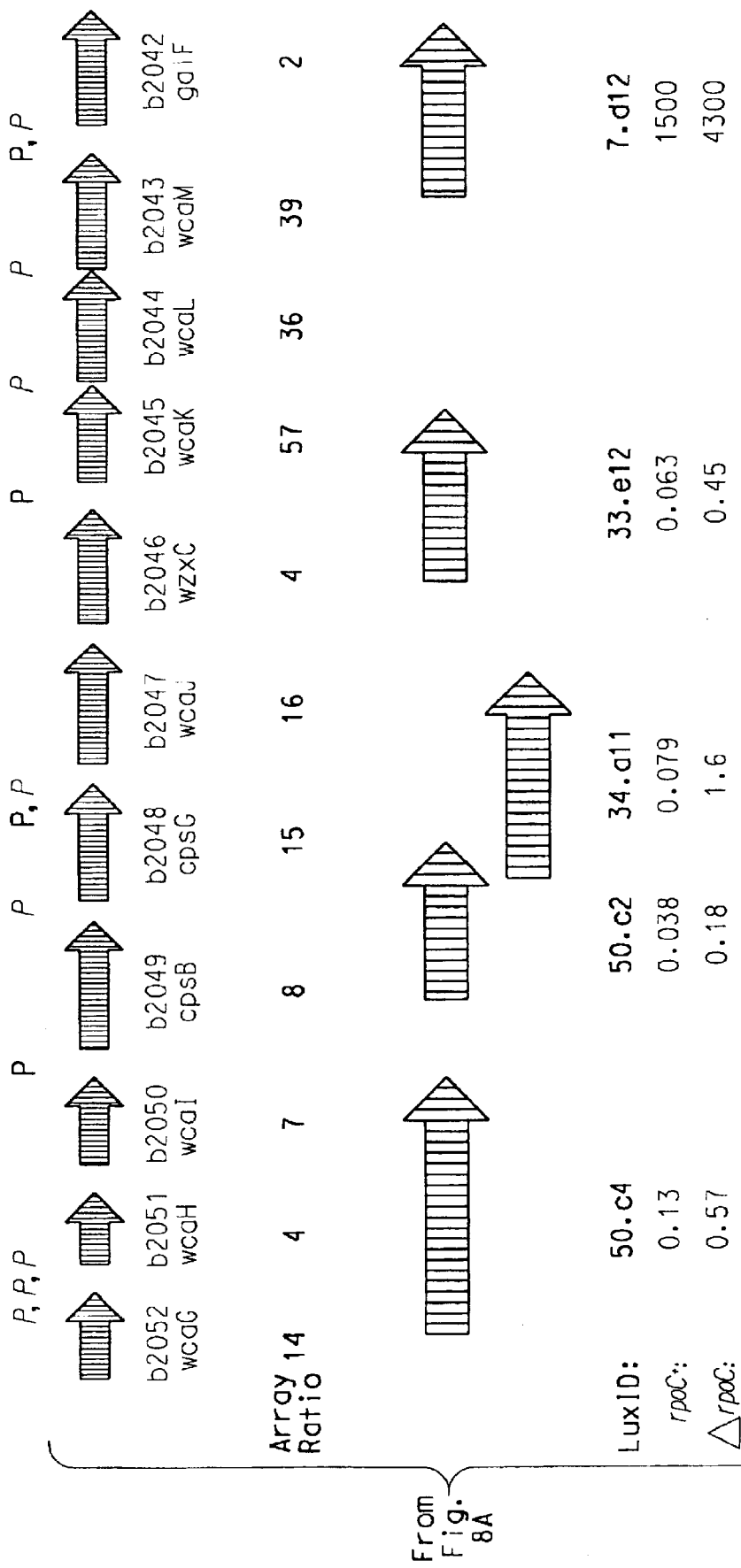

The genes encoding production of type I extracellular polysaccharide in E. coli are located in a cluster of 20 genes (Stevenson et al. (1996) J. Bacteriol. 178: 4885–4893). An upstream promoter for these genes has been identified (Stout, V. (1996) J. Bacteriol. 178: 4273–4280) and its regulation has been characterized (Gottesman, S. (1995) Two-component Signal Transduction. American Society of Microbiology pp253–262; Wehland and Bernhard (2000) J. Biol. Chem. 275:7013–7020). Nonetheless, the transcriptional organization of this region has not been completely defined. The annotated sequence for these genes (Blattner et al. (1997) Science 277:1453–1462), which are transcribed from one strand of the genome, suggests the existence of several putative promoters and activator binding sites. Furthermore, a prediction of operon structure in this region suggests that these genes may be organized into several transcriptional units (Thieffry et al. (1998) Bioinformatics 14:391–400). FIG. 8 summarizes the predicted promoters in this region. Unexpectedly, an E. coli DNA microarray-based experiment with strains 397C, containing a truncated ' subunit of RNA polymerase, and P90, an isogenic rpoC$^+$ control, suggested that RNA transcripts in this region were affected by the rpoC mutation. Expression of genes b2043 through b2062 was coordinately upregulated in the rpoC mutant (FIG. 8). The elevated expression is most readily explained if a single transcript starts before b2062 and ends between b2043 and b2042 (galI). If this is true, the region upstream of b2062 should contain a promoter. That region was fused to the luxCDABE operon in lux-a.pk033.g2. Transformants of P90 and 397C were grown at 30° C. in LB medium containing 100 μg/ml ampicillin. Bioluminescence and turbidity, recorded with a Klett-Summerson colorimeter (Van Dyk et al. (1995) J. Bacteriol. 177:6001–6004), of actively growing cultures were used for calculation of light production per $10^9$ cells. The unpaired t-test was used to compare quadruplicate bioluminescence measurements of strains carrying gene fusions to the control strain carrying the parental plasmid. The bioluminescence produced when the lux-a.pk033.g2 gene fusion was placed into strain P90 was weak (0.56+/−0.06 RLU/$10^9$ CFU), but yet was significantly greater (P<0.0001) than the bioluminescence produced by the parental plasmid in the same host strain (0.028+/−0.010 RLU/$10^9$ CFU). These data are consistent with a promoter in the region upstream of b2062 that is not very active in strain P90 growing in LB medium. The bioluminescence of this gene fusion was elevated 1500-fold when placed in strain 397C (FIG. 8). This strong promoter activity driving luxCDABE gene expression is, therefore, dependent upon the rpoC$^-$ mutation. In contrast, several other gene fusions to chromosomal DNA segments in this region, whether they contained predicted promoter regions or not, had very low levels of activity in both the wild type and rpoC$^-$ mutant (FIG. 8). Thus, the data from both the DNA microarray experiments and from gene fusions are consistent with cotranscription of the twenty genes in this region. The end of the operon was defined by a gene fusion to the galF upstream region (in lux-a.pk07.d12) that strongly drove luxCDABE transcription. The activity of this promoter region was not dramatically effected by the rpoC mutation (FIG. 8), in agreement with the DNA array data.

Example 5

Highly Parallel Transcription Analysis Using a High Density Array of Cellular Reporters Proof of principle with Luxarray 0.5

A solid phase assay system consisting of reporter clones growing in the presence or absence of a perturbation, biological, environmental or chemical was developed. This was accomplished by growing the reporters on a porous membrane (Biodyne B, Nunc) seated on top of solid growth media in a culture dish (OmniTray, Nunc). Luminescence was measured either by a luminometer or by creating an image of the entire culture and quantitating the pixel density. Effects of perturbants can be determined by comparison of luminescence generated by treated and control cultures. Growth on the surface of the membrane allows the reporter assay to be moved between conditions as required. Experimental protocols often involve perturbations that prohibit long term exposure due to cell death or other irreversible effects. The ability to move the entire array to new growth conditions allows one a great variety of experimental schemes such as pulsed or pulse/chase exposures, reversibility, and short term kinetic studies.

Several important characteristics of the assay system needed to be evaluated. In particular, growth density and conditions, sensitivity, reproducibility, and the ability to perturb the reporters and detect changes were major focus points. Development of this assay system was initiated using a collection of 10 well characterized clones, the parental plasmid clone, and media alone (Table 14). The set of 10 clones represented a distribution of signal strength as well as response to perturbation with DNA damaging agents, in particular nalidixic acid. Initial experiments were designed to benefit from the sensitivity and simplicity of measuring luminescence with a 96-well luminometer (Dynex ML3000). Printing was accomplished using a BioMek 2000 (Beckman Coulter) equipped with a High Density Replication Tool (HDRT). Sterilization in between transfers was accomplished by soaking the pins successively in 0.2% SDS in water, sterile water, and 70% ethanol. After sterilization, the pins are air-dried prior to the next transfer.

TABLE 14

Luxarray 0.5 Clone Description

| Strain | Clone No. | Fusion to: | Biolumi-nescence* | Comment |
| --- | --- | --- | --- | --- |
| DPD2083 | N.A. | N.A. | none | Parental plasmid without insert |
| DPD2282 | 65.d4 | lacZ | moderate | "Constitutive" expression in LB/low expression in LB + glucose |
| DPD2247 | 85.a5 | dinF | low | SOS regulon/Nalidixic acid and Mitomycin C inducible |

TABLE 14-continued

Luxarray 0.5 Clone Description

| Strain | Clone No. | Fusion to: | Biolumi- nescence* | Comment |
|---|---|---|---|---|
| DPD2248 | 24.f5 | dinG | moderate | SOS regulon/Nalidixic acid and Mitomycin C inducible |
| DPD2249 | 55.a3 | dinP | moderate | SOS regulon/Nalidixic acid and Mitomycin C inducible |
| DPD2250 | 22.d4 | recA | high | SOS regulon/Nalidixic acid and Mitomycin C inducible |
| DPD2253 | 01.b6 | uvrA | moderate | SOS regulon/Nalidixic acid and Mitomycin C inducible |
| DPD2242 | 21.g11 | lon | moderate | Heat shock regulon |
| DPD2243 | 54.c3 | clpB | moderate | Heat shock regulon |
| DPD2245 | 42.c8 | rpoD | low | Heat shock regulon |
| DPD2084 | 06.b4 | yciG | low | SigmaS-dependent stress responsive |
| DPD2090 | 23.c7 | osmY | low | SigmaS-dependent stress responsive |

*Bioluminescence is measured in the liquid culture by luminometer.

Strains were grown overnight at 37° C. in 40 μl LB in 96-well dishes. These cultures were designated "printing plates" and were used as the cell source to manufacture the arrays.

Figure 3A:
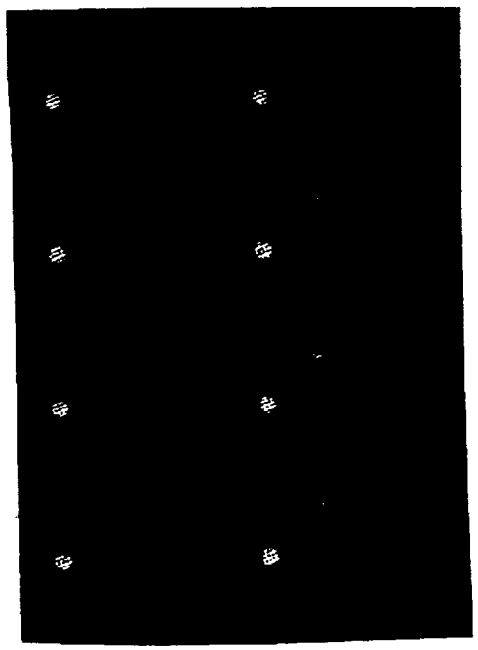
FIG. 3A describes the cell placement to replicate 96 well spacing to fit a microplate luminometer. In the white light on the left, each replicate of the twelve spots is outlined. The bioluminescent image of the same plate is shown on the right.
Figure 3A:
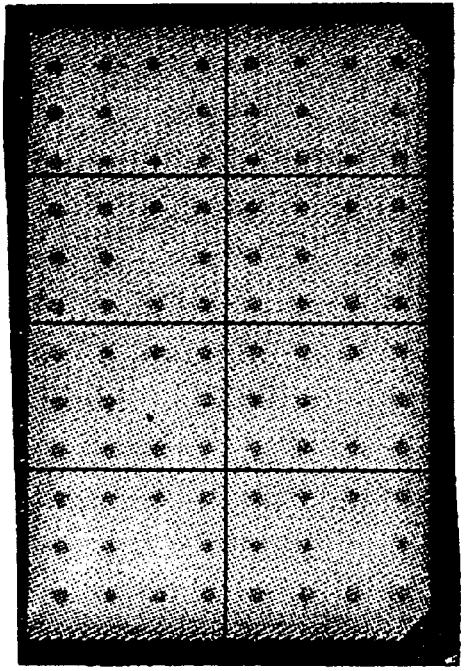
Figure 3B:
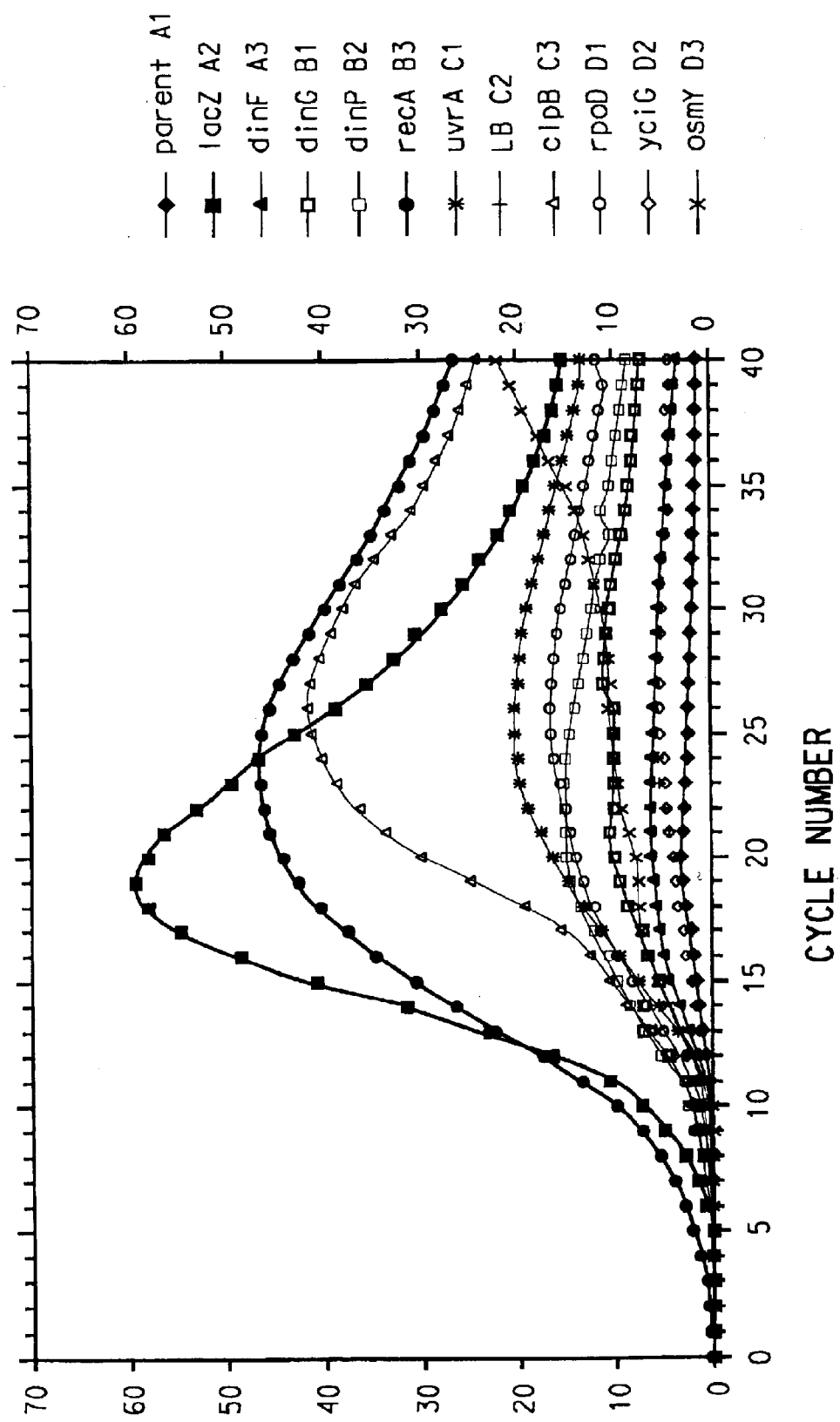
FIG. 3B describes the signal collected for each clone as a function of time. Each cycle was about 20 min.
Figure 3C:
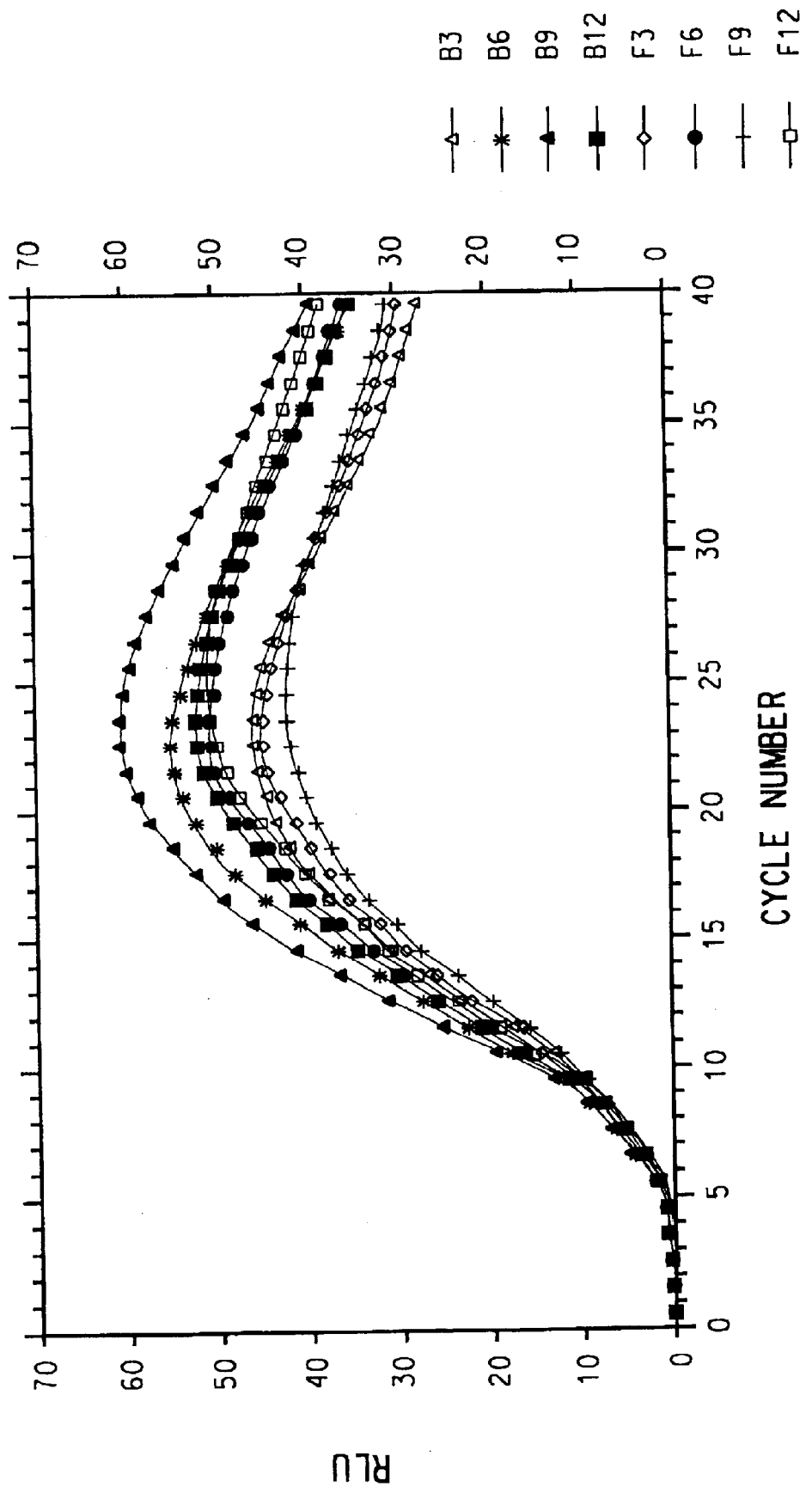
FIG. 3C describes signals collected from 8 replicates of same clone.

Membranes were sterilized with UV illumination for 10 min then placed in contact with prewarmed media in a culture dish. The clones and controls were printed onto an approximately 8×12 cm membrane mimicking the pattern of a 96-well plate (FIG. 3A). Strains were printed to generate 8 repeating sections of the 10 strains and two controls and placed in a Dynex ML3000 luminometer prewarmed to 37° C. Luminescence data was collected for each spot for 40 cycles of 20 min duration (overnight). FIG. 3B shows the signal collected for each clone as a function of time. FIG. 3C shows signal collected from the replicate spots of the same clone (recA-luxCDABE). The data clearly indicated that the strains were well behaved in the new solid phase system. Without exception, the signal strength measured corroborated the data obtained in liquid culture. Additionally, replicates varied minimally, again similar to liquid culture measurements.

Next the system was evaluated for its ability to determine responses to perturbation, in this case, DNA damage caused by nalidixic acid. Parental clone and two nonresponding reporters, osmY, and lacZYA, and three DNA damage responsive reporters, uvrA, recA, dinG, were chosen. Strains were printed onto duplicate membranes over LB agar from fresh overnight cultures as described and incubated for 6 hr at 37° C. to allow the cells to enter an exponential growth phase. The membranes were moved to new, pre-warmed plates containing varying amounts of nalidixic acid and light readings collected with an ML3000 luminometer. Luxarray 0.5 clones (FIGS. 4A and B) were printed onto membranes and grown initially on LB then moved to plates containing 0 μg/ml (diamonds), 1 μg/ml (squares), or 5 μg/ml nalidixic acid (triangles). Luminescence was measured with a Dynex ML3000 luminometer every 30 min for 2 hrs. As shown in FIG. 4B, the expected nalidixic acid mediated upregulation of genes in the SOS regulon was detected as increased bioluminescence. In contrast, strains containing fusions to non-DNA damage responsive genes, osmY and lacZYA, were unaffected by nalidixic acid treatment (FIG. 4A). The strain containing the parental plasmid, pDEW201, without a promoter driving luxCDABE expression produces very low levels of bioluminescence that are very close to the background measured on a ML3000 luminometer for strains grown in 96-well microplates. The apparent basal bioluminescence and upregulation of this strain (FIG. 4A) is likely due to cross-talk from an adjacent strain containing a DNA damage responsive gene fusion.

High Density Luxarray 0.5

The clone set of Luxarray 0.5 was used to develop a highly parallel solid phase assay by printing the clones at high density on the approximately 8×12 cm membrane. These arrays were used to further develop the system.

Printing Density

In an effort to more closely approximate the final assay system, the clones of Luxarray 0.5 were used to determine the maximum density one could print the cells at and carry out useful analyses. Arrays were printed as above at increasing density and grown for 8 hr at 37° C. Luminescence was imaged using an EagleEye II (Stratagene, La Jolla, Calif.). From visual inspection individual clonal areas of growth could be resolved at densities up to 6144 individual spots per membrane. From a comparison of the size of the growth areas from different densities, it appeared that in the 8 hr growth period, there was a nutrient-limit effect that resulted in an inversely proportional amount of growth as density increases. At this density, there is over two-fold greater then the estimated number of transcription units in the entire E. coli genome. Thus a single 8×12 cm array could represent the entire E. coli genome in duplicate with capacity left for controls. Alternatively full genome coverage of two different strains or different species could be printed on the same array.

High Density Array Image Collection

The essence of this assay is to collect an image of the signal generated from reporter constructs such that the signal intensity can be subsequently quantified. This requires not only that the collection parameters (focal plane, magnification, integration time, and algorithm) are constant but also that the downstream image analysis software has the ability to process the images generated. The most common application of this assay, chemical perturbation, requires physically relocating a membrane from one culture plate to another. This results in images with minimal X-Y positional registration. Several commercially available products can efficiently process these images. ArrayVision™ (Imaging Research, Toronto, Canada) and ImageQuant (Molecular Dynamics, Sunnyvale, Calif.) are two examples of appropriate software packages.

High Density Luxarray 0.5 Nalidixic Acid Perturbation

The clones of Luxarray 0.5 were used to print arrays as described above at a 4×4 density. That is to say that each single spot as in FIG. 3 was replicated 16× in a 4×4 subarray. This resulted in each clone being printed 128 times on different areas of the array. Arrays were printed in triplicate from fresh overnight cultures onto membranes on plates containing LB media. After 6 hr of growth at 37° C. membranes were moved to prewarmed plates containing either LB media or LB media supplemented with 5 μg/ml nalidixic acid (NA) previously demonstrated to cause detectable induction of responsive promoters for a wide range of promoter strength (FIG. 4). Cultures were replaced at 37° C. to continue growing. Images were collected for each array every two hours from 0–8 hr after relocation using a cooled CCD camera (Fluor Chem 8000: f0.85 lens, 2 min exposure. AlphaInnotech). Spot intensity was determined using ArrayVision™ (Imaging Research, Toronto, Canada). FIG. 5 shows the results for selected strains containing reporter gene fusions.

As found with the low density experiments quantified with the luminometer, the expected responses for each clone were well demonstrated. The five documented DNA damage-responsive reporter constructs clearly show an upregulation of expression. In contrast, light production from the strain carrying the lac promoter fusion as well as several strains carrying other promoter fusions was decreased. This decreased bioluminescence likely reflected the decreased growth and metabolism of the nalidixic acid treated strains and demonstrates the specificity of the upregulation of the SOS-regulon gene fusions. Furthermore, the signal from the strain containing the parental plasmid is of dramatically lower magnitude than that of strains with promoter-lux fusions, thus, demonstrating the advantage of the cooled CCD camera for data capture.

Lux Array 1.0, a Highly Parallel Promoter Activity Assay.

Selection of a Maximal Non-Redundant Set of lux Gene Fusions.

Figure 6:
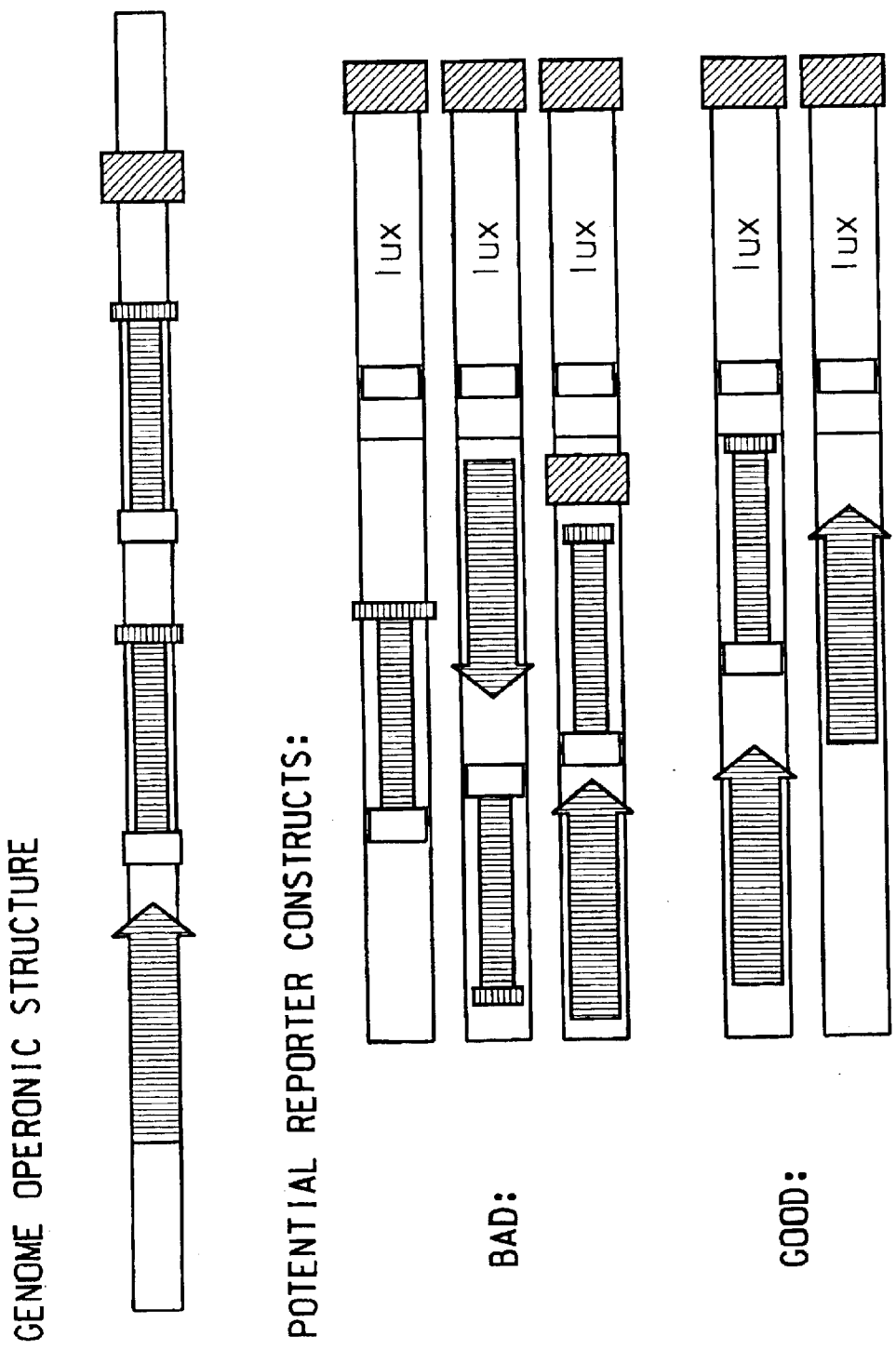
FIG. 6 describes graphical representation of selection criteria implemented to select Luxarray 1.0 Clones.

The genome-registered Lux-A luxCDABE gene fusion collection (described in Example 1) provided a list of 4988 plasmid-borne gene fusions, each with boundary information relative to the *E. coli* genome and the orientation relative to the lux operon. An operably linked or a functional construct was defined as one consisting of a genomic fragment encompassing a promoter adjacent to the promoterless lux operon in an orientation that causes transcription initiated at the promoter to proceed into and through the lux operon. Therefore, to identify the functional subset of the collection, criteria were computationally applied to filter the list of clones first for functionality and second for redundancy. A list of definitions of documented and predicted operons (Thieffry et al. (1998) *Bioinformatics* 14:391–400) was used to define genomic coordinates of the operons as the translational start codon position of the first open reading frame (ORF) in the operon and the translational stop codon position of the last ORF in the operon. Additional information included the strand on which the operon is coded (direction of transcription), and gene names (common or "b" number). The lux gene fusions were filtered computationally using the following assumptions; (i) a functional transcriptional fusion would result from any genomic fragment starting greater than 50 base pairs upstream of the start codon of the first ORF and ending anywhere between the start codon of the first ORF in the operon and the stop codon of the last ORF in the operon, thereby eliminating the occurrence of a transcriptional stop signal in the construct between the promoter and the lux operon; and (ii) the promoter contained in the genomic fragment must face in the correct orientation relative to the lux operon (pictorially represented in FIG. 6). Finally, in cases when more then one clone fit the criteria for a single operon, only the one construct containing the genomic fragment representing the greatest amount of upstream sequence was retained thereby eliminating redundancy. The PERL code used and the resulting list of 689 selected gene fusions are found in Scheme 1 and Table 18 (following Example 7). These fusions represent 27% of the 2584 known and predicted transcriptional units in the *E. coli* genome. Individual cultures of strains containing the identified gene fusions were rearrayed from the ninety original culture plates to create a set of sixteen 96-well microplates containing all the identified fusions, duplicated with side by side symmetry, including appropriately placed controls. These 16 plates represent were used to generate the cellular arrays for use in subsequent analyses.

Preparation of Reporter Array.

The *E. coli* strains were grown overnight at 37° C. in 40 μl LB medium supplemented with 100 μg/ml ampicillin in a set of sixteen 96-well dishes. These cultures were designated "printing plates" and were used as the cell source to manufacture the arrays. Porous membranes (Biodyne B, Nunc) were sterilized with UV illumination for 10 min then placed in contact with pre-warmed of solid LB growth media in a culture dish (OmniTray, Nunc). Printing of 4×4 subarrays was accomplished using a BioMek 2000 (Beckman Coulter) equipped with a High Density Replication Tool (HDRT). Sterilization in between transfers was accomplished by soaking the pins successively in 0.2% SDS in water, sterile water, and 70% ethanol. After sterilization, the pins are air-dried prior to the next transfer. The *E. coli* strains in the LuxArray were printed onto an approximately 8×12 cm membrane in two sets of triplicates.

Growth in the Array.

The growth rate of individual colonies was evaluated because initial experiments clearly demonstrated a large distribution of growth rates for the reporter strains in the system. In order to differentiate between clone-dependent or system-dependent sources of this variability, bioluminescent cellular arrays were generated in triplicate on different days using LB agar media containing 10 μg/ml tetrazolium blue. The product generated when live cells reduce tetrazolium blue is an insoluble blue precipitate. This greatly increased contrast between the cells and the media simplifying direct imaging of the cells by normal light. For each of the triplicate experiments, each clone was visually scored to determine the size of the growth generated during 8 hrs of incubation at 37 C (data not shown). Variability was clearly clone-specific and very consistent from day to day. As the majority of proposed analyses are relative measurements, and inter-clone comparisons are unlikely, this type of growth variability does not effect the applicability or robustness of the overall assay system. No further attempts were made to determine the source of the variability, however it can be assumed that it is a result of the plasmid constructs carried by the clones.

Bioluminescence of LuxArray 1.0.

Figure 7:
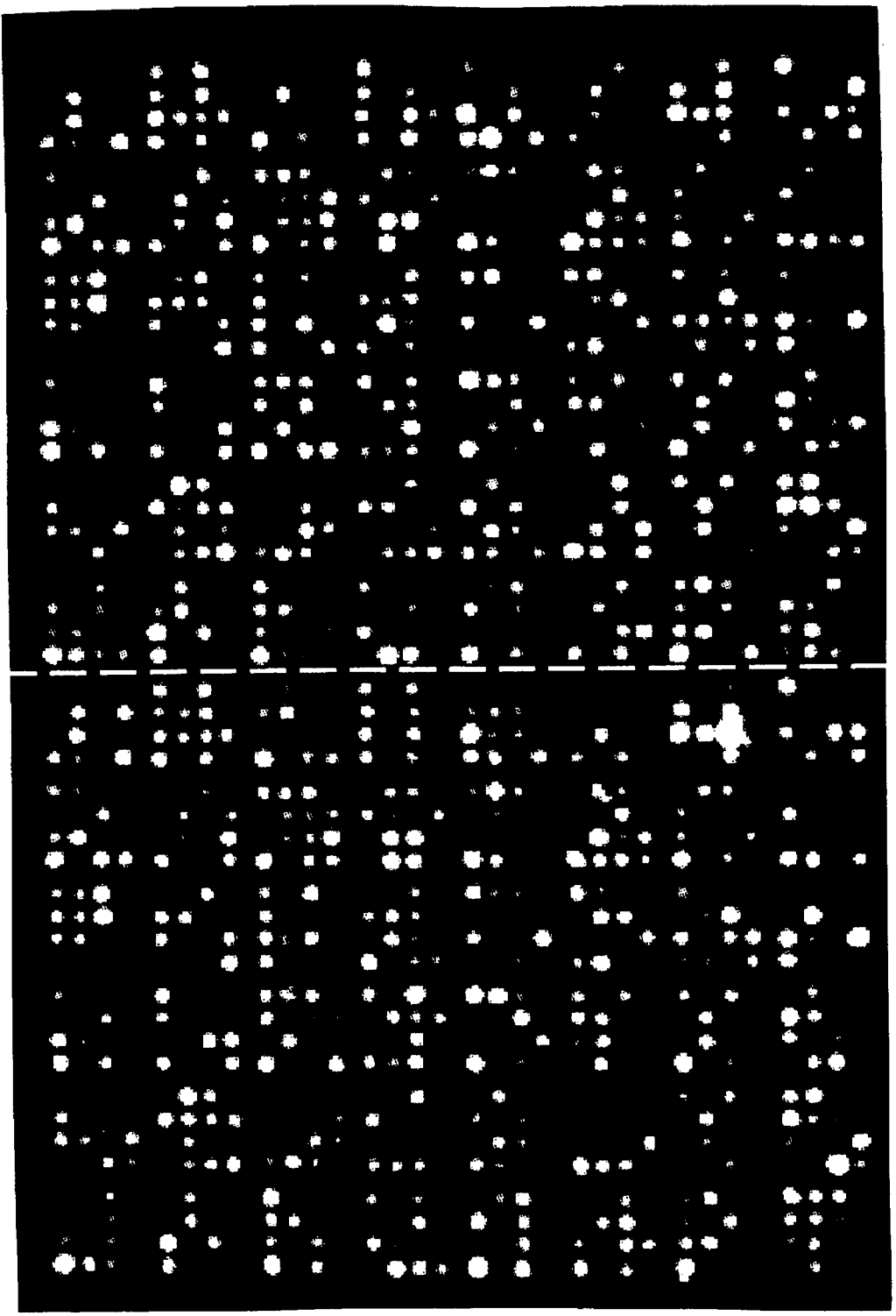
FIG. 7 describes bioluminescence captured from Luxarray 1.0 reporters after 14 hr growth on LB media by cooled CCD array camera (Fluor Chem 8000, AlphaInnotech).

Images of the bioluminescence were using a cooled CCD camera (Fluor Chem 8000: f0.85 lens, 2 min exposure, AlphaInnotech) without additional light source. The bioluminescence from one such array grown for 16 hours on rich media is shown in FIG. 7. The array in FIG. 7 shows side by side replicate subarrays that include control strains, a strain with lacZYA promoter fusion and a strain containing the parental plasmid (pDEW20 1).

Identification of Nalidixic Acid Responsive Gene Fusions Using LuxArray 1.0.

The antibiotic nalidixic acid, an inhibitor of DNA gyrase known to be a effective inducer of the SOS DNA damage stress response was used to demonstrate the utility of this array. Arrays were printed from fresh overnight cultures onto membranes on plates containing LB media. After 6 hr of growth at 37° C. membranes were moved to pre-warmed plates containing either LB media or LB media supplemented with 5 μg/ml nalidixic acid then replaced at 37° C. to continue growing. Images were collected for each array every two hours from 0–8 hr after relocation using a cooled CCD camera (Fluor Chem 8000: f0.85 lens, 2 min exposure, AlphaInnotech).

Spot intensity of each image was determined using ArrayVision™ (Imaging Research, Toronto, Canada) and the resultant pixel density measurements imported into a template with identifiers for each spot. The average signal for each of the triplicate spots was calculated. The background signal, which results from cross illumination of neighboring spots, was calculated by finding the median of the 24 spots containing a strain with the parental plasmid on each of the triplicate arrays and the calculating the average of the three medians. This background signal was calculated at each of the time points and subtracted from each measurement at the corresponding time point. All negative numbers were converted to zero.

Data normalization to account for inhibition of growth by nalidixic acid was accomplished by finding the sum of the averaged signals of each spot in the array for each treatment at each time point. A normalization factor (NF) was calculated as follows:

NF=Total array signal (time zero, LB control)/Total array signal (time x, condition y)

Each measurement was multiplied by NF to yield a normalized signal. Ratios the nalidixic acid treated spot to the corresponding control spot were calculated using the normalized data.

The ratios of the normalized data were compared for each of the duplicate spots resulting from independent cultures in the array. Putative nalidixic acid upregulated gene fusions were selected as those for which the ratio in both duplicate spots was at least 2 at both the 2 hour and 4 hour time points. Twelve gene fusions were selected by these criteria (Table 15).

These twelve gene fusions include three well-characterized members of the SOS regulon as well as several fusions to promoters not previously known to be upregulated by nalidixic acid treatment. The DNA sequence of plasmid DNA isolated from each of these twelve cultures reconfirmed the identity of each inserted DNA. The LuxArray contains a total of six gene fusions to SOS regulon operons, all of which would be expected to be upregulated by nalidixic acid. Three were, thus, scored falsely as negatives. An examination of the data showed that two of these false negatives were reproducibly upregulated but not at level of the selection criteria; a fusion to uvrD was upregulated by 1.6 and 1.9 fold at 4 hours of nalidixic acid treatment, while one to ruvA was upregulated 1.7 and 2.1 fold at that time point. The third did not have consistent responses; the ratio of nalidixic acid treated to untreated for the dinF-lux fusion was found to be 4.2 in one of duplicate spots and 0.7 in the other.

Validation of Nalidixic Acid Upregulated Gene Fusions by Retesting in Liquid Medium.

Each of the newly identified putative nalidixic acid upregulated gene fusions and two of the known SOS gene fusions were retested using exponentially growing cultures in liquid medium with seven concentrations of nalidixic acid (80 μg/ml in two fold dilutions to 1.2 μg/ml). Several concentrations of nalidixic acid were used because the differences in responses between liquid and solid growth were not known. Light production of 100 μl duplicate cultures at 37° C. was quantitated using a 96 well plate luminometer (Luminoskan Ascent, Labsystems). Table 15 shows the results expressed as ratios of the signal from the nalidixic acid treated cultures to the untreated control at 2 hours at the concentration that yielded the maximal response. Also shown is the number of concentrations of nalidixic acid tested that resulted in response ratios of 1.5 or greater. It should be noted that the liquid medium tests were not corrected for growth inhibition by nalidixic acid. Using a standard of a maximal response ratio of at least 1.8 and responses ratios that were >1.5 fold at 3 or more concentrations, 7 of the 9 putative novel nalidixic acid upregulated gene fusions were shown to be reproduced in liquid medium.

Mitomycin C Responses and Effect of lexAind Mutation.

Figure 9B:
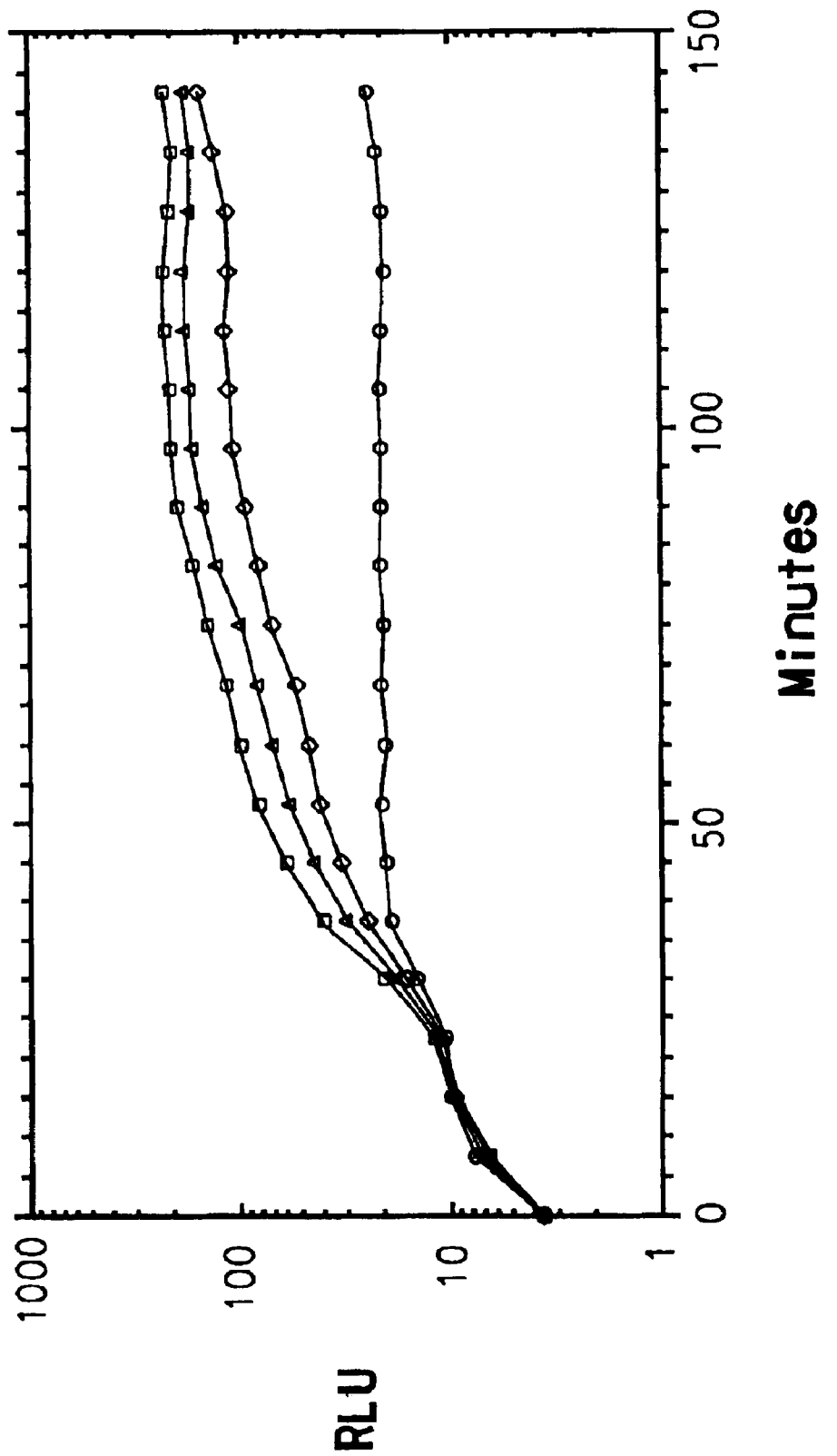
FIGS. 9 (A–D) represents generally the induction of the promoter b1728 by nalidixic acid (NA) in lexa+ host (FIG. 9A) in comparison to the promoter in lexind host (FIG. 9C), and induction of the promoter b1728 by mitomicyn C (MC) in lexA+ host (FIG. 9B) in comparison to the promoter in lecind host (FIG. 9D).
Figure 9C:
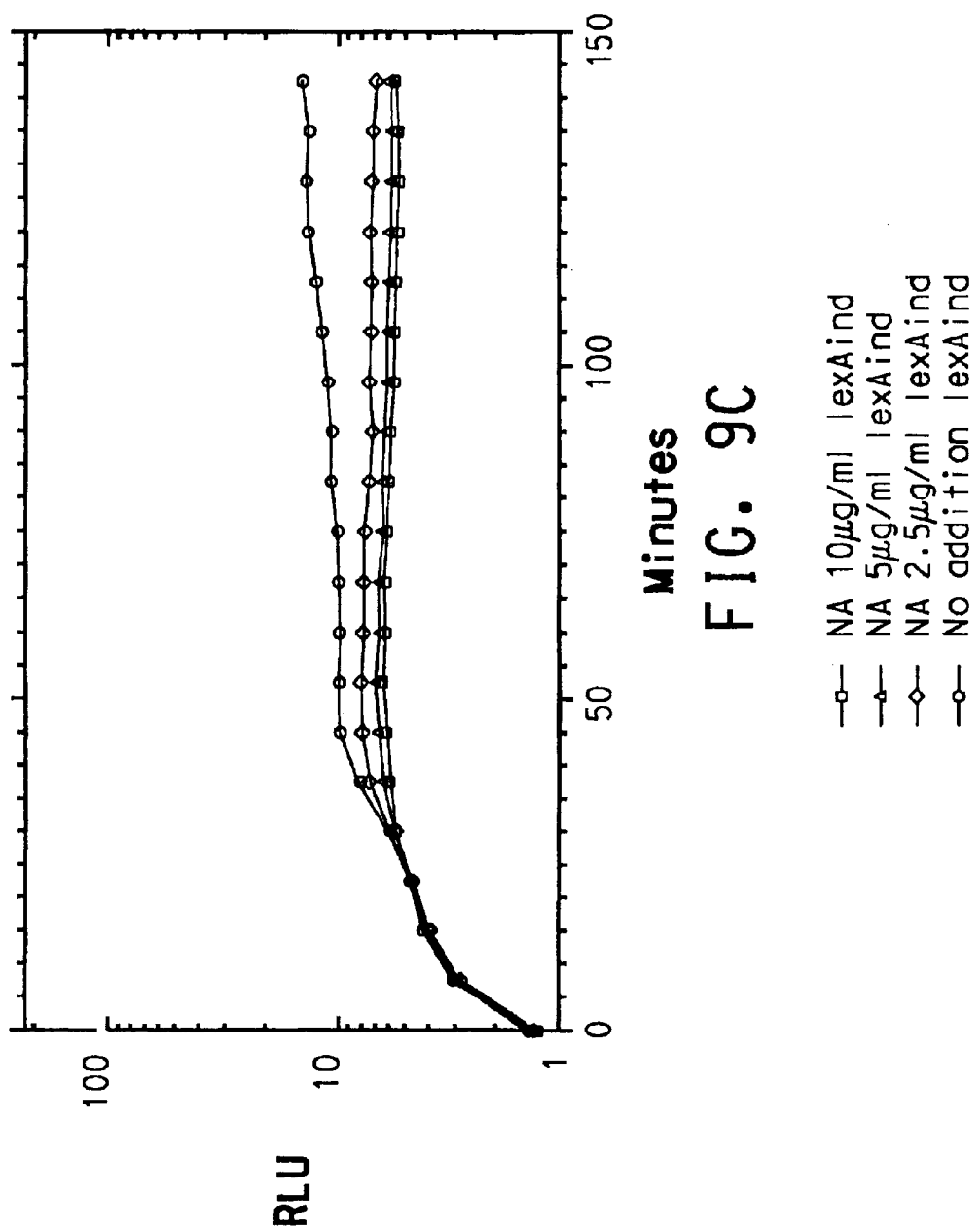
Figure 9D:
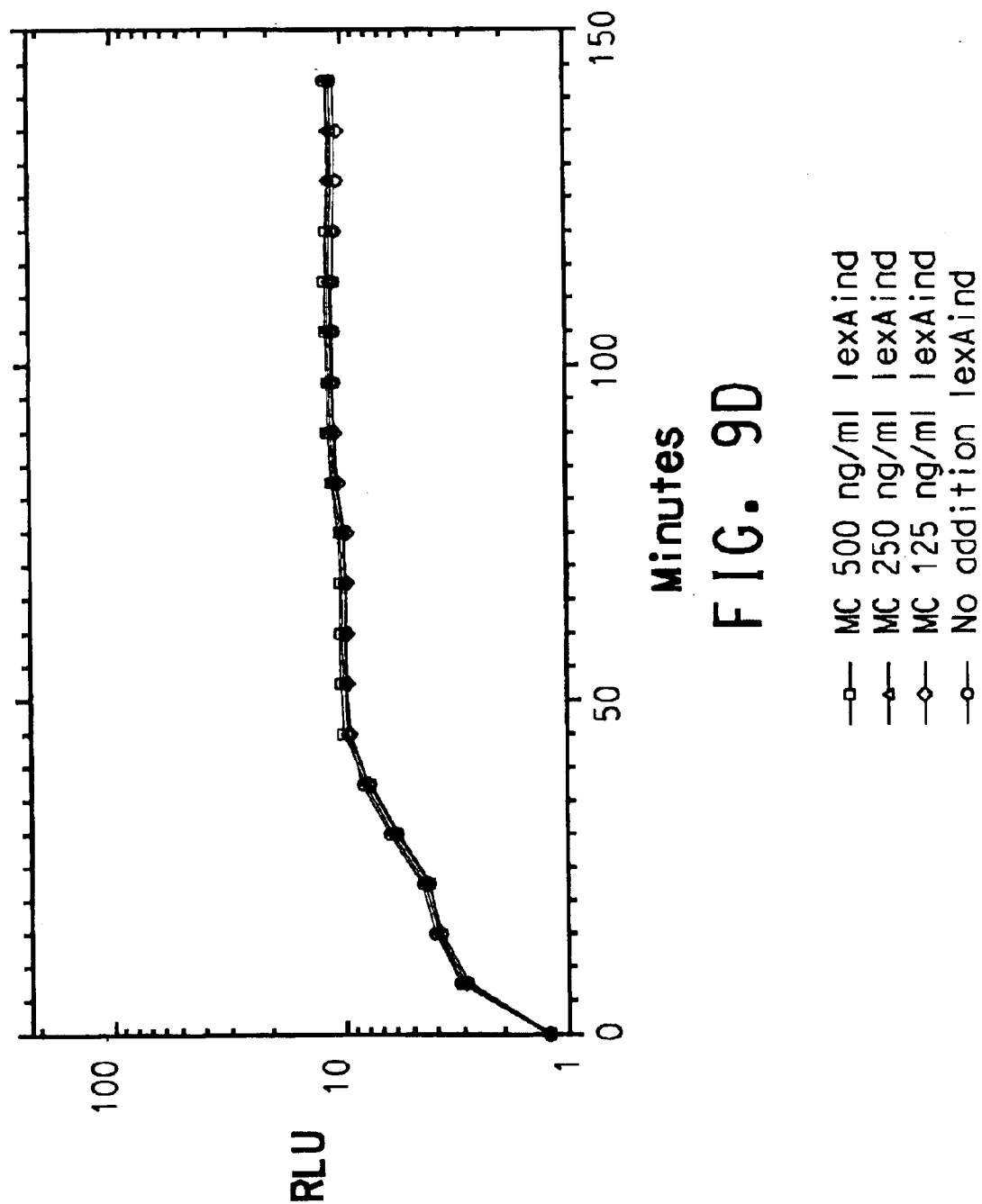

Mitomycin C, a DNA damaging compound with a different mechanism of action from nalidixic acid, was used to determine if these newly discovered nalidixic acid upregulated gene fusions were generally responsive to DNA damage. In addition, the effect of a lexAind mutation was tested to determine if any of these were part of the SOS regulon. The expectation is that SOS regulon member will be induced by both nalidixic acid and mitomycin C in a manner that is dependent on lexA function (Walker, G. C., (1996) *Escherichia coli* and Salmonella: Cellular and Molecular Biology ASM Press). As shown in FIG. 9, a fusion of the promoter region of b1728 to luxCDABE was clearly induced by both nalidixic acid and mitomycin C in the lexA+ host, but was not induced by these chemicals in the lexaind host strain. Thus, these results demonstrate that upregulation by nalidixic acid as well as mitomycin C is controlled by LexA. This is consistent with the observation of upregulation of the b1728 mRNA transcript upon mitomycin C treatment in a LexA dependent fashion (Fernandez de Henestrosa et al. (2000). Mol. Microbiol. 35:1560–1572).—Likewise, two gene fusions, those to oraA and yigN were identified as new members of the SOS regulon (Table 16). Interestingly, four of the nalidixic acid responsive gene fusions were not upregulated by mitomycin C in the lexA+ host suggesting that they are not generally DNA damage responsive, but rather are more specifically responsive to nalidixic acid. Negative, non-DNA damage responsive gene fusions were also included (Table 16).

Thus, the LuxArray assay was useful to identify novel nalidixic acid upregulated genes in *E. coli*. Likewise, this robust assay can be used generally in a fashion parallel to hybridization assays to monitor transcriptional changes. The multiple whole genome scale capacity and relative simplicity of manufacture allow for significant throughput. This assay is an important addition to efforts making functional assignment of promoter activity.

TABLE 15

Nalidixic acid responses on solid and in liquid medium

| Fusion to gene or operon: | Lux ID | Solid expt NA/LB, t = 2 hr | Solid expt NA/LB, t = 4 hr | Solid expt NA/LB, t = 6 hr | Solid expt NA/LB, t = 8 hr | Nal conc of max induction in liquid | Liquid expt. NA/LB t = 2 hr | # of conc with > 1.5 fold up |
|---|---|---|---|---|---|---|---|---|
| Known SOS regulon members: | | | | | | | | |
| dinG ybiB | lux-a.pk0024.f5 | 3.4 | 4.2 | 3.1 | 2.6 | 5 ug/ml | 4.18 | 6 |
|  | lux-a.pk0024.f5 | 2.5 | 3.7 | 3.5 | 2.9 | | | |
| dinP | lux-a.pk055.a3 | 3.1 | 5.1 | 4.2 | 3.1 | 5 ug/ml | 7.60 | 7 |
|  | lux-a.pk055.a3 | 5.5 | 11.0 | 8.1 | 6.3 | | | |
| uvrA | lux-a.pk0001.b6 | 2.5 | 2.3 | 1.6 | 1.0 | nd | nd | nd |
|  | lux-a.pk0001.b6 | 2.9 | 2.4 | 1.1 | 0.6 | | | |

TABLE 15-continued

Nalidixic acid responses on solid and in liquid medium

| Fusion to gene or operon: | Lux ID | Solid expt NA/LB, t = 2 hr | Solid expt NA/LB, t = 4 hr | Solid expt NA/LB, t = 6 hr | Solid expt NA/LB, t = 8 hr | Nal conc of max induction in liquid | Liquid expt. NA/LB t = 2 hr | # of conc with > 1.5 fold up |
|---|---|---|---|---|---|---|---|---|
| Nalidixic acid upregulated on both the solid LuxArray and in liquid culture ||||||||
| b1169 | lux-a.pk0015.d6 | 2.3 | 6.4 | 2.7 | 0.6 | 20 ug/ml | 2.71 | 6 |
|  | lux-a.pk0015.d6 | 2.2 | 4.1 | 1.9 | 0.8 |  |  |  |
| b1728 | lux-a.pk033.c5 | 3.7 | 4.3 | 3.2 | 2.6 | 5 ug/ml | 3.67 | 7 |
|  | lux-a.pk033.c5 | 2.1 | 3.1 | 3.3 | 2.5 |  |  |  |
| b1936 | lux-a.pk0019.g1 | 2.5 | 7.7 | 9.7 | 7.1 | 10 ug/ml | 2.34 | 6 |
|  | lux-a.pk0019.g1 | 4.4 | 8.2 | 15.5 | 10.2 |  |  |  |
| lpxA lpxB rnhB dnaE | lux-a.pk061.c3 | 3.5 | 3.1 | 2.8 | 1.7 | 2.5 ug/ml | 1.82 | 3 |
|  | lux-a.pk061.c3 | 2.7 | 3.5 | 3.0 | 1.9 |  |  |  |
| oraA | lux-a.pk058.f5 | 5.1 | 7.9 | 5.9 | 3.9 | 10 ug/ml | 7.19 | 7 |
|  | lux-a.pk058.f5 | 4.7 | 7.7 | 5.6 | 3.8 |  |  |  |
| yaaF | lux-a.pk031.e7 | 2.1 | 2.0 | 1.3 | 1.0 | 2.5 ug/ml | 1.85 | 3 |
|  | lux-a.pk031.e7 | 2.0 | 2.1 | 1.8 | 1.5 |  |  |  |
| yigN | lux-a.pk046.f11 | 2.1 | 2.5 | 0.3 | 0.1 | 1.2 ug/ml | 2.54 | 5 |
|  | lux-a.pk046.f11 | 7.1 | 4.3 | 2.5 | 2.2 |  |  |  |
| Nalidixic acid upregulation not reproduced in liquid culture ||||||||
| frvR frvX frvB frvA | lux-a.pk046.e6 | 2.8 | 2.3 | 0.8 | 0.5 | 20 ug/ml | 1.46 | 0 |
|  | lux-a.pk046.e6 | 2.1 | 2.3 | 2.0 | 1.7 |  |  |  |
| yfhJ fdx hscA yfhE | lux-a.pk0019.g2 | 2.1 | 2.0 | 1.7 | 1.4 | 1.2 ug/ml | 1.02 | 0 |
|  | lux-a.pk0019.g2 | 2.1 | 2.2 | 1.5 | 1.3 |  |  |  |

TABLE 16

Mitomycin C and Nalidixic acid Responses in lexA+ and lexAind hosts

| Fusion to gene or operon: | Lux ID | Host Strain | NA Ratio, 2 hr 10 ug/ml | MitC Ratio, 2 hr 250 ng/ml |
|---|---|---|---|---|
| Known SOS regulon member: |||||
| dinG ybiB | lux-a.pk0024.f5 | lexA+ | 4.03 | 5.01 |
|  |  | lexAind | 0.97 | 1.15 |
| Nalidixic acid upregulated on both the solid LuxArray and in liquid culture New SOS regulon members |||||
| b1728 | lux-a.pk033.c5 | lexA+ | 5.17 | 8.97 |
|  | lux-a.pk033.c5 | lexAind | 0.40 | 0.90 |
| oraA | lux-a.pk058.f5 | lexA+ | 11.06 | 15.27 |
|  | lux-a.pk058.f5 | lexAind | 1.06 | 1.21 |
| yigN | lux-a.pk046.f11 | lexA+ | 5.74 | 9.84 |
|  | lux-a.pk046.f11 | lexAind | 0.59 | 0.93 |
| Nalidixic acid upregulated, not generally DNA damage inducible |||||
| b1169 | lux-a.pk0015.d6 | lexA+ | 3.22 | 1.12 |
|  | lux-a.pk0015.d6 | lexAind | 2.29 | 1.73 |
| b1936 | lux-a.pk0019.g1 | lexA+ | 3.25 | 1.22 |
|  | lux-a.pk0019.g1 | lexAind | 1.55 | 2.46 |
| lpxA lpxB rnhB dnaE | lux-a.pk061.c3 | lexA+ | 2.87 | 1.06 |
|  | lux-a.pk061.c3 | lexAind | 2.39 | 1.29 |
| yaaF | lux-a.pk031.e7 | lexA+ | 1.53 | 1.02 |
|  | lux-a.pk031.e7 | lexAind | 1.19 | 0.99 |
| Negative controls |||||
| yciG | lux-a.pk006.b4 | lexA+ | 0.32 | 0.56 |
|  |  | lexAind | 0.67 | 0.61 |
| lacZ | 65.d4 | lexA+ | 0.81 | 0.80 |
|  |  | lexAind | 1.05 | 1.24 |

Example 6

Additions to Collections and Alternative Methods of Generating Collections of Bacterial Genomic Fragments Fused to a Reporter There are several methods for making fusions of bacterial promoter regions to reporter genes to add to a genome-registered collection of randomly generated gene fusions. Some of these methods are also alternative methods for building a large collection of gene fusions.

Firstly, DNA sequence data from more random gene fusions will result in identification of additional useful members to a collection that is not completely saturated. These additional sequences can be generated from members of the same originally sequenced library of genetic fusions, LuxA for instance, or an independently generated library. The steps outlined in previous examples allow the genome registration of the newly sequenced fusions.

DNA sequencing of randomly generated fusions will lead to identification of fusions that would be useful except that the orientation of the chromosomal DNA is inverted, such that the promoter regions of interest are not operably linked to the reporter genes. Selecting such fusions and inverting the orientation of the insert DNA can significantly enhance the utility of a sequenced collection by adding many more operable linked fusion to the collections. A simple way to do this is to digest the plasmid DNA with a restriction enzyme that cuts just outside the cloned region and religate the pieces. Although a mixture of plasmids results from this procedure, in many cases the correctly oriented plasmid can be found because cells containing it, but not other possible products, will produce light. This method has the advantage of avoiding use of the polymerase chain reaction and thus avoiding possible changes in the DNA sequence from amplification.

This approach was demonstrated by identifying a non-operably linked clpB fusion in the Lux-A Collection, inverting the chromosomal DNA segment relative to the vector, and comparing an *E. coli* strain carrying the resultant plasmid to one in the collection with a proper orientation of the clpB promoter region. One isolate from the Lux-A Collection, lux-a.pk043.d3 contains the region of the *E. coli* chromosome with the clpB promoter, but is oriented in the opposite direction than required to operably link the promoter and reporter genes. Very low levels of light production of this strain were measured. In contrast, the strain, lux-a.pk054.c3, that carries the plasmid with the clpB promoter region in the proper orientation to operably link it to the luxCDABE reporters gene had a high level of light production. Plasmid DNA was isolated from lux-a.pk043.d3, digested with restriction enzyme XmaI, and ligated with T4 DNA ligase. The ligation reaction was used to transform *E. coli* strain DPD 1675 by electroporation. Transformants were selected by ampicillin resistance. Three percent of the resultant transformed colonies produced bioluminescence as detected by exposure of X-ray film. The response to ethanol treatment of two of these light producing transformants that putatively contain inverted chromosomal inserts, of lux-a.pk054.c3 (DPD2243) that contains a plasmid with the clpB promoter operably linked to the luxCDABE reporter and of the original lux-a.pk043.d3 were compared. Actively growing cultures at 37° C. in LB medium were treated with 4% ethanol and light production was quantitated at 37° C. using a microplate luminometer (Dynex ML3000). Table 17 summarizes the average bioluminescence of duplicate samples at 38 min after treatment.

TABLE 17

Light production by strains containing a clpB-luxCDABE gene fusion resulting from inversion of the chromosomal insert, and controls

| Strain | Culture turbidity[1] | Light production in LB[2] | Light production in LB + 4% ethanol[2] | Response Ratio |
|---|---|---|---|---|
| lux-a.pk043.d3 | 11 | 0.0015 | 0.0025 | N/A |
| inverted lux-a.pk043.d3 | 14 | 1.25 | 8.17 | 6.5 |

TABLE 17-continued

Light production by strains containing a clpB-luxCDABE gene fusion resulting from inversion of the chromosomal insert, and controls

| Strain | Culture turbidity[1] | Light production in LB[2] | Light production in LB + 4% ethanol[2] | Response Ratio |
|---|---|---|---|---|
| Inverted lux-a.pk043.d3 | 18 | 5.34 | 29.63 | 5.5 |
| lux-a.pk054.c3 (DPD2243) | 12 | 1.37 | 13.00 | 9.4 |

[1]At time zero; Klett units
[2]RLU

Thus, the presence of a promoter that drives transcription of the luxCDABE operon in the inverted isolates was shown by the light production in LB medium. Furthermore, the expected biological response of induction of up-regulation by ethanol treatment for this member of the heat shock regulon was also demonstrated.

This inverting method was implemented in a parallel manner to add gene fusions to the Lux-A Collection. First, a list of about 400 gene fusions from the Lux-A Collection that contained the correct genomic fragment but in the wrong orientation relative to the lux operon, and were not present in the current collection was derived. Each of the strains containing these fusions was picked out of the original collection of 8000 fusions and regrown. The bioluminescence of each was quantitated because, in some cases, the presence of a divergent promoter in the cloned DNA fragment resulted in light production even though the DNA was inverted with respect to the promoter of interest. About half of the selected strains produced >0.1 RLU of light following 3 hours of incubations at 37° C. after inoculation of 100 μl LB medium with 10 μl of culture from a working plate. This suggested that the set of strains with light production of <0.1 RLU would be easier to pursue initially. Thus, following isolation of plasmid DNA in a 96 well format, XmaI digestion, and religation, the ligation reaction mixes originating from strains with light production of less than 0.1 RLU were sorted into separate plates from those that originated from strains with light production greater than or equal to 0.1 RLU. *E. coli* DPD1675 was made competent by calcium chloride treatment and transformed with the religated plasmid DNA selecting for ampicillin resistance. Placing the petri plate with the transformant colonies on X-ray film and developing the exposed film at various time points of contact identified light producing transformants. The light producing colonies were purified by isolating single colonies in solidified LB medium containing ampicillin and light production was verified by luminometry. This process was completed for 36 plasmids isolated from strains with light production of less than 0.1 RLU. Plasmid DNA from each of the strains containing putative inverted chromosomal segments was isolated and DNA sequence was determined to assess if the inverted product had been obtained. Thirteen of the 36 plasmids yielded DNA sequence information that had a high scoring hit when compared with the *E. coli* genomic DNA sequence using BLASTN (default setting). Of these, five had DNA in the inverted orientation from the original clone.

There are several potential reasons for this relatively low success rate. For example, some promoters that are annotated may not be functional in the conditions used or may not be biologically relevant promoters. Thus, selection by light production of the inverted clone would not be successful. In contrast, divergent promoters that were not active in the liquid culture test for bioluminescence used for sorting may have been active on the solidified medium used to screen for light producing clones. This may have lead to selection of a colony containing the initial plasmid. Furthermore, there may have been poor plasmid DNA yield, poor cutting, and/or poor religations when done in parallel in microplates. This may have lead to DNA concentrations in the ligations such that intermolecular ligations were minimized or such that a low number of transformant colonies resulted and rare transformants with the inverted insert DNA were not represented. Thus, this approach of restriction digestion, religation, transformation and selection of light producing transformants has been demonstrated to work. However, further optimization for efficient parallel implementation is required.

To test inverting of a chromosomal segment in a plasmid containing divergent promoters, the backward fusion to yebF was chosen. Obtaining an operably linked reporter gene fusion to yebF was of particular interest because the yebF gene is an otherwise unknown open reading frame that was found in a DNA microarray experiment to be highly induced by mitomycin C, a DNA damaging agent. In this case, a divergent promoter to the purT gene was present in the chromosomal fragment and strains containing the backward yebF fusion produced light. Following XmaI digestion, religation and transformation, 10% of the transformants produced light. Of these, 20% (or 2% of the initial transformants) were found to be highly induced by nalidixic acid, another DNA damaging agent. This result strongly suggesting that the desired inversion of the chromosomal segment had occurred. This was verified by DNA sequence analysis. Thus, inverting chromosomal segments containing divergent promoters is possible and is facilitated if the two promoters can be distinguished by their biological activity.

An alternative inverting procedure uses plasmid DNA from clones requiring reorientation as templates for the polymerase chain reaction (PCR). Universal PCR primers were designed which hybridize specifically with the pDEW201 plasmid flanking the genomic fragment cloning site (Bam HI). Use of the first primer, pDEWE2S (SEQ ID NO:3, 5'-GGAATTGGGGATCGGAGCTCCCGGG-3'), an EcoRI site (GAATTC) is converted to a SacI site (GAGCTC) via an internal AT to GC mismatch. Use of the second primer, pDEWS2E (SEQ ID NO:4, 5'-GAATGGCGCGAATTCGGTACCCGGG-3'), results in the conversion of the SacI site to an EcoRI site via an internal GC to AT conversion. Thus the resultant PCR products from any pDEW201 clone can be digested with EcoRI and SacI and ligated into EcoRI- and SacI-digested pDEW201. The resultant plasmid contains the original chromosomal segment in the opposite orientation of the original clone, relative to the lux operon. As the primers are specific to the vector they can be used for all clones and are amenable to high throughput (96-well plate) approaches.

Construction, Sequencing and Registering an Additional Random Library of E. coli Genomic Fragments Fused to a luxCDABE Reporter.

An independent random library of E. coli genomic fragments in plasmid pDEW201 was constructed and called the LuxZ library. Chromosomal DNA isolated from E. coli strain W3110 (Ernsting et al., (1992) J. Bacteriol. 174:1109–1118) was partially digested with the restriction enzyme Sau3A1, size fractionated by agarose gel electrophoreses, and a fraction with an average size of approximately 0.7 KB isolated. This fraction was ligated to pDEW201 that had previously been digested with BamHI and treated with calf intestinal alkaline phosphatase. The ligation products were used to transform ultracompetent E. coli XL2Blue cells (Stratagene) to ampicillin resistance using the protocol provided by Stratagene. Preliminary characterization of individual XL2Blue transformants that were picked in random indicated that a large percentage (16 of 16) contained insert DNA with sizes ranging from 0.1 to 1.5 KB. Approximately 150,000 of these transformants were pooled and used as a source of heterogeneous LuxZ library plasmid DNA isolated using Qiagen tip20 columns (Qiagen Corp). This plasmid DNA pool was diluted 100-fold then used to transform E. coli DPD1675 (Van Dyk and LaRossa (1998) Methods in Molecular Biology: Bioluminescence Methods and Protocols, Humana Press inc. vol. 102:85–95) by electroporation. Electrocompetent DPD 1675 cells were prepared starting with 1 liter of LB culture at approximately $2.4 \times 10^8$ cells/ml. Following chilling on ice, the cells from this culture were collected by centrifugation at an average relative centrifugal force of 6,555 for 5 minutes. The cells were washed twice ice-cold, sterile distilled water (1 liter for the first wash and 500 ml for the second wash) and centrifuged. Then the cells were washed with 10 ml of ice-cold, sterile 10% glycerol in distilled water and centrifuged. The final resuspension of the cell pellet was done with ice-cold, sterile 10% glycerol in distilled water to yield a final volume of 2.1 ml. 55 $\mu$l aliquots were prepared, quick frozen in dry ice and ethanol, then stored at −80° C. until used. One such aliquot was thawed on ice, 1.0 $\mu$l of the diluted LuxZ library plasmid DNA was added, and the cells and plasmid DNA were transferred to an electroporation cuvette (Biorad, Gene Pulser®/E. coli Pulser™) on ice. The capped cuvette was electroporated with 1.85 volts at a capacitance of 25 $\mu$F then 0.5 ml of SOC medium (per liter: 20 g tryptone, 5 g yeast extract, 0.5 g NaCl, 2.5 mM KCl, 2.5 mM $MgCl_2$, 20 mM glucose, pH 7.0) was added. A 30 minute phenotypic expression time at 37° C. was used to minimize the presence of siblings. Following this incubation, 500 $\mu$l of 24% sterile glycerol in water was added and 100 $\mu$l aliquots were prepared, frozen on dry ice, and stored at −80° C. until used. These aliquots were thawed, plated on LB medium containing ampicillin, and 4608 single colonies were picked for use as inoculum for cultures grown in 80 $\mu$l 1× freezing medium (LB with 100 $\mu$g/ml ampicillin, 5.54% glycerol, 36 mM $K_2HPO_4$, 13.2 mM $KH_2PO_4$, 1.7 mM $NaC_6H_5O_7{:}2H_2O$, 40 mM $MgSO_4$, 6.8 mM $NH_4SO_4$) in the wells of 384 well microplates. These plates were stored at −80° C. until used for inoculation and growth to saturation in Terrific Broth (Gibco-BRL, Inc) containing 100 $\mu$g/ml ampicillin in 96 well deep-well plates. Plasmid DNA was extracted from the cultures using the Qiagen R.E.A.L.™ prep method with the following modification: after lysis of cells, the plates were placed in a boiling water bath for 5 minutes and then rapidly chilled in an ice-water bath before precipitation with Buffer R3. This modification prevented degradation of the plasmid DNA by the nucleases present in the non-endA host strain, DPD1675. DNA sequencing reactions were performed with approximately 1 $\mu$g of plasmid DNA under standard ABI Prism™ dRhodamine DyeTerminator Ready Reaction conditions with the primers pDEW201.forward (SEQ ID NO: 1, 5'-GGATCGGAATTCCCGGGGAT-3') and pDEW201.reverse (SEQ ID NO:2, 5'-CTGGCCGTTAATAATGAATG-3') to obtain sequence information from each end of the insert. DNA sequences were determined on ABI377™-XL 96-lane upgraded Sequencers under 4× run conditions on 5% PAG (polyacrylamide gel) LongRanger™ (FMC, Inc.) gels and analyzed with ABI software. DNA sequences were transferred to a UNIX based utility for further analysis. The homology search for the sequence from the beginning and end of each Lux-Z clone (in both orientations) and registration to the E. coli genome was done as described in Example 1 resulting in 1799 additional genome-registered gene fusions.

Example 7

Lux Array 1.04, a Genome-Wide, Promoter Activities Assay in Liquid Medium, and Its Use to Discover a Limonene Sensor.

Selection of Additional Non-Redundant lux Gene Fusions to Expand LuxArray 1.0.

Operably linked gene fusions were selected from the genome-registered LuxZ gene fusion collection described in Example 6 using the computational filter described in Example 5. This list was then compared with the current list of promoters contained in Lux Array 1.0 to eliminate redundancy. This process resulted in identification of 149 gene fusions useful to expand the LuxArray.

In addition, the five gene fusions generated by inversion of previously sequenced gene fusions as described in Example 6 and six gene fusions from other sources were added. Table 19 lists these additional 160 gene fusions that together with the gene fusions in LuxArray 1.0 yielded LuxArray 1.04. The 849 gene fusions in Lux Array 1.04 thus represent 33% of the 2584 known and predicted transcriptional units in the E. coli genome. Individual cultures of strains containing the newly identified gene fusions were added to empty wells of the existing microplate number 15 and new microplates numbered 17 to 19 were made with duplicated side by side symmetry. The former microplate 16 was eliminated because it contained only strains with the parental plasmid and sterile controls. Thus, the Lux Array 1.04 is contained in 18 microplates representing the cellular array. These were stored at −80° C. in freezing medium.

Limonene Stress of the Reporter Array in Liquid Culture.

Microplates from −80° C. containing the LuxArray 1.04 E. coli strains were thawed and used to inoculate 100 µl LB medium supplemented with 100 µg/ml ampicillin in Costar#3595 flat bottomed 96-well microplates. Following overnight growth at 37° C., the plates were visually examined and any wells with little or no turbidity were recorded. Then these cultures were diluted by transfer of 15 µl to 135 µl LB medium in Costar #3595, flat bottom 96-well microplates and were moderately swirl shaken on an IKA Schuttler MTS 4 shaker at setting 400 for two hrs at 37° C. in a humidified box. Twenty µl of each these actively growing cultures were transferred to the corresponding well in sets of three microplates, one containing 80 µl of LB medium, another containing 80 µl of LB medium saturated with limonene at room temperature, and the third containing 40 µl of LB medium saturated with limonene and 40 µl of LB medium. An initial (zero time) reading was taken using an MLX microplate luminometer (Dynex) pre-warmed to 37° C. Then the plates were placed at 37° C. without shaking. Additional bioluminescent measurements were taken at 45, 90, and 135 minutes. To limit the number of microplates handled each day, LuxArray 1.04 microplates 1 to 5, microplates 6 to 10, microplates 11 to 15, and microplates 17 to 19 were used on each of four different days.

Data Analysis of Limonene Induced Responses.

The data were normalized to correct for growth inhibition caused by limonene on the basis of each individual day that data was collected. The bioluminescence (RLU) of each individual culture for each day of experimentation under each of the three conditions, were added to determine the daily array total RLU. These were used to find a daily normalization factor (DNF) as follows:

$DNF$=Daily total array signal (time zero, $LB$ control)/Daily total array signal (time $x$, condition $y$)

Each measurement from the corresponding day, time point, and condition was multiplied by DNF to yield a normalized signal. The data from wells that were scored to have little or no growth were not used in further analysis. The normalized data were analyzed with GeneSpring (Silicon Genetics) software, which averaged the signal from each of the duplicate cultures for each reporter gene fusion.

Overall, there was little to no upregulation of gene expression under the condition of 40% saturated limonene in LB medium. Thus, patterns of gene expression from the 80% saturated limonene in LB medium were further examined. Lists were made of gene fusions that were upregulated by 2 fold or more at each time point. These lists were examined and gene fusions with very low normalized RLU values (<0.012 RLU) at all conditions were eliminated. The upregulated gene fusions are listed in Table 20, which uses the name of the gene in each operon with the smallest b# to identify each gene fusion. The designation of ">2x" is given for upregulation while "*" is listed if the expression was less than 2 fold increased. At 45 minutes, the expression of fourteen gene fusions was increased; none of these was increased 3 fold or higher. At 90 minutes, 37 gene fusions were induced; these included all but one of the gene fusions observed at 45 minutes. However, the most highly upregulated gene fusions at 90 minutes were not previously observed to be upregulated at 45 minutes. These were fusions of the luxCDABE reporter to the promoter regions of uhpT (3.8x), nirB (3.7x) and narK (3.6x). At 135 minutes, 39 gene fusions were induced, which included 13 fusions not observed at 45 or 90 minutes. At this time point, the most highly upregulated gene fusions were those to the promoter regions of uhpT (7.7x), nirB (4.1x) and katG (4.1x). Thus, the gene fusion to the promoter region of uhpT was the most highly upregulated at both the 90 and 135 minute time points.

Verification of uhpT-lux Upregulation by Limonene.

E. coli strain DPD3228 is identical to lux-a.pk034.b9 the strain containing the uhpT-luxCDABE gene fusion. This strain was grown overnight at 37° C. in LB medium containing 100 µg/ml ampicillin and diluted the following day into LB medium and grown to log phase at 37° C. 20 µl aliquots of this culture were added to 80 µl of LB medium saturated with limonene, to 80 µl of a series of two fold dilutions into LB medium of LB saturated with limonene, and to 80 µl of LB medium. Light production was measured in a Luminoskan Ascent (Labsystems) microplate luminometer at 37° C. FIG. 10 shows the result. Similar to the initial LuxArray observations, a late response to the presence of limonene was observed. This response was maximal at the highest concentration of limonene tested, but was also detected when limonene was present at 40% or 20% of saturating amounts in LB medium. Thus, the upregulation of bioluminescence from this strain by limonene was confirmed, demonstrating its utility as a sensor for limonene.

---

Scheme 1: PERL script used to filter the lux clone collection for functional reporter constructs

```
#Filename:luxfilter2
#This perl script is designed to compare an operon list
#containing genome coordinates and directionality
#and clone ID to a list of clones containing the same and output
```

Scheme 1: PERL script used to filter the lux clone collection for functional reporter constructs

```perl
#their intersect to a new file
open (OPERONS, "< operons_gg.txt") || die "can't open operon list: $!";
open (OUTPUT, "> full_list2.txt") || die "can't open output file: $!";
open (CLONES, "< luxclones.txt") || die "can't open clone list: $!";
@clones = <CLONES>;
close CLONES;
while ($line = <OPERONS>) {
    print OUTPUT $line;
    print $line;
    if ($line =~ /complement/) {
        ($start) = $line =~ /\d+\.\.(\d+)/;
        ($op_end) = $line =~ /(\d+)\.\.\d+/;
        $promoter = $start+50;
        foreach $clone (@clones) {
            if ($clone =~ /\t-\t/) {
                ($clone_start) = $clone =~ /\d+\t(\d+)\t\d+/;
                ($clone_end) = $clone =~ /(\d+) \t\d+\t\d+/;
                if (($clone_start > $promoter) &&
                    ($clone_end > $op_end) &&
                    ($clone_end < $start)) {
                    print OUTPUT $clone;
                    print $clone;
                }
            }
        }
    } else {
        ($start) = $line =~ /(\d+)\.\.\d+/;
        ($op_end) = $line =~ /\d+\.\.(\d+)/;
        $promoter = $start-50;
        foreach $clone (@clones) {
            if ($clone =~ /\+/) {
                ($clone_start) = $clone =~ /(\d+)\t\d+\t\d+/;
                ($clone_end) = $clone =~ /\d+\t(\d+)\t\d+/;
                if (($promoter > $clone_start) &&
                    ($clone_end < $op_end) &&
                    ($clone_end > $start)) {
                    print OUTPUT $clone;
                    print $clone;
                }
            }
        }
    }
}
close OUTPUT;
close OPERONS;
```

TABLE 18

Luxarray 1.0 Clone Collection

| Lux ID | Coding strand | Operon |
|---|---|---|
| lux-lacZ | − | complement(360473 . . . 365529) |
| lux-a.pk007.b9 | − | Operon complement(3399029 . . . 3400969)/note = "predicted operon"/note = "ordered genes contained in the operon: yhdA" |
| lux-a.pk0017.h6 | + | Operon (510865 . . . 513092)/note = "predicted operon"/note = "ordered genes contained in the operon: b0485 b0486" |
| lux-a.pk0022.c6 | − | Operon complement(2325387 . . . 2334712)/note = "predicted operon"/note = "ordered genes contained in the operon: b2225 b2226 b2227 b2228 b2229 yfaA" |
| lux-a.pk0026.g3 | − | Operon complement(120178 . . . 121551)/note = "documented aroP operon" |
| lux-a.pk0032.g2 | + | Operon (4161218 . . . 4171626)/note = "predicted operon"/note = "ordered genes contained in the operon: btuB murI murB birA" |
| lux-a.pk0037.d11 | − | Operon complement(1067734 . . . 1073234)/note = "predicted operon"/note = "ordered genes contained in the operon: b1006 b1007 b1008 b1009 b1010 b1011 b1012" |
| lux-a.pk0041.f10 | + | Operon (342108 . . . 343157)/note = "predicted operon"/note = "ordered genes contained in the operon: b0325" |
| lux-a.pk047.d10 | − | Operon complement(4592507 . . . 4593313)/note = "predicted operon"/note = "ordered genes contained in the operon: yjjM" |
| lux-a.pk052.f3 | + | Operon (3246594 . . . 3248016)/note = "predicted operon"/note = "ordered genes contained in the operon: yqjC yqjD |

TABLE 18-continued

Luxarray 1.0 Clone Collection

| Lux ID | Coding strand | Operon |
|---|---|---|
| | | yqjE b3100" |
| lux-a.pk058.f5 | − | Operon complement(2820162 . . . 2820662)/note = "predicted operon"/note = "ordered genes contained in the operon: oraA" |
| lux-a.pk066.a3 | − | Operon complement(1998496 . . . 2001629)/note = "predicted operon"/note = "ordered genes contained in the operon: fliZ fliA fliC" |
| lux-a.pk072.e2 | + | Operon (2543793 . . . 2547426)/note = "predicted operon"/note = "ordered genes contained in the operon: b2428 b2429 b2430" |
| lux-a.pk078.c5 | − | Operon complement(3117613 . . . 3119295)/note = "predicted operon"/note = "ordered genes contained in the operon: b2975" |
| lux-a.pk086.e2 | − | Operon complement(4311389 . . . 4322743)/note = "documented phnCDE-b4103-phnFGHIJKLMNOPQ operon" |
| lux-a.pk0001.a11 | − | Operon complement(1734145 . . . 1735314)/note = "predicted operon"/note = "ordered genes contained in the operon: b1657" |
| lux-a.pk007.c1 | − | Operon complement(2255449 . . . 2257316)/note = "predicted operon"/note = "ordered genes contained in the operon: yeiN yeiC" |
| lux-a.pk0018.a4 | + | Operon (3714927 . . . 3715913)/note = "predicted operon"/note "ordered genes contained in the operon: yiaE" |
| lux-a.pk0022.d3 | + | Operon (801110 . . . 802543)/note = "predicted operon"/note = "ordered genes contained in the operon: b0770" |
| lux-a.pk026.e11 | + | Operon (84191 . . . 87848)/note = "documented leuO-ilvIH operon" |
| lux-a.pk032.g4 | + | Operon (214291 . . . 215979)/note = "predicted operon"/note = "ordered genes contained in the operon: yaeQ yaeJ cutF" |
| lux-a.pk037.d4 | + | Operon (89634 . . . 103153)/note = "predicted operon"/note = "ordered genes contained in the operon: yabB yabC ftsL ftsI murE murF mraY murD ftsW murG murC ddlB" |
| lux-a.pk041.f12 | + | Operon (3542470 . . . 3543201)/note = "predicted operon"/note = "ordered genes contained in the operon: yhgH" |
| lux-a.pk047.d4 | − | Operon complement(3334190 . . . 3334459)/note = "predicted operon"/note = "ordered genes contained in the operon: yrbA" |
| lux-a.pk052.g10 | + | Operon (4233811 . . . 4237309)/note = "predicted operon"/note = "ordered genes contained in the operon: yjbF yjbG yjbH" |
| lux-a.pk058.h10 | − | Operon complement(578407 . . . 578859)/note = "predicted operon"/note = "ordered genes contained in the operon: b0558" |
| lux-a.pk066.b10 | − | Operon complement(4297143 . . . 4300516)/note = "predicted operon"/note = "ordered genes contained in the operon: yjcP yjcQ" |
| lux-a.pk072.e3 | + | Operon (797809 . . . 7988040 /note = "predicted operon"/note = "ordered genes contained in the operon: ybhE" |
| lux-a.pk078.d2 | − | Operon complement(1336594 . . . 1337184)/note = "predicted operon"/note = "ordered genes contained in the operon: ribA" |
| lux-a.pk086.h2 | − | Operon complement(3390094 . . . 3393895)/note = "predicted operon"/note = "ordered genes contained in the operon: yhdP yhdR" |
| lux-lacZ | | complement(360473 . . . 365529) |
| lux-a.pk007.d12 | − | Operon complement(2111456 . . . 2112349)/note = "predicted operon"/note = "ordered genes contained in the operon: galF" |
| lux-a.pk0018.a6 | + | Operon (4140109 . . . 4141523)/note = "predicted operon"/note = "ordered genes contained in the operon: frwC frwB" |
| lux-a.pk0022.g11 | + | Operon (2693959 . . . 2695377)/note = "predicted operon"/note = "ordered genes contained in the operon: yfhD" |
| lux-a.pk027.b11 | − | Operon complement(3598659 . . . 3601874)/note = "documented ftsYEX operon" |
| lux-a.pk032.h3 | + | Operon (274525 . . . 276871)/note = "predicted operon"/note = "ordered genes contained in the operon: b0260 b0261" |
| lux-a.pk037.d6 | + | Operon (4401964 . . . 4402161)/note = "predicted operon"/note = "ordered genes contained in the operon: b4176" |
| lux-a.pk041.g11 | − | Operon complement(2904665 . . . 2905963)/note = "predicted operon"/note = "ordered genes contained in the operon: eno" |
| lux-a.pk047.e10 | + | Operon (4152580 . . . 4155802)/note = "documented argCBH operon" |
| lux-a.pk052.g3 | − | Operon complement(3852741 . . . 3853934)/note = "predicted operon"/note = "ordered genes contained in the operon: yidF yidG yidH" |

TABLE 18-continued

Luxarray 1.0 Clone Collection

| Lux ID | Coding strand | Operon |
|---|---|---|
| lux-a.pk059.a8 | + | Operon (621523 . . . 622773)/note = "predicted operon"/note = "ordered genes contained in the operon: ybdA" |
| lux-a.pk066.b12 | + | Operon (284619 . . . 287623)/note = "predicted operon"/note = "ordered genes contained in the operon: b0270 b0271" |
| lux-a.pk072.f11 | − | Operon complement(2061410 . . . 2063786)/note = "documented cobUST operon" |
| lux-a.pk078.d7 | − | Operon complement(3092119 . . . 3093144)/note = "predicted operon"/note = "ordered genes contained in the operon: b2950" |
| lux-a.pk087.b5 | − | Operon complement(1952602 . . . 1956156)/note = "predicted operon"/note = "ordered genes contained in the operon: bisZ b1873" |
| lux-a.pk0001.a2 | − | Operon complement(3767870 . . . 3769371)/note = "predicted operon"/note = "ordered genes contained in the operon: yibH yibI" |
| lux-a.pk007.d2 | − | Operon complement(2506481 . . . 2507446)/note = "predicted operon"/note = "ordered genes contained in the operon: glk" |
| lux-a.pk0018.b1 | + | Operon (4048927 . . . 4049436)/note = "predicted operon"/note = "ordered genes contained in the operon: yihI" |
| lux-a.pk0022.g7 | − | Operon complement(783105 . . . 784046)/note = "predicted operon"/note = "ordered genes contained in the operon: b0752" |
| lux-a.pk027.c11 | + | Operon (1779419 . . . 1782701)/note = "predicted operon"/note = "ordered genes contained in the operon: b1699 b1700 ydiD" |
| lux-a.pk033.a3 | − | Operon complement(1978212 . . . 1980411)/note = "documented otsAB operon" |
| lux-a.pk037.e3 | − | Operon complement(3290116 . . . 3290976)/note = "predicted operon"/note = "ordered genes contained in the operon: yraL" |
| lux-a.pk041.g5 | − | Operon complement(1551996 . . . 1553720)/note = "predicted operon"/note = "ordered genes contained in the operon: sfcA" |
| lux-a.pk047.e11 | + | Operon (2932257 . . . 2938121)/note = "documented fucPIKUR operon" |
| lux-a.pk052.g6 | − | Operon complement(317900 . . . 319252)/note = "predicted operon"/note = "ordered genes contained in the operon: b0304" |
| lux-a.pk059.b4 | − | Operon complement(3302214 . . . 3303458)/note = "documented mtr operon" |
| lux-a.pk066.c7 | + | Operon (87860 . . . 89032)/note = "predicted operon"/note = "ordered genes contained in the operon: fruL fruR" |
| lux-a.pk072.f2 | − | Operon complement(3553466 . . . 3555711)/note = "predicted operon"/note = "ordered genes contained in the operon: yhgJ yhgK yhgL" |
| lux-a.pk078.d9 | + | Operon (4257900 . . . 4258885)/note = "predicted operon"/note = "ordered genes contained in the operon: yjbL yjbM" |
| lux-a.pk087.b7 | + | Operon (594823 . . . 596196)/note = "predicted operon"/note = "ordered genes contained in the operon: b0572" |
| lux-lacZ | | complement(360473 . . . 365529) |
| lux-a.pk007.d3 | + | Operon (794312 . . . 796835)/note = "documented modABC operon" |
| lux-a.pk0018.b10 | + | Operon (1635056 . . . 1635481)/note = "predicted operon"/note = "ordered genes contained in the operon: b1549" |
| lux-a.pk0022.h4 | + | Operon (816267 . . . 818970)/note = "documented moaABCDE operon" |
| lux-a.pk027.d12 | + | Operon (1879936 . . . 1881021)/note = "predicted operon"/note = "ordered genes contained in the operon: b1800" |
| lux-a.pk033.a4 | + | Operon (4213057 . . . 4217911)/note = "documented aceBAK operon" |
| lux-a.pk037.e6 | + | Operon (2232053 . . . 2234520)/note = "predicted operon"/note = "ordered genes contained in the operon: b2146 yeiA" |
| lux-a.pk041.h8 | + | Operon (2493599 . . . 2494585)/note = "predicted operon"/note = "ordered genes contained in the operon: b2378" |
| lux-a.pk047.e8 | − | Operon complement(2239830 . . . 2241672)/note = "predicted operon"/note = "ordered genes contained in the operon: yeiB folE" |
| lux-a.pk052.h2 | − | Operon complement(3748758 . . . 3749498)/note = "predicted operon"/note = "ordered genes contained in the operon: yiaT" |
| lux-a.pk059.c12 | − | Operon complement(3944752 . . . 3945590)/note = "predicted operon"/note = "ordered genes contained in the operon: yifA pssR" |
| lux-a.pk066.c9 | + | Operon (3500404 . . . 3502421)/note = "predicted operon"/note = "ordered genes contained in the operon: yhfP yhfQ yhfR" |
| lux-a.pk072.f7 | − | Operon complement(1577657 . . . 1580581)/note = "predicted |

TABLE 18-continued

Luxarray 1.0 Clone Collection

| Lux ID | Coding strand | Operon |
|---|---|---|
| | | operon"/note = "ordered genes contained in the operon: b1497 b1498" |
| lux-a.pk078.e3 | + | Operon (2680877 . . . 2682076)/note = "predicted operon"/note = "ordered genes contained in the operon: b2550" |
| lux-a.pk087.c1 | − | Operon complement(1234932 . . . 1236464)/note = "predicted operon"/note = "ordered genes contained in the operon: ycgB" |
| lux-a.pk0001.b6 | − | Operon complement(4268628 . . . 4271450)/note = "documented uvrA operon" |
| lux-a.pk007.e12 | + | Operon (4248534 . . . 4249862)/note = "predicted operon"/note = "ordered genes contained in the operon: yjbI" |
| lux-a.pk0018.c7 | − | Operon complement(2245083 . . . 2246552)/note = "predicted operon"/note = "ordered genes contained in the operon: lysP" |
| lux-a.pk0022.h5 | + | Operon (2363915 . . . 2371298)/note = "predicted operon"/note = "ordered genes contained in the operon: b2253 b2254 b2255 b2256 b2257 b2258" |
| lux-a.pk027.e11 | − | Operon complement(1762958 . . . 1766709)/note = "predicted operon"/note = "ordered genes contained in the operon: b1685 b1686 b1687" |
| lux-a.pk033.a6 | + | Operon (3676830 . . . 3677978)/note = "predicted operon"/note = "ordered genes contained in the operon: kdgK" |
| lux-a.pk037.e9 | − | Operon complement(2097884 . . . 2099290)/note = "predicted operon"/note = "ordered genes contained in the operon: gnd" |
| lux-a.pk042.a6 | − | Operon complement(4228938 . . . 4229210)/note = "predicted operon"/note = "ordered genes contained in the operon: yjbD" |
| lux-a.pk047.f2 | − | Operon complement(280053 . . . 281207)/note = "predicted operon"/note = "ordered genes contained in the operon: yagA" |
| lux-a.pk052.h9 | − | Operon complement(2769861 . . . 2770706)/note = "predicted operon"/note = "ordered genes contained in the operon: b2638 b2639" |
| lux-a.pk060.a10 | + | Operon (3432844 . . . 3435531)/note = "predicted operon"/note = "ordered genes contained in the operon: fmu trkA" |
| lux-a.pk066.d11 | + | Operon (4411838 . . . 44134780)/note = "predicted operon"/note "ordered genes contained in the operon: aidB" |
| lux-a.pk072.g1 | + | Operon (3483757 . . . 3484389)/note = "documented crp operon" |
| lux-a.pk078.f11 | + | Operon (3491648 . . . 3496838)/note = "documented nirBDC-cysG operon" |
| lux-a.pk087.c4 | − | Operon complement(1232399 . . . 1233940)/note = "predicted operon"/note = "ordered genes contained in the operon: nhaB" |
| lux-a.pk0001.c2 | − | Operon complement(1694486 . . . 1695076)/note = "predicted operon"/note = "ordered genes contained in the operon: gusR" |
| lux-a.pk007.e7 | + | Operon (2837547 . . . 2840437)/note = "documented ascFB operon" |
| lux-a.pk0018.d2 | − | Operon complement(605488 . . . 606606)/note = "predicted operon"/note = "ordered genes contained in the operon: b0581" |
| lux-a.pk0023.c11 | + | Operon (2088214 . . . 2095247)/note = "documented hisGDCBHAFI operon" |
| lux-a.pk027.e3 | − | Operon complement(344890 . . . 345561)/note = "predicted operon"/note = "ordered genes contained in the operon: b0328" |
| lux-a.pk033.c5 | + | Operon (1808223 . . . 1808825)/note = "predicted operon"/note = "ordered genes contained in the operon: b1728" |
| lux-a.pk037.f1 | − | Operon complement(2474714 . . . 2475649)/note = "documented dsdC operon" |
| lux-a.pk042.b3 | − | Operon complement(1838807 . . . 1839433)/note = "predicted operon"/note = "ordered genes contained in the operon: b1758" |
| lux-a.pk047.f7 | + | Operon (2861616 . . . 2863035)/note = "predicted operon"/note = "ordered genes contained in the operon: b2738 b2739" |
| lux-a.pk053.b5 | − | Operon complement(464836 . . . 466536)/note = "predicted operon"/note = "ordered genes contained in the operon: ybaE" |
| lux-a.pk060.a6 | + | Operon (2775136 . . . 2775803)/note = "predicted operon"/note = "ordered genes contained in the operon: b2645 b2646" |
| lux-a.pk066.f11 | − | Operon complement(820765 . . . 823720)/note = "predicted operon"/note = "ordered genes contained in the operon: b0788 b0789 b0790" |
| lux-a.pk072.g5 | + | Operon (1418389 . . . 1421668)/note = "predicted operon"/ |

TABLE 18-continued

Luxarray 1.0 Clone Collection

| Lux ID | Coding strand | Operon |
|---|---|---|
| | | note = "ordered genes contained in the operon: b1357 b1358 b1359 b1360 b1361 b1362" |
| lux-a.pk079.b10 | + | Operon complement(177001 . . . 179153)/note = "predicted operon"/note = "ordered genes contained in the operon: yadS yadT pfs" |
| lux-a.pk087.c6 | − | Operon complement(2992482 . . . 2993114)/note = "predicted operon"/note = "ordered genes contained in the operon: b2855 b2856" |
| lux-a.pk0001.c7 | + | Operon (2857783 . . . 2858439)/note = "predicted operon"/note = "ordered genes contained in the operon: b2734" |
| lux-a.pk007.f11 | − | Operon complement(4429669 . . . 4430643)/note = "predicted operon"/note = "ordered genes contained in the operon: ytfF" |
| lux-a.pk0018.d7 | − | Operon complement(3077663 . . . 3079654)/note = "predicted operon"/note = "ordered genes contained in the operon: tktA" |
| lux-a.pk023.c3 | + | Operon (3632372 . . . 3633523)/note = "predicted operon"/note = "ordered genes contained in the operon: yhiM" |
| lux-a.pk027.e7 | + | Operon (997713 . . . 1003880)/note = "predicted operon"/note = "ordered genes contained in the operon: b0939 b0940 b0941 b0942 b0943 ycbF" |
| lux-a.pk033.d5 | + | Operon (4100373 . . . 4101077)/note = "predicted operon"/note = "ordered genes contained in the operon: yiiM" |
| lux-a.pk037.f5 | − | Operon complement(2908778 . . . 2909361)/note = "predicted operon"/note = "ordered genes contained in the operon: chpA chpR" |
| lux-a.pk042.b7 | + | Operon (3237584 . . . 3238828)/note = "predicted operon"/note = "ordered genes contained in the operon: ygjU" |
| lux-a.pk047.g9 | + | Operon complement(2083726 . . . 2085090)/note = "predicted operon"/note = "ordered genes contained in the operon: yeeF" |
| lux-a.pk053.b8 | + | Operon (3841591 . . . 3843357)/note = "predicted operon"/note = "ordered genes contained in the operon: yicP" |
| lux-a.pk060.b12 | − | Operon complement(1325791 . . . 1327136)/note = "predicted operon"/note = "ordered genes contained in the operon: btuR yciK" |
| lux-a.pk066.g9 | − | Operon complement(1889349 . . . 1891259)/note = "predicted operon"/note = "ordered genes contained in the operon: b1808" |
| lux-a.pk073.a11 | − | Operon complement(439426 . . . 440567)/note = "documented xseB-ispA operon" |
| lux-a.pk079.e5 | − | Operon complement(346081 . . . 347667)/note = "predicted operon"/note = "ordered genes contained in the operon: b0330" |
| lux-a.pk087.d4 | + | Operon (252005 . . . 253161)/note = "predicted operon"/note = "ordered genes contained in the operon: yafN yafO yafP" |
| lux-a.pk0001.d10 | − | Operon complement(2591092 . . . 2594757)/note = "predicted operon"/note = "ordered genes contained in the operon: b2473 b2474 b2475" |
| lux-a.pk008.c11 | − | Operon complement(2420669 . . . 2421559)/note = "predicted operon"/note = "ordered genes contained in the operon: b2305" |
| lux-a.pk0018.f1 | + | Operon (980270 . . . 982117)/note = "predicted operon"/note = "ordered genes contained in the operon: ycbB" |
| lux-a.pk0023.c6 | + | Operon (774376 . . . 778255)/note = "documented to1QRAB operon" |
| lux-a.pk027.f6 | − | Operon complement(691097 . . . 692640)/note = "predicted operon"/note = "ordered genes contained in the operon: b0659 b0660" |
| lux-a.pk033.e12 | − | Operon complement(2112524 . . . 2116426)/note = "predicted operon"/note = "ordered genes contained in the operon: b2043 b2044 b2045" |
| lux-a.pk037.h4 | − | Operon complement(4343258 . . . 4344904)/note = "documented fumB operon" |
| lux-a.pk042.c7 | + | Operon (3416786 . . . 3418859)/note = "predicted operon"/note = "ordered genes contained in the operon: yhdW yhdX" |
| lux-a.pk048.c7 | + | Operon (384399 . . . 387870)/note = "predicted operon"/note = "ordered genes contained in the operon: b0365 b0366 b0367 b0368" |
| lux-a.pk053.d10 | + | Operon (4010643 . . . 4012904)/note = "documented metE operon" |
| lux-a.pk060.b6 | + | Operon (4349421 . . . 4349935)/note = "predicted operon"/note = "ordered genes contained in the operon: yjdI yjdJ" |
| lux-a.pk067.b10 | − | Operon complement(2254105 . . . 2255355)/note = "predicted operon"/note = "ordered genes contained in the operon: yeiM" |

TABLE 18-continued

Luxarray 1.0 Clone Collection

| Lux ID | Coding strand | Operon |
|---|---|---|
| lux-a.pk073.d7 | − | Operon complement(1990897 . . . 1992663)/note = "predicted operon"/note = "ordered genes contained in the operon: uvrC" |
| lux-a.pk079.f10 | − | Operon complement(4452185 . . . 4453183)/note = "predicted operon"/note = "ordered genes contained in the operon: fbp" |
| lux-a.pk087.e2 | + | Operon (2278652 . . . 2280412)/note = "predicted operon"/note = "ordered genes contained in the operon: yejH" |
| lux-a.pk0001.f10 | − | Operon complement(59687 . . . 63264)/note = "predicted operon"/note = "ordered genes contained in the operon: yabO hepA" |
| lux-a.pk008.e12 | + | Operon (71351 . . . 72115)/note = "predicted operon"/note = "ordered genes contained in the operon: yabI" |
| lux-a.pk0018.f11 | + | Operon (2890237 . . . 2892794)/note = "predicted operon"/note = "ordered genes contained in the operon: b2765 b2766 b2767 b2768" |
| lux-a.pk0023.d2 | + | Operon (15445 . . . 16557)/note = "predicted operon"/note = "ordered genes contained in the operon: yi81_1" |
| lux-a.pk027.h4 | − | Operon complement(4590931 . . . 4592292)/note = "predicted operon"/note = "ordered genes contained in the operon: yjiZ" |
| lux-a.pk033.e2 | + | Operon (471822 . . . 473476)/note = "predicted operon"/note = "ordered genes contained in the operon: glnK amtB" |
| lux-a.pk037.h9 | − | Operon complement(904963 . . . 906012)/note = "predicted operon"/note = "ordered genes contained in the operon: b0868" |
| lux-a.pk042.c8 | + | Operon (3208422 . . . 3212529)/note = "documented rpsU-dnaG-rpoD operon" |
| lux-a.pk048.d11 | − | Operon complement(1844989 . . . 1846032)/note = "documented selD operon" |
| lux-a.pk053.d5 | + | Operon (4414530 . . . 4415279)/note = "predicted operon"/note = "ordered genes contained in the operon: yjfP" |
| lux-a.pk060.e5 | + | Operon (3344219 . . . 3345879)/note = "predicted operon"/note = "ordered genes contained in the operon: ptsN b3205 ptsO" |
| lux-a.pk067.d11 | − | Operon complement(2715511 . . . 2716548)/note = "predicted operon"/note = "ordered genes contained in the operon: yfiF" |
| lux-a.pk073.f10 | + | Operon (3637741 . . . 3638175)/note = "predicted operon"/note = "ordered genes contained in the operon: uspA" |
| lux-a.pk079.f4 | + | Operon (234798 . . . 235538)/note = "predicted operon"/note = "ordered genes contained in the operon: b0213" |
| lux-a.pk087.f10 | − | Operon complement(4308686 . . . 4309621)/note = "predicted operon"/note = "ordered genes contained in the operon: yjcX" |
| lux-a.pk0001.f2 | − | Operon complement(2426077 . . . 2429677)/note = "documented dedD-cvpA-purF-ubiX operon" |
| lux-a.pk009.a4 | + | Operon (3579494 . . . 3581811)/note = "predicted operon"/note = "ordered genes contained in the operon: yhhZ b3443 insA_5 insB_5" |
| lux-a.pk0018.g6 | + | Operon (2415080 . . . 2416621)/note = "predicted operon"/note = "ordered genes contained in the operon: b2298" |
| lux-a.pk0023.e3 | + | Operon (3223875 . . . 3225308)/note = "predicted operon"/note = "ordered genes contained in the operon: ygjI" |
| lux-a.pk028.g6 | − | Operon complement(3663810 . . . 3665210)/note = "predicted operon"/note = "ordered genes contained in the operon: gadA" |
| lux-a.pk033.e6 | − | Operon complement(3825087 . . . 3826292)/note = "predicted operon"/note = "ordered genes contained in the operon: gltS" |
| lux-a.pk038.a4 | − | Operon complement(3623310 . . . 3628232)/note = "predicted operon"/note = "ordered genes contained in the operon: yhhJ yhiG yhiI" |
| lux-a.pk042.d9 | + | Operon (1864932 . . . 1866866)/note = "predicted operon"/note = "ordered genes contained in the operon: b1783" |
| lux-a.pk048.g4 | + | Operon (3029318 . . . 3030835)/note = "predicted operon"/note = "ordered genes contained in the operon: b2888" |
| lux-a.pk053.d8 | − | Operon complement(2523950 . . . 2524876)/note = "predicted operon"/note = "ordered genes contained in the operon: b2409" |
| lux-a.pk060.e8 | − | Operon complement(740298 . . . 741779)/note = "predicted operon"/note = "ordered genes contained in the operon: b0709" |
| lux-a.pk067.f8 | − | Operon complement(1921389 . . . 1922993)/note = "predicted operon"/note = "ordered genes contained in the operon: b1839 b1840 b1841" |
| lux-a.pk073.f3 | − | Operon complement(1515906 . . . 1516870)/note = "predicted operon"/note = "ordered genes contained in the operon: |

TABLE 18-continued

Luxarray 1.0 Clone Collection

| Lux ID | Coding strand | Operon |
|---|---|---|
| | | b1447 b1448" |
| lux-a.pk079.g6 | − | Operon complement(988377 . . . 989579)/note = "documented pncB operon" |
| lux-a.pk087.g3 | − | Operon complement(3475544 . . . 3476134)/note = "predicted operon"/note = "ordered genes contained in the operon: slyD" |
| lux-a.pk0002.b12 | + | Operon (484985 . . . 485632)/note = "predicted operon"/note = "ordered genes contained in the operon: acrR" |
| lux-a.pk009.a9 | − | Operon complement(232597 . . . 233955)/note = "predicted operon"/note = "ordered genes contained in the operon: dniR" |
| lux-a.pk0018.h2 | + | Operon (3782887 . . . 3785724)/note = "predicted operon"/note = "ordered genes contained in the operon: yibO yibP" |
| lux-a.pk023.f2 | − | Operon complement(2030406 . . . 2031524)/note = "predicted operon"/note = "ordered genes contained in the operon: yedJ b1963" |
| lux-a.pk029.b2 | + | Operon (3972208 . . . 3978309)/note = "predicted operon"/note = "ordered genes contained in the operon: yifH yifI yifJ rffT rffM" |
| lux-a.pk033.f3 | + | Operon (945094 . . . 947882)/note = "predicted operon"/note = "ordered genes contained in the operon: ycaD b0899" |
| lux-a.pk038.b10 | + | Operon (1036963 . . . 1041138)/note = "documented appCBA operon" |
| lux-a.pk042.e10 | − | Operon complement(3464797 . . . 3467490)/note = "predicted operon"/note = "ordered genes contained in the operon: yheB" |
| lux-a.pk049.a4 | − | Operon complement(1946774 . . . 1948546)/note = "predicted operon"/note = "ordered genes contained in the operon: aspS" |
| lux-a.pk053.e9 | − | Operon complement(2077555 . . . 2078613)/note = "predicted operon"/note = "ordered genes contained in the operon: yeeA" |
| lux-a.pk060.g1 | − | Operon complement(1823979 . . . 1830006)/note = "predicted operon"/note = "ordered genes contained in the operon: b1744 b1745 b1746 b1747 b1748" |
| lux-a.pk068.a3 | − | Operon complement(926697 . . . 930185)/note = "documented cydCD operon" |
| lux-a.pk073.h2 | + | Operon (3646158 . . . 3648292)/note = "documented arsRBC operon" |
| lux-a.pk079.h9 | − | Operon complement(1532989 . . . 1533882)/note = "predicted operon"/note = "ordered genes contained in the operon: yddE" |
| lux-a.pk088.c3 | − | Operon complement(264844 . . . 266191)/note = "predicted operon"/note = "ordered genes contained in the operon: b0250 b0251" |
| lux-lacZ | | complement(360473 . . . 365529) |
| lux-a.pk009.b2 | − | Operon complement(1397745 . . . 1402604)/note = "predicted operon"/note = "ordered genes contained in the operon: ogt ydaH b1337 b1338" |
| lux-a.pk0019.a12 | − | Operon complement(3065360 . . . 3066100)/note = "predicted operon"/note = "ordered genes contained in the operon: yggE" |
| lux-a.pk0023.h6 | − | Operon complement(1797417 . . . 1800594)/note = "documented thrS-infC-rpmI-rplT operon" |
| lux-a.pk029.b8 | − | Operon complement(3487903 . . . 3489257)/note = "predicted operon"/note = "ordered genes contained in the operon: pabA fic yhfG" |
| lux-a.pk033.f6 | + | Operon (2380733 . . . 2381944)/note = "predicted operon"/note = "ordered genes contained in the operon: b2269" |
| lux-a.pk038.b6 | + | Operon (601182 . . . 602558)/note = "predicted operon"/note = "ordered genes contained in the operon: pheP" |
| lux-a.pk042.g1 | + | Operon (2898614 . . . 2901396)/note = "predicted operon"/note = "ordered genes contained in the operon: + ygcE" |
| lux-a.pk049.a8 | + | Operon (2556791 . . . 2558086)/note = "predicted operon"/note = "ordered genes contained in the operon: b2442" |
| lux-a.pk053.g7 | − | Operon complement(2180055 . . . 2180801)/note = "predicted operon"/note = "ordered genes contained in the operon: b2101" |
| lux-a.pk061.a5 | − | Operon complement(3838176 . . . 3841494)/note = "predicted operon"/note = "ordered genes contained in the operon: yicM yicN yicO" |
| lux-a.pk068.b3 | − | Operon complement(114407 . . . 117549)/note = "predicted operon"/note = "ordered genes contained in the operon: b0105 hofC hofB ppdD" |
| lux-a.pk074.c11 | + | Operon (3555900 . . . 3557498)/note = "predicted operon"/note = "ordered genes contained in the operon: yhgB" |

TABLE 18-continued

Luxarray 1.0 Clone Collection

| Lux ID | Coding strand | Operon |
|---|---|---|
| lux-a.pk080.d1 | + | Operon (209679 . . . 212266)/note = "predicted operon"/note = "ordered genes contained in the operon: 1dcC b0187" |
| lux-a.pk088.c3 | − | Operon complement(264844 . . . 266191)/note = "predicted operon"/note = "ordered genes contained in the operon: b0250 b0251" |
| lux-a.pk0002.b7 | − | Operon complement(273325 . . . 274341)/note = "predicted operon"/note = "ordered genes contained in the operon: yi52_1" |
| lux-a.pk009.c11 | − | Operon complement(3080896 . . . 3081816)/note = "predicted operon"/note = "ordered genes contained in the operon: speB" |
| lux-a.pk0019.a8 | + | Operon (1896421 . . . 1898049)/note = "predicted operon"/note = "ordered genes contained in the operon: b1815" |
| lux-a.pk0024.a3 | + | Operon (1244383 . . . 1244823)/note = "predicted operon"/note = "ordered genes contained in the operon: b1196" |
| lux-a.pk029.c10 | − | Operon complement(1550422 . . . 1550784)/note = "predicted operon"/note = "ordered genes contained in the operon: b1477" |
| lux-a.pk033.g10 | − | Operon complement(1566978 . . . 1568513)/note = "predicted operon"/note = "ordered genes contained in the operon: xasA" |
| lux-a.pk038.c2 | + | Operon (1599514 . . . 1605313)/note = "predicted operon"/note = "ordered genes contained in the operon: b1513 b1514 b1515 b1516 b1517 b1518" |
| lux-a.pk043.c1 | − | Operon complement(2929887 . . . 2931710)/note = "documented fucAO operon" |
| lux-a.pk049.d8 | − | Operon complement(5683 . . . 6459)/note = "predicted operon"/note = "ordered genes contained in the operon: yaaA" |
| lux-a.pk054.a6 | − | Operon complement(4350778 . . . 4352295)/note = "documented lysU operon" |
| lux-a.pk061.b6 | − | Operon complement(1815172 . . . 1819643)/note = "documented celABCDF operon" |
| lux-a.pk068.b8 | + | Operon (1473162 . . . 1475474)/note = "predicted operon"/note = "ordered genes contained in the operon: ydbD" |
| lux-a.pk074.d9 | + | Operon (1903658 . . . 1904278)/note = "predicted operon"/note = "ordered genes contained in the operon: b1821" |
| lux-a.pk080.e12 | + | Operon (243543 . . . 244121)/note = "predicted operon"/note = "ordered genes contained in the operon: gmhA" |
| lux-a.pk088.d5 | − | Operon complement(3105038 . . . 3107233)/note = "documented speC operon" |
| lux-lacZ | | complement(360473 . . . 365529) |
| lux-a.pk009.d6 | − | Operon complement(642780 . . . 643190)/note = "predicted operon"/note = "ordered genes contained in the operon: rnk" |
| lux-a.pk0019.a9 | + | Operon (3484440 . . . 3486530)/note = "predicted operon"/note = "ordered genes contained in the operon: yhfK" |
| lux-a.pk0024.b6 | + | Operon (122092 . . . 129336)/note = "documented pdhR-aceEF-lpdA operon" |
| lux-a.pk029.c11 | + | Operon (4506526 . . . 4507122)/note = "predicted operon"/note = "ordered genes contained in the operon: b4285" |
| lux-a.pk033.g11 | + | Operon (1289465 . . . 1290478)/note = "predicted operon"/note = "ordered genes contained in the operon: hnr" |
| lux-a.pk038.c7 | + | Operon (2609941 . . . 2612802)/note = "predicted operon"/note = "ordered genes contained in the operon: b2491 b2492" |
| lux-a.pk043.e11 | − | Operon complement(2885601 . . . 2889921)/note = "documented cysJIH operon" |
| lux-a.pk049.g7 | − | Operon complement(1886085 . . . 1887770)/note = "predicted operon"/note = "ordered genes contained in the operon: fadD" |
| lux-a.pk054.c10 | − | Operon complement(3317629 . . . 3319272)/note = "predicted operon"/note = "ordered genes contained in the operon: yhbX" |
| lux-a.pk061.b7 | + | Operon (180884 . . . 182308 /note = "predicted operon"/note = "ordered genes contained in the operon: htrA" |
| lux-a.pk068.b9 | + | Operon (467520 . . . 471641 /note = "predicted operon"/note = "ordered genes contained in the operon: b0447 mdlA mdlB" |
| lux-a.pk074.e3 | − | Operon complement(4594719 . . . 4596971)/note = "predicted operon"/note = "ordered genes contained in the operon: mdoB" |
| lux-a.pk080.g3 | + | Operon (655780 . . . 656340)/note = "predicted operon"/note = "ordered genes contained in the operon: ybeG" |
| lux-a.pk088.e1 | − | Operon complement(1932863 . . . 1934338)/note = "documented zwf operon" |
| lux-a.pk0002.e4 | + | Operon (1735868 . . . 1736893)/note = "documented purR operon" |

TABLE 18-continued

Luxarray 1.0 Clone Collection

| Lux ID | Coding strand | Operon |
|---|---|---|
| lux-a.pk009.d11 | − | Operon complement(4363050 . . . 4364351)/note = "predicted operon"/note = "ordered genes contained in the operon: dcuA" |
| lux-a.pk0019.c11 | + | Operon (2621064 . . . 2623130)/note = "documented ppk operon" |
| lux-a.pk0024.c7 | − | Operon complement(592551 . . . 594666)/note = "predicted operon"/note = "ordered genes contained in the operon: b0570 b0571" |
| lux-a.pk029.c5 | − | Operon complement(266408 . . . 267244)/note = "predicted operon"/note = "ordered genes contained in the operon: b0252" |
| lux-a.pk033.g2 | − | Operon complement(2131512 . . . 2135265)/note = "predicted operon"/note = "ordered genes contained in the operon: b2060 b2061 b2062" |
| lux-a.pk038.d9 | − | Operon complement(65855 . . . 70048)/note = "documented araBAD operon" |
| lux-a.pk043.f11 | + | Operon (4200898 . . . 4202223)/note = "predicted operon"/note = "ordered genes contained in the operon: hydG" |
| lux-a.pk049.h9 | + | Operon (3352267 . . . 3359575)/note = "documented gltBDF operon" |
| lux-a.pk054.c3 | − | Operon complement(2729620 . . . 2732193)/note = "predicted operon"/note = "ordered genes contained in the operon: clpB" |
| lux-a.pk061.c3 | + | Operon (202560 . . . 208608)/note = "predicted operon"/note = "ordered genes contained in the operon: lpxA lpxB rnhB dnaE" |
| lux-a.pk068.h2 | + | Operon (103155 . . . 106456)/note = "documented ftsQAZ operon" |
| lux-a.pk074.f1 | + | Operon (2550372 . . . 2552144)/note = "predicted operon"/note = "ordered genes contained in the operon: amiA hemF" |
| lux-a.pk081.b5 | + | Operon (3728760 . . . 3733786)/note = "documented xylFGHR operon" |
| lux-a.pk088.g2 | + | Operon (882896 . . . 884128)/note = "predicted operon"/note = "ordered genes contained in the operon: b0842" |
| lux-lacZ | | complement(360473 . . . 365529) |
| lux-a.pk009.f3 | − | f176; This 176 aa ORF is 45 pct identical (2 gaps) to 172 residues of an approx. 184 aa protein FIMF_ECOLI SW: P08189 |
| lux-a.pk0019.d12 | − | Operon complement(4061182 . . . 4066856)/note = "predicted operon"/note = "ordered genes contained in the operon: yihO yihO yihP yihQ" |
| lux-a.pk0024.e1 | − | Operon complement(2854476 . . . 2854829)/note = "predicted operon"/note = "ordered genes contained in the operon: ygbA" |
| lux-a.pk029.c5 | + | Operon (2766686 . . . 2767507)/note = "predicted operon"/note = "ordered genes contained in the operon: b2633" |
| lux-a.pk033.g7 | + | Operon (2001895 . . . 2004101)/note = "documented fliDST operon" |
| lux-a.pk038.e11 | + | Operon (3785854 . . . 3786687)/note = "predicted operon"/note = "ordered genes contained in the operon: yibQ" |
| lux-a.pk043.f6 | − | Operon complement(3040509 . . . 3041168)/note = "predicted operon"/note = "ordered genes contained in the operon: b2899" |
| lux-a.pk050.a11 | − | Operon complement(4437449 . . . 4438792)/note = "predicted operon"/note = "ordered genes contained in the operon: ytfL" |
| lux-a.pk054.e11 | − | Operon complement(3711690 . . . 3713909)/note = "predicted operon"/note = "ordered genes contained in the operon: bisC" |
| lux-a.pk061.d8 | − | Operon complement(3148833 . . . 3149999)/note = "documented exbDB operon" |
| lux-a.pk068.h4 | + | Operon (3180566 . . . 3181339)/note = "predicted operon"/note = "ordered genes contained in the operon: ygiE" |
| lux-a.pk074.g9 | − | Operon complement(4000900 . . . 4002326)/note = "predicted operon"/note = "ordered genes contained in the operon: rarD yigI" |
| lux-a.pk081.b6 | + | Operon (879950 . . . 881152)/note = "predicted operon"/note = "ordered genes contained in the operon: dacC" |
| lux-a.pk088.h3 | + | Operon (122092 . . . 129336)/note = "documented pdhR-aceEF-lpdA operon" |
| lux-a.pk0002.g5 | + | Operon (2342885 . . . 2346534)/note = "documented nrdAB operon" |
| lux-a.pk009.g3 | − | Operon complement(2181736 . . . 2183321)/note = "predicted operon"/note = "ordered genes contained in the operon: b2103 b2104" |
| lux-a.pk0019.e3 | − | Operon complement(4012721 . . . 4013719)/note = "predicted operon"/note = "ordered genes contained in the operon:" |

TABLE 18-continued

Luxarray 1.0 Clone Collection

| Lux ID | Coding strand | Operon |
|---|---|---|
| lux-a.pk0024.e6 | + | Operon (893007 . . . 897152)/note = "documented potFGHI operon" |
| lux-a.pk029.c9 | + | Operon (89634 . . . 103153)/note = "predicted operon"/note = "ordered genes contained in the operon: yabB yabC ftsL ftsI murE murF mraY murD ftsW murG murC ddlB" |
| lux-a.pk034.a11 | − | Operon complement(2116702 . . . 2119576)/note = "predicted operon"/note = "ordered genes contained in the operon: b2046 b2047" |
| lux-a.pk038.f1 | + | Operon (1830452 . . . 1831258)/note = "predicted operon"/note = "ordered genes contained in the operon: xthA" |
| lux-a.pk043.g5 | − | Operon complement(1957304 . . . 1957876)/note = "predicted operon"/note = "ordered genes contained in the operon: b1875" |
| lux-a.pk050.a12 | − | Operon complement(4338298 . . . 4339206)/note = "documented melR operon" |
| lux-a.pk054.e5 | − | Operon complement(3858976 . . . 3861491)/note ="predicted operon"/note ="ordered genes contained in the operon: glvG glvB glvC" |
| lux-a.pk061.e9 | − | Operon complement(2980519 . . . 2982146)/note = "predicted operon"/note = "ordered genes contained in the operon: kduD kduI" |
| lux-a.pk069.a4 | − | Operon complement(3026544 . . . 3028966)/note = "predicted operon"/note = "ordered genes contained in the operon: b2886 b2887" |
| lux-a.pk074.h10 | + | Operon (4109895 . . . 4110335)/note = "predicted operon"/note = "ordered genes contained in the operon: yiiR" |
| lux-a.pk081.c2 | − | Operon complement(4457474 . . . 4457938)/note = "predicted operon"/note = "ordered genes contained in the operon: nrdG" |
| lux-a.pk089.a11 | + | Operon (1094746 . . . 1096052)/note = "predicted operon"/note = "ordered genes contained in the operon: b1028 b1029" |
| lux-a.pk0003.a2 | + | Operon (349236 . . . 353816)/note = "predicted operon"/note = "ordered genes contained in the operon: b0333 b0334 b0335" |
| lux-a.pk009.g7 | − | FecR protein |
| lux-a.pk0019.e4 | + | Operon (1303788 . . . 1304792)/note = "predicted operon"/note = "ordered genes contained in the operon: oppF" |
| lux-a.pk0024.f5 | + | Operon (832293 . . . 835433)/note = "predicted operon"/note = "ordered genes contained in the operon: dinG ybiB" |
| lux-a.pk029.e7 | − | Operon complement(1852120 . . . 1852878)/note = "predicted operon"/note = "ordered genes contained in the operon: b1770" |
| lux-a.pk034.b8 | + | Operon (4126252 . . . 4129847)/note = "documented metBL operon" |
| lux-a.pk038.f3 | − | Operon complement(303719 . . . 309250)/note = "predicted operon"/note = "ordered genes contained in the operon: b0289 b0290 b0291 b0292" |
| lux-a.pk043.h1 | + | Operon (2383874 . . . 2384851)/note = "predicted operon"/note = "ordered genes contained in the operon: b2271" |
| lux-a.pk050.b9 | − | Operon complement(360473 . . . 365529)/note = "documented lacAYZ operon" |
| lux-a.pk054.f7 | + | Operon (1057307 . . . 1061621)/note = "documented torCAD operon" |
| lux-a.pk061.f10 | − | Operon complement(2612840 . . . 2613901)/note = "predicted operon"/note = "ordered genes contained in the operon: b2493" |
| lux-a.pk069.a6 | − | Operon complement(4372207 . . . 4373235)/note = "predicted operon"/note = "ordered genes contained in the operon: yjeK" |
| lux-a.pk075.a10 | + | Operon (4609980 . . . 4611053)/note = "predicted operon"/note = "ordered genes contained in the operon: yjjU" |
| lux-a.pk081.e3 | − | Operon complement(2024345 . . . 2026054)/note = "predicted operon"/note = "ordered genes contained in the operon: b1956" |
| lux-a.pk089.c4 | + | Operon (434858 . . . 436331)/note = "predicted operon"/note = "ordered genes contained in the operon: b0417 b0418" |
| lux-a.pk0003.c1 | + | Operon (1216509 . . . 1218074)/note = "predicted operon"/note = "ordered genes contained in the operon: b1168" |
| lux-a.pk0010.a12 | + | Operon (738224 . . . 740148)/note = "predicted operon"/note = "ordered genes contained in the operon: ybgA phrB" |
| lux-a.pk0019.f8 | + | Operon (970975 . . . 971868)/note = "predicted operon"/note = "ordered genes contained in the operon: b0919" |
| lux-a.pk0024.f7 | − | Operon complement(4555923 . . . 4558261)/note = "predicted operon"/note = "ordered genes contained in the operon: |

TABLE 18-continued

Luxarray 1.0 Clone Collection

| Lux ID | Coding strand | Operon |
|---|---|---|
| | | iadA yjiG yjiH" |
| lux-a.pk029.g2 | − | Operon complement(50380 . . . 51222)/note = "predicted operon"/note = "ordered genes contained in the operon: apaH" |
| lux-a.pk034.b9 | − | Operon complement(3843403 . . . 3844794)/note = "documented uhpT operon" |
| lux-a.pk038.g11 | + | Operon (2212886 . . . 2213617)/note = "predicted operon"/note = "ordered genes contained in the operon: yehV" |
| lux-a.pk044.b6 | − | Operon complement(3451145 . . . 3453035)/note = "predicted operon"/note = "ordered genes contained in the operon: pinO yheD" |
| lux-a.pk050.d9 | − | Operon complement(2759372 . . . 2763174)/note = "predicted operon"/note = "ordered genes contained in the operon: b2627 b2628" |
| lux-a.pk054.h8 | + | Operon (195785 . . . 200360)/note = "predicted operon"/note = "ordered genes contained in the operon: cdsA yaeL b0177" |
| lux-a.pk061.f4 | + | Operon (4382971 . . . 4383596)/note = "predicted operon"/note = "ordered genes contained in the operon: yjeN yjeO" |
| lux-a.pk069.a8 | − | Operon complement(3673920 . . . 3675995)/note = "predicted operon"/note = "ordered genes contained in the operon: yhjF" |
| lux-a.pk075.c5 | + | Operon (2192320 . . . 2194353)/note = "predicted operon"/note = "ordered genes contained in the operon: metG" |
| lux-a.pk081.f12 | + | Operon (3031085 . . . 3031633)/note = "predicted operon"/note = "ordered genes contained in the operon: b2889" |
| lux-a.pk089.c6 | − | Operon complement(4091029 . . . 4095029)/note = "documented rhaBAD operon" |
| lux-a.pk0003.d1 | − | Operon complement(1246919 . . . 1250091)/note = "predicted operon"/note = "ordered genes contained in the operon: ycgC b1199 b1200" |
| lux-a.pk0010.b4 | + | Operon (1923464 . . . 1924806)/note = "predicted operon"/note = "ordered genes contained in the operon: b1843 b1844" |
| lux-a.pk0019.g1 | + | Operon 2010524 . . . 2010802 /note = "predicted operon"/note = "ordered genes contained in the operon: b1936" |
| lux-a.pk0024.g2 | − | Operon complement(394354 . . . 395511)/note = "predicted operon"/note = "ordered genes contained in the operon: yaiH" |
| lux-a.pk029.g4 | − | Operon complement(4112149 . . . 4113159)/note = "predicted operon"/note = "ordered genes contained in the operon: glpX" |
| lux-a.pk034.d1 | − | Operon complement(4519695 . . . 4523371)/note = "predicted operon"/note = "ordered genes contained in the operon: yjhG yjhH yjhI" |
| lux-a.pk038.h1 | − | Operon complement(1654771 . . . 1655517)/note = "predicted operon"/note = "ordered genes contained in the operon: b1585" |
| lux-a.pk044.b7 | − | Operon complement(4097072 . . . 4098106)/note = "documented rhaT operon" |
| lux-a.pk050.e1 | − | Operon complement(2906051 . . . 2907688)/note = "predicted operon"/note = "ordered genes contained in the operon: pyrG" |
| lux-a.pk055.a12 | − | Operon complement(3275497 . . . 3276306)/note = "predicted operon"/note = "ordered genes contained in the operon: agaR" |
| lux-a.pk061.f5 | − | Operon complement(3924173 . . . 3924631)/note = "documented asnC operon" |
| lux-a.pk069.d3 | − | Operon complement(4125658 . . . 4125975)/note = "documented metJ operon" |
| lux-a.pk075.d9 | + | Operon 3220238 . . . 3223812/note = "documented ebgAC operon" |
| lux-a.pk081.f3 | − | Operon complement(2570177 . . . 2573897)/note = "predicted operon"/note = "ordered genes contained in the operon: cchA eutI b2459 b2460 b2461 b2462" |
| lux-a.pk089.e2 | − | Operon complement(2624715 . . . 2626958)/note = "predicted operon"/note = "ordered genes contained in the operon: b2503" |
| lux-a.pk0003.e12 | + | Operon (4022578 . . . 4024818)/note = "predicted operon"/note = "ordered genes contained in the operon: yigC ubiB"/ |
| lux-a.pk0010.c7 | − | Operon complement(3750593 . . . 3752058)/note = "predicted operon"/note = "ordered genes contained in the operon: yiaV yiaW" |
| lux-a.pk0019.g2 | − | Operon complement(2654556 . . . 2657487)/note = "predicted operon"/note = "ordered genes contained in the operon: yfhJ fdx hscA yfhE" |
| lux-a.pk0024.g3 | + | Operon (2032043 . . . 2032777)/note = "predicted operon"/ |

TABLE 18-continued

Luxarray 1.0 Clone Collection

| Lux ID | Coding strand | Operon |
|---|---|---|
| | | note = "ordered genes contained in the operon: b1964 b1965" |
| lux-a.pk030.b3 | − | Operon complement(4272339 . . . 4272689)/note = "predicted operon"/note = "ordered genes contained in the operon: yjcB" |
| lux-a.pk034.d3 | − | Operon complement(2858490 . . . 2859287)/note = "predicted operon"/note = "ordered genes contained in the operon: b2735" |
| lux-a.pk038.h6 | − | Operon complement(2441911 . . . 2446793)/note = "predicted operon"/note = "ordered genes contained in the operon: b2325 b2326 yfcA mepA aroC yfcB" |
| lux-a.pk044.d10 | − | Operon complement(3668922 . . . 3669524)/note = "predicted operon"/note = "ordered genes contained in the operon: yhjB" |
| lux-a.pk050.e10 | + | Operon (4439959 . . . 4445812)/note = "predicted operon"/note = "ordered genes contained in the operon: ytfM ytfN ytfP" |
| lux-a.pk055.a3 | + | Operon (250898 . . . 251953)/note = "predicted operon"/note = "ordered genes contained in the operon:" |
| lux-a.pk061.h3 | − | Operon complement(489334 . . . 490036)/note = "predicted operon"/note = "ordered genes contained in the operon: ybaM priC" |
| lux-a.pk069.d8 | + | Operon (424235 . . . 429700)/note = "documented queA-tgt-yajC-secD-secF operon" |
| lux-a.pk075.f11 | − | Operon complement(2478658 . . . 2481359)/note = "predicted operon"/note = "ordered genes contained in the operon: emrY emrK" |
| lux-a.pk081.g10 | + | Operon (1773611 . . . 1776371)/note = "predicted operon"/note = "ordered genes contained in the operon: ydiF b1695" |
| lux-a.pk089.e4 | − | Operon complement(2563501 . . . 2570070)/note = "predicted operon"/note = "ordered genes contained in the operon: b2451 eutH eutG eutJ eutE cchB" |
| lux-a.pk0003.f1 | − | Operon complement(1252308 . . . 1255175)/note = "predicted operon"/note = "ordered genes contained in the operon: b1202" |
| lux-a.pk0010.d6 | − | Operon complement(2181736 . . . 2183321)/note = "predicted operon"/note = "ordered genes contained in the operon: b2103 b2104" |
| lux-a.pk0020.b12 | − | Operon complement(805221 . . . 806504)/note = "predicted operon"/note = "ordered genes contained in the operon: ybhC" |
| lux-a.pk0024.g8 | − | Operon complement(3463886 . . . 3464362)/note = "predicted operon"/note = "ordered genes contained in the operon: bfr" |
| lux-a.pk030.b8 | + | Operon (208621 . . . 209580)/note = "documented accA operon" |
| lux-a.pk034.d6 | + | Operon (4501566 . . . 4503973)/note = "predicted operon"/note = "ordered genes contained in the operon: yjhB yjhC" |
| lux-a.pk039.a5 | − | Operon complement(437539 . . . 439401)/note = "predicted operon"/note = "ordered genes contained in the operon: b0420" |
| lux-a.pk044.f8 | − | Operon complement(4620670 . . . 4622358)/note = "predicted operon"/note = "ordered genes contained in the operon: lplA smp" |
| lux-a.pk050.e4 | + | Operon (1958086 . . . 1959819)/note = "predicted operon"/note = "ordered genes contained in the operon: argS" |
| lux-a.pk055.a4 | − | Operon complement(899067 . . . 902957)/note = "documented artPIQMJ operon" |
| lux-a.pk062.a12 | − | Operon complement(1431108 . . . 1431698)/note = "predicted operon"/note = "ordered genes contained in the operon: b1374" |
| lux-a.pk069.f11 | − | Operon complement(3393963 . . . 3396015)/note = "predicted operon"/note = "ordered genes contained in the operon: cafA yhdE" |
| lux-a.pk075.f4 | + | Operon (47246 . . . 49631)/note = "predicted operon"/note = "ordered genes contained in the operon: yabF kefC" |
| lux-a.pk081.h2 | + | Operon (2852361 . . . 2854439)/note = "predicted operon"/note = "ordered genes contained in the operon: fhlA" |
| lux-a.pk089.e7 | + | Operon (3208422 . . . 3212529)/note = "documented rpsU-dnaG-rpoD operon" |
| lux-a.pk0004.a2 | − | Operon complement(2493070 . . . 2493312)/note = "predicted operon"/note = "ordered genes contained in the operon: b2377" |
| lux-a.pk0010.f10 | − | Operon complement(411831 . . . 416176)/note = "predicted operon"/note = "ordered genes contained in the operon: sbcC sbcD" |
| lux-a.pk0020.b4 | + | Operon (4105132 . . . 4106094)/note = "predicted operon"/ |

TABLE 18-continued

Luxarray 1.0 Clone Collection

| Lux ID | Coding strand | Operon |
|---|---|---|
| | | note = "ordered genes contained in the operon: pfkA" |
| lux-a.pk0024.h2 | + | Operon (2808791 . . . 2809321)/note = "predicted operon"/note = "ordered genes contained in the operon: emrR" |
| lux-a.pk030.d3 | + | Operon (2042885 . . . 2050036)/note = "predicted operon"/note = "ordered genes contained in the operon: b1978" |
| lux-a.pk034.e1 | + | Operon (253467 . . . 254202)/note = "predicted operon"/note = "ordered genes contained in the operon: b0235 prfH" |
| lux-a.pk039.a6 | − | Operon complement(4553059 . . . 4553889)/note = "predicted operon"/note = "ordered genes contained in the operon: yjiC" |
| lux-a.pk044.f9 | + | Operon (4339489 . . . 4342368)/note = "documented melAB operon" |
| lux-a.pk050.e9 | − | Operon complement(910405 . . . 913043)/note = "predicted operon"/note = "ordered genes contained in the operon: b0872 b0873" |
| lux-a.pk055.b2 | − | Operon complement(930308 . . . 931273)/note = "predicted operon"/note = "ordered genes contained in the operon: trxB" |
| lux-a.pk062.b4 | − | Operon complement(2513663 . . . 2515969)/note = "predicted operon"/note = "ordered genes contained in the operon: yfeA" |
| lux-a.pk069.f4 | + | Operon (3866983 . . . 3868068)/note = "predicted operon"/note = "ordered genes contained in the operon: yidS" |
| lux-a.pk075.f5 | − | Operon complement(2447248 . . . 2453021)/note = "predicted operon"/note = "ordered genes contained in the operon: b2332 b2333 b2334 b2335 b2336 b2337 b2338" |
| lux-a.pk081.h3 | − | Operon complement(4577638 . . . 4580618)/note = "documented hsdMS operon" |
| lux-a.pk089.f1 | − | Operon complement(3144871 . . . 3145706)/note = "predicted operon"/note = "ordered genes contained in the operon: b2999 b3000" |
| lux-lacZ | | complement(360473 . . . 365529) |
| lux-a.pk0010.g10 | − | Operon complement(3261327 . . . 3264706)/note = "documented tdcABC operon" |
| lux-a.pk0020.c2 | + | Operon (320832 . . . 323677)/note = "predicted operon"/note = "ordered genes contained in the operon: b0306 b0307 b0308" |
| lux-a.pk0024.h3 | + | Operon (2990116 . . . 2991492)/note = "predicted operon"/note = "ordered genes contained in the operon: b2852" |
| lux-a.pk030.f10 | − | Operon complement(4067055 . . . 4067981)/note = "predicted operon"/note = "ordered genes contained in the operon: yihR" |
| lux-a.pk034.f5 | − | Operon complement(1417789 . . . 1418265)/note = "predicted operon"/note = "ordered genes contained in the operon: b1356" |
| lux-a.pk039.b6 | + | Operon (547838 . . . 550555)/note = "predicted operon"/note = "ordered genes contained in the operon: b0519 b0520 ybcF" |
| lux-a.pk044.g3 | + | Operon (1421806 . . . 1424004)/note = "predicted operon"/note = "ordered genes contained in the operon: trkG b1364 b1365 b1366" |
| lux-a.pk050.f6 | − | Operon complement(2643033 . . . 2650307)/note = "predicted operon"/note = "ordered genes contained in the operon: b2519 b2520" |
| lux-a.pk055.b3 | + | Operon (179237 . . . 180754)/note = "predicted operon"/note = "ordered genes contained in the operon: dgt" |
| lux-a.pk062.c6 | − | Operon complement(602639 . . . 603886)/note = "predicted operon"/note = "ordered genes contained in the operon: ybdG" |
| lux-a.pk069.f6 | + | Operon (4324713 . . . 4327816)/note = "predicted operon"/note = "ordered genes contained in the operon: yjdA yjcZ" |
| lux-a.pk075.g1 | − | Operon complement(2519613 . . . 2522898)/note = "predicted operon"/note = "ordered genes contained in the operon: xapR xapB xapA" |
| lux-a.pk081.h7 | − | Operon complement(2224529 . . . 2225290)/note = "predicted operon"/note = "ordered genes contained in the operon: yohF" |
| lux-a.pk089.g1 | + | Operon (3776681 . . . 3778644)/note = "predicted operon"/note = "ordered genes contained in the operon: lctR lctD" |
| lux-a.pk0004.c1 | + | Operon (1848884 . . . 1849900)/note = "documented ansA operon" |
| lux-a.pk0010.g12 | + | Operon (3225442 . . . 3228880)/note = "predicted operon"/note = "ordered genes contained in the operon: ygjJ ygjK" |
| lux-a.pk0020.c3 | − | Operon complement(2638706 . . . 2640864)/note = "predicted operon"/note = "ordered genes contained in the operon: gcpE yfgA" |
| lux- | − | Operon complement(3132887 . . . 3134386)/note = "predicted |

TABLE 18-continued

Luxarray 1.0 Clone Collection

| Lux ID | Coding strand | Operon |
|---|---|---|
| a.pk0025.c11 | | operon"/note = "ordered genes contained in the operon: pitB" |
| lux-a.pk030.f2 | − | Operon complement(1061773 . . . 1062998)/note = "predicted operon"/note = "ordered genes contained in the operon: yccD cbpA" |
| lux-a.pk034.g4 | + | Operon (106557 . . . 107474)/note = "predicted operon"/note = "ordered genes contained in the operon: lpxC" |
| lux-a.pk039.d1 | + | Operon (339389 . . . 341731)/note = "predicted operon"/note = "ordered genes contained in the operon: b0323 b0324" |
| lux-a.pk044.h4 | + | Operon (3535122 . . . 3537344)/note = "predicted operon"/note = "ordered genes contained in the operon: yhgF" |
| lux-a.pk050.g1 | + | Operon (3150251 . . . 3151438)/note = "documented metC operon" |
| lux-a.pk055.d10 | − | Operon complement(3363337 . . . 3364353)/note = "predicted operon"/note = "ordered genes contained in the operon: yi52_1" |
| lux-a.pk062.e11 | + | Operon (4055987 . . . 4057762)/note = "predicted operon"/note = "ordered genes contained in the operon: yihK" |
| lux-a.pk069.g7 | + | Operon (190 . . . 5020)/note = "documented thrLABC operon" |
| lux-a.pk075.h9 | − | Operon complement(858436 . . . 859251)/note = "predicted operon"/note = "ordered genes contained in the operon: b0822" |
| lux-a.pk081.h8 | − | Operon complement(1145234 . . . 1145857)/note = "predicted operon"/note = "ordered genes contained in the operon: yceF" |
| lux-a.pk090.a2 | + | Operon (1312044 . . . 1312682)/note = "predicted operon"/note = "ordered genes contained in the operon: yciD" |
| lux-lacZ | | complement(360473 . . . 365529) |
| lux-a.pk0011.a2 | + | Operon (539783 . . . 542257)/note = "predicted operon"/note = "ordered genes contained in the operon: b0513 b0514" |
| lux-a.pk0020.d10 | − | Operon complement(296605 . . . 301797)/note = "predicted operon"/note = "ordered genes contained in the operon: b0282 b0283 b0284 b0285 b0286" |
| lux-a.pk0025.c9 | − | Operon complement(2238648 . . . 2239688)/note = "documented galS operon" |
| lux-a.pk030.f8 | − | Operon complement(4535227 . . . 4537078)/note = "predicted operon"/note = "ordered genes contained in the operon: yjhT yjhA" |
| lux-a.pk034.h2 | − | Operon complement(720279 . . . 723637)/note = "documented kdpDE operon" |
| lux-a.pk039.d10 | − | Operon complement(1411555 . . . 1415410)/note = "predicted operon"/note = "ordered genes contained in the operon: ydaC lar recT recE" |
| lux-a.pk045.c12 | − | Operon complement(3068185 . . . 3071711)/note = "predicted operon"/note = "ordered genes contained in the operon: fba pgk epd" |
| lux-a.pk050.g10 | − | Operon complement(2227458 . . . 2228405)/note = "predicted operon"/note = "ordered genes contained in the operon: yohI" |
| lux-a.pk055.e12 | − | Operon complement(1447100 . . . 1449373)/note = "predicted operon"/note = "ordered genes contained in the operon: tynA" |
| lux-a.pk062.e7 | − | Operon complement(3171520 . . . 3175926)/note = "predicted operon"/note = "ordered genes contained in the operon: parE yqiA icc yqiB b3034" |
| lux-a.pk070.a4 | − | Operon complement(3904481 . . . 3909153)/note = "documented pstSCAB-phoU operon" |
| lux-a.pk076.c10 | + | Operon (22391 . . . 27227)/note = "documented ileS-lspA-lytB operon" |
| lux-a.pk082.a8 | + | Operon (972760 . . . 980009)/note = "predicted operon"/note = "ordered genes contained in the operon: smtA mukF mukE mukB" |
| lux-a.pk090.g5 | − | Operon complement(3043178 . . . 3043921)/note = "predicted operon"/note = "ordered genes contained in the operon: ygfF" |
| lux-a.pk0004.e11 | − | Operon complement(1492172 . . . 1493236)/note = "predicted operon"/note = "ordered genes contained in the operon: b1422" |
| lux-a.pk0011.a6 | + | Operon (4619338 . . . 4620669)/note = "predicted operon"/note = "ordered genes contained in the operon: yjjJ" |
| lux-a.pk0020.d11 | + | Operon (5234 . . . 5530)/note = "predicted operon"/note = "ordered genes contained in the operon: b0005" |
| lux-a.pk0025.d10 | − | Operon complement(2409459 . . . 2410632)/note = "predicted operon"/note = "ordered genes contained in the operon: b2293 b2294" |
| lux-a.pk030.g7 | − | Operon complement(10643 . . . 11356)/note = "predicted operon"/note = "ordered genes contained in the operon: |

TABLE 18-continued

Luxarray 1.0 Clone Collection

| Lux ID | Coding strand | Operon |
|---|---|---|
| | | b0011" |
| lux-a.pk034.h6 | + | Operon (2160898 . . . 2163020)/note = "documented baeSR operon" |
| lux-a.pk039.e8 | + | Operon (4008666 . . . 4009565)/note = "predicted operon"/note = "ordered genes contained in the operon: yigM" |
| lux-a.pk045.c2 | − | Operon complement(2699761 . . . 2702083)/note = "documented rnc-era-recO operon" |
| lux-a.pk050.g2 | − | Operon complement(550750 . . . 552323)/note = "documented purEK operon" |
| lux-a.pk055.g12 | − | Operon complement(1877427 . . . 1877972)/note = "predicted operon"/note = "ordered genes contained in the operon: b1796 b1797" |
| lux-a.pk062.f10 | − | Operon complement(4294798 . . . 4296945)/note = "documented fdhF operon" |
| lux-a.pk070.b7 | − | Operon complement(2223064 . . . 2223675)/note = "predicted operon"/note = "ordered genes contained in the operon: yohC" |
| lux-a.pk076.c5 | − | Operon complement(3795866 . . . 3805725)/note = "documented rfaQGPSBIJYZK operon" |
| lux-a.pk082.b4 | − | Operon complement(3396024 . . . 3398784)/note = "documented mreBCD operon" |
| lux-a.pk089.g1 | + | Operon (3776681 . . . 3778644)/note = "predicted operon"/note = "ordered genes contained in the operon: lctR lctD" |
| lux-lacZ | | complement(360473 . . . 365529) |
| lux-a.pk0011.d6 | − | Operon complement(542485 . . . 545587)/note = "predicted operon"/note = "ordered genes contained in the operon: b0515 b0516 b0517" |
| lux-a.pk0020.g10 | − | Operon complement(3981965 . . . 3983620)/note = "predicted operon"/note = "ordered genes contained in the operon: aslA" |
| lux-a.pk0025.e12 | − | Operon complement(1274402 . . . 1276841)/note = "documented narXL operon" |
| lux-a.pk030.h2 | + | Operon (3234934 . . . 3235938)/note = "predicted operon"/note = "ordered genes contained in the operon: ygjR" |
| lux-a.pk035.a10 | − | Operon complement(747144 . . . 751401)/note = "predicted operon"/note = "ordered genes contained in the operon: b0716 b0717 b0718" |
| lux-a.pk039.f11 | + | Operon (269466 . . . 270978)/note = "predicted operon"/note = "ordered genes contained in the operon: b0255 tra8_1" |
| lux-a.pk045.d11 | − | Operon complement(3508698 . . . 3509763)/note = "predicted operon"/note = "ordered genes contained in the operon: yhfY yhfZ" |
| lux-a.pk050.g3 | − | Operon complement(276980 . . . 279099)/note = "predicted operon"/note = "ordered genes contained in the operon: yagC b0263 insB_1 insA_2" |
| lux-a.pk055.g3 | − | Operon complement(149715 . . . 152854)/note = "predicted operon"/note = "ordered genes contained in the operon: yadC yadK yadL yadM" |
| lux-a.pk062.h4 | + | Operon (632809 . . . 633969)/note = "predicted operon"/note = "ordered genes contained in the operon: b0600" |
| lux-a.pk070.c1 | + | Operon (440773 . . . 442221)/note = "predicted operon"/note = "ordered genes contained in the operon: b0423" |
| lux-a.pk076.c8 | + | Operon (319451 . . . 320305)/note = "predicted operon"/note = "ordered genes contained in the operon: b0305" |
| lux-a.pk082.b5 | − | Operon complement(3868065 . . . 3869402)/note = "predicted operon"/note = "ordered genes contained in the operon: yidT" |
| lux-a.pk090.a2 | + | Operon (1312044 . . . 1312682)/note = "predicted operon"/note = "ordered genes contained in the operon: yciD" |
| lux-a.pk0004.f7 | − | Operon complement(2034816 . . . 2036893)/note = "predicted operon"/note = "ordered genes contained in the operon: b1968 b1969" |
| lux-a.pk0011.d7 | + | Operon (70387 . . . 71265)/note = "documented araC operon" |
| lux-a.pk0020.g3 | + | Operon (770678 . . . 773404)/note = "documented cydAB operon" |
| lux-a.pk0025.e2 | + | Operon (4569935 . . . 4571500)/note = "predicted operon"/note = "ordered genes contained in the operon: yjiT" |
| lux-a.pk031.a12 | + | Operon (4266993 . . . 4267706)/note = "predicted operon"/note = "ordered genes contained in the operon: yjbP" |
| lux-a.pk035.b7 | − | Operon complement(3348330 . . . 3350660)/note = "predicted operon"/note = "ordered genes contained in the operon: arcB" |
| lux-a.pk039.g11 | + | Operon (2923370 . . . 2924218)/note = "predicted operon"/note = "ordered genes contained in the operon: b2794" |
| lux-a.pk045.d6 | + | Operon (1143671 . . . 1144045)/note = "predicted operon"/note = "ordered genes contained in the operon: b1085" |
| lux-a.pk050.g7 | + | Operon (1475639 . . . 1480225)/note = "predicted operon"/ |

TABLE 18-continued

Luxarray 1.0 Clone Collection

| Lux ID | Coding strand | Operon |
|---|---|---|
| | | note = "ordered genes contained in the operon: b1408 b1409 b1410 b1411" |
| lux-a.pk055.h3 | + | Operon (3089126 . . . 3091935)/note = "predicted operon"/note = "ordered genes contained in the operon: yggJ gshB b2948 b2949" |
| lux-a.pk063.d5 | − | Operon complement(3545619 . . . 3550106)/note = "documented malPQ operon" |
| lux-a.pk070.c11 | − | Operon complement(1041253 . . . 1048555)/note = "predicted operon"/note = "ordered genes contained in the operon: yccC b0982 b0983 b0984 b0985 b0986" |
| lux-a.pk076.e8 | − | Operon complement(3056686 . . . 3057345)/note = "predicted operon"/note = "ordered genes contained in the operon: rpiA" |
| lux-a.pk082.c8 | + | Operon (3698192 . . . 3699463)/note = "predicted operon"/note = "ordered genes contained in the operon: yhjV" |
| lux-a.pk090.g5 | − | Operon complement(3043178 . . . 3043921)/note = "predicted operon"/note = "ordered genes contained in the operon: ygfF" |
| lux-a.pk005.b11 | − | Operon complement(2752029 . . . 2752785)/note = "predicted operon"/note = "ordered genes contained in the operon: b2618 b2619" |
| lux-a.pk0011.h8 | − | Operon (420210 . . . 421583)/note = "predicted operon"/note = "ordered genes contained in the operon: b0402" |
| lux-a.pk0020.g6 | − | Operon complement(587205 . . . 592401)/note = "documented nfrBA operon" |
| lux-a.pk0025.f1 | + | Operon (1892829 . . . 1894772)/note = "predicted operon"/note = "ordered genes contained in the operon: pabB yeaB" |
| lux-a.pk031.a3 | + | Operon (3405238 . . . 3407588)/note = "documented panF-prmA operon" |
| lux-a.pk035.c7 | − | Operon complement(3383856 . . . 3387041)/note = "predicted operon"/note = "ordered genes contained in the operon: yhcP yhcQ b3242" |
| lux-a.pk039.h3 | − | Operon complement(2868278 . . . 2870843)/note = "predicted operon"/note = "ordered genes contained in the operon: b2745 ygbB b2747 b2748" |
| lux-a.pk045.f3 | + | Operon (1463416 . . . 1465974)/note = "predicted operon"/note = "ordered genes contained in the operon: ydbA_1" |
| lux-a.pk050.h3 | + | Operon (4483786 . . . 4485968)/note = "predicted operon"/note = "ordered genes contained in the operon: yjgP yjgQ" |
| lux-a.pk055.h9 | + | Operon (784856 . . . 785908)/note = "documented aroG operon" |
| lux-a.pk063.d9 | + | Operon (705316 . . . 706980)/note = "predicted operon"/note = "ordered genes contained in the operon: glnS" |
| lux-a.pk070.d2 | − | Operon complement(859397 . . . 862761)/note = "predicted operon"/note = "ordered genes contained in the operon: b0823 b0824" |
| lux-a.pk076.f2 | + | Operon (1777641 . . . 1779363)/note = "predicted operon"/note = "ordered genes contained in the operon: b1697 b1698" |
| lux-a.pk082.d4 | + | Operon (4552145 . . . 4552918)/note = "predicted operon"/note = "ordered genes contained in the operon: uxuR" |
| lux-a.pk005.b6 | + | Operon (2151891 . . . 2160901)/note = "predicted operon"/note = "ordered genes contained in the operon: b2074 b2075 b2076 b2077" |
| lux-a.pk0012.c3 | + | Operon (3478926 . . . 3482073)/note = "predicted operon"/note = "ordered genes contained in the operon: yheS yheT yheU" |
| lux-a.pk0020.h11 | − | Operon complement(2500010 . . . 2506262)/note = "predicted operon"/note = "ordered genes contained in the operon: b2383 b2384 b2385 b2386 b2387" |
| lux-a.pk0025.f3 | + | Operon (2194494 . . . 2201931)/note = "predicted operon"/note = "ordered genes contained in the operon: molR molR molR yehI" |
| lux-a.pk031.c11 | − | Operon complement(3146992 . . . 3147486)/note = "predicted operon"/note = "ordered genes contained in the operon: b3002" |
| lux-a.pk035.g11 | + | Operon (3101031 . . . 3102386)/note = "predicted operon"/note = "ordered genes contained in the operon: mutY b2962" |
| lux-a.pk039.h5 | − | Operon complement(2469097 . . . 2471266)/note = "predicted operon"/note = "ordered genes contained in the operon: b2354 b2355 b2356 b2357 b2358" |
| lux-a.pk045.g1 | − | Operon complement(4346893 . . . 4349240)/note = "predicted operon"/note = "ordered genes contained in the operon: yjdG yjdH" |
| lux-a.pk051.b1 | − | Operon complement(1158585 . . . 1160774)/note = "predicted operon"/note = "ordered genes contained in the operon: fhuE" |

TABLE 18-continued

Luxarray 1.0 Clone Collection

| Lux ID | Coding strand | Operon |
|---|---|---|
| lux-a.pk056.a11 | + | Operon (571689 . . . 572956)/note = "predicted operon"/note = "ordered genes contained in the operon: b0547 b0548 b0549 b0550" |
| lux-a.pk063.e1 | − | Operon complement(1181006 . . . 1184817)/note = "documented potABCD operon" |
| lux-a.pk070.e2 | + | Operon (624108 . . . 628520)/note = "documented entCEBA operon" |
| lux-a.pk076.f8 | − | Operon complement(3640010 . . . 3642812)/note = "predicted operon"/note = "ordered genes contained in the operon: yhiQ prlC" |
| lux-a.pk082.d5 | − | Operon complement(2706774 . . . 2708032)/note = "documented rpoE-rseA operon" |
| lux-a.pk005.e12 | + | Operon (4435285 . . . 4435785)/note = "predicted operon"/note = "ordered genes contained in the operon: b4215" |
| lux-a.pk0012.c7 | − | Operon complement(3472315 . . . 3474089)/note = "predicted operon"/note = "ordered genes contained in the operon: yheL b3344 yheN b3346" |
| lux-a.pk0020.h5 | − | Operon complement(1841855 . . . 1844984)/note = "predicted operon"/note = "ordered genes contained in the operon: b1762 topB" |
| lux-a.pk0025.f5 | + | Operon (164730 . . . 167264)/note = "predicted operon"/note = "ordered genes contained in the operon: mrcB" |
| lux-a.pk031.c7 | − | Operon complement(3031677 . . . 3034226)/note = "documented prfB-lysS operon" |
| lux-a.pk035.h9 | − | Operon complement(1863750 . . . 1864496)/note = "predicted operon"/note = "ordered genes contained in the operon: b1782" |
| lux-a.pk040.a11 | + | Operon (1710793 . . . 1712295)/note = "predicted operon"/note = "ordered genes contained in the operon: b1634" |
| lux-a.pk045.g4 | − | Operon complement(2833196 . . . 2835448)/note = "predicted operon"/note = "ordered genes contained in the operon: hypF" |
| lux-a.pk051.b11 | − | Operon complement(3112567 . . . 3117128)/note = "predicted operon"/note = "ordered genes contained in the operon: b2973 b2974" |
| lux-a.pk056.b3 | − | Operon complement(2948657 . . . 2956906)/note = "predicted operon"/note = "ordered genes contained in the operon: recD recB ptr" |
| lux-a.pk063.e8 | + | Operon (1807404 . . . 1808072)/note = "predicted operon"/note = "ordered genes contained in the operon: b1727" |
| lux-a.pk070.e4 | + | Operon (2589267 . . . 2590754)/note = "predicted operon"/note = "ordered genes contained in the operon: yffB dapE" |
| lux-a.pk077.a11 | − | Operon complement(608682 . . . 611717)/note = "documented fepA-entD operon" |
| lux-a.pk082.e8 | + | Operon (4028751 . . . 4032033)/note = "predicted operon"/note = "ordered genes contained in the operon: pepQ yigZ trkH" |
| lux-a.pk005.f6 | + | Operon (3602024 . . . 3602879)/note = "predicted operon"/note = "ordered genes contained in the operon: yhhF b3466" |
| lux-a.pk0012.e3 | + | Operon (3540803 . . . 3541681)/note = "predicted operon"/note = "ordered genes contained in the operon: yhgA" |
| lux-a.pk0021.a10 | + | Operon (3285731 . . . 3290073)/note = "predicted operon"/note = "ordered genes contained in the operon: yraI yraJ yraK" |
| lux-a.pk0025.g11 | − | Operon complement(4159749 . . . 4160849)/note = "predicted operon"/note = "ordered genes contained in the operon: trmA" |
| lux-a.pk031.d1 | − | Operon complement(1396798 . . . 1397550)/note = "documented fnr operon" |
| lux-a.pk036.a5 | − | Operon complement(4586446 . . . 4588864)/note = "predicted operon"/note = "ordered genes contained in the operon: yjiX yjiY" |
| lux-a.pk040.b5 | − | Operon complement(3913181 . . . 3920080)/note = "documented atpIBEFHAGDC operon" |
| lux-a.pk046.a5 | + | Operon (1846861 . . . 1848717)/note = "predicted operon"/note = "ordered genes contained in the operon: sppA" |
| lux-a.pk051.c11 | − | Operon complement(1607253 . . . 1608704)/note = "documented uxaB operon" |
| lux-a.pk056.b4 | − | Operon complement(1588878 . . . 1590466)/note = "documented hipBA operon" |
| lux-a.pk063.g7 | + | Operon (1741481 . . . 1742854)/note = "predicted operon"/note = "ordered genes contained in the operon: ydhE" |
| lux-a.pk070.f11 | + | Operon (3834580 . . . 3835764)/note = "predicted operon"/note = "ordered genes contained in the operon: yicK" |

TABLE 18-continued

Luxarray 1.0 Clone Collection

| Lux ID | Coding strand | Operon |
|---|---|---|
| lux-a.pk077.a3 | − | Operon complement(3130469 . . . 3131972)/note = "predicted operon"/note = "ordered genes contained in the operon: b2984 b2985" |
| lux-a.pk082.g4 | + | Operon (108279 . . . 110984)/note = "predicted operon"/note = "ordered genes contained in the operon: secA" |
| lux-a.pk005.g10 | + | Operon (1486256 . . . 1487695)/note = "predicted operon"/note = "ordered genes contained in the operon: aldA" |
| lux-a.pk0012.f11 | + | Operon (45807 . . . 47138)/note = "predicted operon"/note = "ordered genes contained in the operon: yaaU" |
| lux-a.pk0021.b6 | − | Operon complement(3427403 . . . 3429566)/note = "predicted operon"/note = "ordered genes contained in the operon: yrdB aroE yrdC yrdD" |
| lux-a.pk0025.g5 | + | Operon (738224 . . . 740148)/note = "predicted operon"/note = "ordered genes contained in the operon: ybgA phrB" |
| lux-a.pk031.e7 | + | Operon (27293 . . . 28207)/note = "predicted operon"/note = "ordered genes contained in the operon: yaaF" |
| lux-a.pk036.b6 | − | Operon complement(4428899 . . . 4429561)/note = "predicted operon"/note = "ordered genes contained in the operon: b4209" |
| lux-a.pk040.b7 | − | Operon complement(1582231 . . . 1584510)/note = "predicted operon"/note = "ordered genes contained in the operon: b1501" |
| lux-a.pk046.b5 | − | Operon complement(3044188 . . . 3048687)/note = "documented gcvTHP operon" |
| lux-a.pk051.d10 | − | Operon complement(4156969 . . . 4158303)/note = "predicted operon"/note = "ordered genes contained in the operon: udhA" |
| lux-a.pk056.c3 | − | Operon complement(332725 . . . 333657)/note = "predicted operon"/note = "ordered genes contained in the operon: b0316" |
| lux-a.pk064.c10 | − | Operon complement(2945779 . . . 2947122)/note = "predicted operon"/note = "ordered genes contained in the operon: b2817" |
| lux-a.pk070.g5 | + | Operon (4328080 . . . 4329582)/note = "documented proP operon" |
| lux-a.pk077.a9 | − | Operon complement(229967 . . . 230881)/note = "predicted operon"/note = "ordered genes contained in the operon: yafC" |
| lux-a.pk082.h2 | + | Operon (1753722 . . . 1755134)/note = "predicted operon"/note = "ordered genes contained in the operon: pykF" |
| lux-a.pk005.g2 | + | Operon (4049619 . . . 4050998)/note = "predicted operon"/note = "ordered genes contained in the operon: hemN" |
| lux-a.pk0015.d6 | + | Operon (1218824 . . . 1220344)/note = "predicted operon"/note = "ordered genes contained in the operon: b1169" |
| lux-a.pk0021.b8 | + | Operon (3928943 . . . 3930502)/note = "predicted operon"/note = "ordered genes contained in the operon: kup" |
| lux-a.pk0025.h1 | + | Operon (1785469 . . . 1786302)/note = "predicted operon"/note = "ordered genes contained in the operon: ydiA" |
| lux-a.pk031.e9 | + | Operon (533140 . . . 535710)/note = "predicted operon"/note = "ordered genes contained in the operon: gcl gip" |
| lux-a.pk036.b9 | + | Operon (938651 . . . 939943)/note = "predicted operon"/note = "ordered genes contained in the operon: serS" |
| lux-a.pk040.c9 | − | Operon complement(583903 . . . 586131)/note = "documented envY-ompT operon" |
| lux-a.pk046.c1 | + | Operon (535810 . . . 538311)/note = "predicted operon"/note = "ordered genes contained in the operon: b0509 b0510 b0511" |
| lux-a.pk051.d5 | + | Operon (638168 . . . 640541)/note = "documented ahpCF operon" |
| lux-a.pk056.d6 | + | Operon (1360767 . . . 1364839)/note = "predicted operon"/note = "ordered genes contained in the operon: aldH ordL goaG" |
| lux-a.pk064.c7 | − | Operon complement(1853015 . . . 1859356)/note = "predicted operon"/note = "ordered genes contained in the operon: b1771 b1772 b1773 b1774 b1775 b1776" |
| lux-a.pk070.g8 | − | Operon complement(408332 . . . 409243)/note = "predicted operon"/note = "ordered genes contained in the operon: yaiD" |
| lux-a.pk077.b1 | − | Operon complement(751452 . . . 752018)/note = "predicted operon"/note = "ordered genes contained in the operon: ybgD" |
| lux-a.pk083.a4 | − | Operon complement(505827 . . . 506306)/note = "predicted operon"/note = "ordered genes contained in the operon: b0481" |

TABLE 18-continued

Luxarray 1.0 Clone Collection

| Lux ID | Coding strand | Operon |
|---|---|---|
| lux-lacZ | | complement(360473 . . . 365529) |
| lux-a.pk0016.c4 | + | Operon (819107 . . . 819811)/note = "predicted operon"/note = "ordered genes contained in the operon: b0786" |
| lux-a.pk0021.c6 | – | Operon complement(1244902 . . . 1246599)/note = "predicted operon"/note = "ordered genes contained in the operon: treA" |
| lux-a.pk0025.h5 | – | Operon complement(764376 . . . 765098)/note = "predicted operon"/note = "ordered genes contained in the operon: farR" |
| lux-a.pk031.f10 | + | Operon (2261883 . . . 2263064)/note = "predicted operon"/note = "ordered genes contained in the operon: yeiO" |
| lux-a.pk036.d10 | + | Operon (4156069 . . . 4156986)/note = "documented oxyR operon" |
| lux-a.pk040.d7 | – | Operon complement(2671836 . . . 2677387)/note = "predicted operon"/note = "ordered genes contained in the operon: b2544 b2545 b2546 b2547 b2548" |
| lux-a.pk046.c12 | + | Operon (2282149 . . . 2284156)/note = "predicted operon"/note = "ordered genes contained in the operon: yejL yejM" |
| lux-a.pk051.g11 | – | Operon complement(1722760 . . . 1724082)/note = "predicted operon"/note = "ordered genes contained in the operon: b1647 b1648" |
| lux-a.pk056.f2 | + | Operon (1631646 . . . 1632236)/note = "predicted operon"/note = "ordered genes contained in the operon: b1545" |
| lux-a.pk064.f4 | + | Operon (3274643 . . . 3275442)/note = "predicted operon"/note = "ordered genes contained in the operon: sohA yhaV" |
| lux-a.pk071.a11 | – | Operon complement(906075 . . . 910272)/note = "predicted operon"/note = "ordered genes contained in the operon: b0869 b0870 poxB" |
| lux-a.pk077.c5 | + | Operon (3884457 . . . 3885821)/note = "predicted operon"/note = "ordered genes contained in the operon: thdF" |
| lux-a.pk083.d3 | – | Operon complement(2436962 . . . 2438140)/note = "predicted operon"/note = "ordered genes contained in the operon: b2322" |
| lux-a.pk005.g3 | – | Operon complement(841019 . . . 841423)/note = "predicted operon"/note = "ordered genes contained in the operon: b0806" |
| lux-a.pk0016.e11 | – | Operon complement(4333272 . . . 4334609)/note = "predicted operon"/note = "ordered genes contained in the operon: yjdD" |
| lux-a.pk0021.d4 | + | Operon (4133655 . . . 4134593)/note = "predicted operon"/note = "ordered genes contained in the operon: yijE" |
| lux-a.pk0026.a12 | + | Operon (4448633 . . . 4452152)/note = "predicted operon"/note = "ordered genes contained in the operon: ytfR ytfS ytfT yjfF" |
| lux-a.pk031.f7 | + | Operon (3735126 . . . 3737156)/note = "documented malS operon" |
| lux-a.pk036.d6 | – | Operon complement(837753 . . . 840754)/note = "predicted operon"/note = "ordered genes contained in the operon: b0804 b0805" |
| lux-a.pk040.e4 | + | Operon (3791614 . . . 3795834)/note = "documented rfaDFCL operon" |
| lux-a.pk046.c3 | + | Operon (2765725 . . . 2766594)/note = "predicted operon"/note = "ordered genes contained in the operon: b2632" |
| lux-a.pk051.h4 | – | Operon complement(2943058 . . . 2943864)/note = "predicted operon"/note = "ordered genes contained in the operon: b2812" |
| lux-a.pk056.g9 | – | Operon complement(717485 . . . 719683)/note = "documented speF operon" |
| lux-a.pk064.f8 | + | Operon (3058870 . . . 3064300)/note = "predicted operon"/note = "ordered genes contained in the operon: sbm ygfD b2919 b2920" |
| lux-a.pk071.a4 | – | Operon complement(4051449 . . . 4055614)/note = "documented glnALG operon" |
| lux-a.pk077.c7 | + | Operon (3416027 . . . 3416248)/note = "predicted operon"/note = "ordered genes contained in the operon: yhdV" |
| lux-a.pk083.e7 | – | Operon complement(1120784 . . . 1121830)/note = "documented pyrC operon" |
| lux-lacZ | | complement(360473 . . . 365529) |
| lux-a.pk0016.g4 | + | Operon (2848670 . . . 2852287)/note = "documented hypABCDE operon" |
| lux-a.pk0021.e5 | + | Operon (331595 . . . 332683)/note = "predicted operon"/note = "ordered genes contained in the operon: yahA" |
| lux-a.pk0026.b5 | + | Operon (3229306 . . . 3231324)/note = "predicted operon"/note = "ordered genes contained in the operon: ygjL" |
| lux-a.pk031.g10 | + | Operon (1097070 . . . 1098047)/note = "predicted operon"/note = "ordered genes contained in the operon: b1033" |

TABLE 18-continued

Luxarray 1.0 Clone Collection

| Lux ID | Coding strand | Operon |
|---|---|---|
| lux-a.pk036.d7 | − | Operon complement(1665368 . . . 1666588)/note = "predicted operon"/note = "ordered genes contained in the operon: mlc" |
| lux-a.pk040.e5 | + | Operon (4422696 . . . 4424135)/note = "documented rpsF-priB-rpsR-rplI operon" |
| lux-a.pk046.e6 | − | Operon complement(4085688 . . . 4090404)/note = "predicted operon"/note = "ordered genes contained in the operon: frvR frvX frvB frvA" |
| lux-a.pk052.a4 | − | Operon complement(476291 . . . 477847)/note = "predicted operon"/note = "ordered genes contained in the operon: b0457" |
| lux-a.pk056.h3 | + | Operon (1725861 . . . 1726268)/note = "predicted operon"/note = "ordered genes contained in the operon: b1651" |
| lux-a.pk064.g8 | − | Operon complement(2225343 . . . 2226859)/note = "predicted operon"/note = "ordered genes contained in the operon: yohG yohH" |
| lux-a.pk071.e1 | + | Operon (3244277 . . . 3245068)/note = "predicted operon"/note = "ordered genes contained in the operon: exuR" |
| lux-a.pk077.d11 | + | Operon (3291041 . . . 3294625)/note = "predicted operon"/note = "ordered genes contained in the operon: yraM yraN yraO yraP" |
| lux-a.pk083.g7 | + | Operon (1532048 . . . 1532893)/note = "predicted operon"/note = "ordered genes contained in the operon: b1463" |
| lux-a.pk006.b2 | − | Operon complement(2417861 . . . 2418505)/note = "predicted operon"/note = "ordered genes contained in the operon: b2301" |
| lux-a.pk0016.h6 | + | Operon (8238 . . . 9191)/note = "predicted operon"/note = "ordered genes contained in the operon: talB" |
| lux-a.pk0021.e6 | + | Operon (1944176 . . . 1944877)/note = "predicted operon"/note = "ordered genes contained in the operon: yebB" |
| lux-a.pk0026.c12 | − | Operon complement(3875333 . . . 3877747)/note = "predicted operon"/note = "ordered genes contained in the operon: gyrB" |
| lux-a.pk031.g7 | − | Operon complement(1020953 . . . 1023571)/note = "predicted operon"/note = "ordered genes contained in the operon: b0960 yccF" |
| lux-a.pk036.d9 | − | Operon complement(3250958 . . . 3251854)/note = "predicted operon"/note = "ordered genes contained in the operon: yhaJ" |
| lux-a.pk040.g11 | + | Operon (1321244 . . . 1324665)/note = "predicted operon"/note = "ordered genes contained in the operon: b1266 yciO yciQ" |
| lux-a.pk046.e9 | − | Operon complement(184257 . . . 188650)/note = "predicted operon"/note = "ordered genes contained in the operon: yaeI b0165 dapD glnD" |
| lux-a.pk052.a9 | − | Operon complement(4280832 . . . 4282792)/note = "predicted operon"/note = "ordered genes contained in the operon: yjcG yjcH" |
| lux-a.pk057.f5 | − | Operon complement(4458096 . . . 4460234)/note = "predicted operon"/note = "ordered genes contained in the operon: nrdD" |
| lux-a.pk064.h7 | − | Operon complement(2748136 . . . 2748729)/note = "predicted operon"/note = "ordered genes contained in the operon: grpE" |
| lux-a.pk071.f7 | − | Operon complement(2547666 . . . 2548592)/note = "predicted operon"/note = "ordered genes contained in the operon: b2431" |
| lux-a.pk077.d9 | + | Operon (4628275 . . . 4630239)/note = "predicted operon"/note = "ordered genes contained in the operon: slt" |
| lux-a.pk083.h2 | − | Operon complement(1169741 . . . 1173187)/note = "predicted operon"/note = "ordered genes contained in the operon: mfd" |
| lux-lacZ | | complement(360473 . . . 365529) |
| lux-a.pk0017.a4 | + | Operon (142779 . . . 144472)/note = "predicted operon"/note = "ordered genes contained in the operon: yadG yadH" |
| lux-a.pk0021.e8 | − | Operon complement(4612249 . . . 4614634)/note = "predicted operon"/note = "ordered genes contained in the operon: yjjW yjjI" |
| lux-a.pk0026.c7 | + | Operon (2318063 . . . 2321271)/note = "predicted operon"/note = "ordered genes contained in the operon: atoS atoC" |
| lux-a.pk031.g8 | − | Operon complement(3129356 . . . 3130333)/note = "predicted operon"/note = "ordered genes contained in the operon: b2983" |
| lux-a.pk036.e6 | − | Operon complement(3836802 . . . 3837620)/note = "predicted operon"/note = "ordered genes contained in the operon: nlpA" |
| lux-a.pk040.g3 | − | Operon complement(3927224 . . . 3928744)/note = "predicted |

TABLE 18-continued

Luxarray 1.0 Clone Collection

| Lux ID | Coding strand | Operon |
|---|---|---|
| | | operon"/note = "ordered genes contained in the operon: yieN" |
| lux-a.pk046.f11 | + | Operon (4014920 . . . 4016347)/note = "predicted operon"/note = "ordered genes contained in the operon: yigN" |
| lux-a.pk052.b6 | + | Operon (3995596 . . . 3997758)/note = "documented uvrD operon" |
| lux-a.pk058.a11 | – | Operon complement(947883 . . . 948791)/note = "predicted operon"/note = "ordered genes contained in the operon: b0900" |
| lux-a.pk064.h8 | – | Operon complement(1550852 . . . 1551892)/note "predicted operon"/note = "ordered genes contained in the operon: b1478" |
| lux-a.pk071.g2 | – | Operon complement(4585479 . . . 4586333)/note = "predicted operon"/note = "ordered genes contained in the operon: yjiA" |
| lux-a.pk077.e4 | – | Operon complement(1596641 . . . 1598233)/note = "predicted operon"/note = "ordered genes contained in the operon: b1511" |
| lux-a.pk085.a11 | + | Operon (2435970 . . . 2436965)/note "predicted operon"/note = "ordered genes contained in the operon: div" |
| lux-a.pk006.b4 | – | Operon complement(1313880 . . . 1314116)/note = "predicted operon"/note = "ordered genes contained in the operon: yciG" |
| lux-a.pk0017.c10 | – | Operon complement(4413595 . . . 4413897)/note "predicted operon"/note = "ordered genes contained in the operon: yjfN" |
| lux-a.pk0021.f6 | – | Operon complement(3215197 . . . 3216717)/note = "predicted operon"/note = "ordered genes contained in the operon: air" |
| lux-a.pk0026.c8 | + | Operon (2496691 . . . 2500007)/note = "predicted operon"/note = "ordered genes contained in the operon: b2380 b2381 b2382" |
| lux-a.pk031.g9 | + | Operon (358023 . . . 360370)/note = "documented cynTSX operon" |
| lux-a.pk036.e8 | – | Operon complement(2455035 . . . 2458489)/note = "predicted operon"/note = "ordered genes contained in the operon: b2341 b2342" |
| lux-a.pk040.g4 | – | Operon complement(3137731 . . . 3143155)/note = "documented hybGFEDCBA operon" |
| lux-a.pk046.g7 | – | Operon complement(1355826 . . . 1357265)/note = "predicted operon"/note = "ordered genes contained in the operon: b1296" |
| lux-a.pk052.b7 | – | Operon complement(1884888 . . . 1886015)/note = "predicted operon"/note = "ordered genes contained in the operon: rnd" |
| lux-a.pk058.a9 | + | Operon (3963322 . . . 3963705)/note = "predicted operon"/note = "ordered genes contained in the operon: trxA" |
| lux-a.pk065.d9 | – | Operon complement(1878910 . . . 1879854)/note = "predicted operon"/note = "ordered genes contained in the operon: b1799" |
| lux-a.pk071.g4 | – | Operon complement(3160760 . . . 3161497)/note = "predicted operon"/note = "ordered genes contained in the operon: plsC" |
| lux-a.pk077.f10 | + | Operon (2991660 . . . 2991878)/note = "predicted operon"/note = "ordered genes contained in the operon: b2853" |
| lux-a.pk085.a5 | + | Operon (4254694 . . . 4256700)/note = "documented lexA-dinF operon" |
| lux-a.pk006.c9 | + | Operon (4381375 . . . 4382919)/note = "predicted operon"/note = "ordered genes contained in the operon: yjeM" |
| lux-a.pk0017.c7 | + | Operon (504138 . . . 505790)/note = "predicted operon"/note = "ordered genes contained in the operon: ushA" |
| lux-a.pk0021.g11 | + | Operon (458112 . . . 460466)/note = "predicted operon"/note = "ordered genes contained in the operon: lon" |
| lux-a.pk0026.d1 | + | Operon (113444 . . . 114487)/note = "predicted operon"/note = "ordered genes contained in the operon: guaC" |
| lux-a.pk032.b10 | + | Operon (1262937 . . . 1268242)/note = "predicted operon"/note = "ordered genes contained in the operon: hemA prfA hemK b1213 ychA kdsA" |
| lux-a.pk036.h7 | + | Operon (182445 . . . 183620)/note = "predicted operon"/note = "ordered genes contained in the operon: yaeG" |
| lux-a.pk040.g6 | – | Operon complement(2434735 . . . 2435871)/note = "predicted operon"/note = "ordered genes contained in the operon: pdxB" |
| lux-a.pk047.a10 | + | Operon (2011251 . . . 2017535)/note = "documented fliFGHIJK operon" |
| lux-a.pk052.c11 | + | Operon (1124785 . . . 1126952)/note = "predicted operon"/note = "ordered genes contained in the operon: rimJ yceH" |
| lux-a.pk058.c1 | – | Operon complement(3253729 . . . 3255597)/note = "predicted operon"/note = "ordered genes contained in the operon: |

TABLE 18-continued

Luxarray 1.0 Clone Collection

| Lux ID | Coding strand | Operon |
|---|---|---|
| | | yhaN yhaO" |
| lux-a.pk065.e4 | + | Operon (3272923 . . . 3274494)/note = "predicted operon"/note = "ordered genes contained in the operon: yhaG" |
| lux-a.pk071.g6 | − | Operon complement(4454888 . . . 4455439)/note = "predicted operon"/note = "ordered genes contained in the operon: yjgA" |
| lux-a.pk077.f12 | − | Operon complement(2841059 . . . 2848458)/note = "documented hycABCDEFGH operon" |
| lux-a.pk085.c1 | − | Operon complement(944154 . . . 944780)/note = "predicted operon"/note = "ordered genes contained in the operon: ycaC" |
| lux-a.pk006.e10 | − | Operon complement(2122545 . . . 2131419)/note = "predicted operon"/note = "ordered genes contained in the operon: yefD yefC yefB yefA b2054 b2055 b2056 b2057 wcaB b2059" |
| lux-a.pk0017.c9 | + | Operon (3958292 . . . 3960313)/note = "predicted operon"/note = "ordered genes contained in the operon: rep" |
| lux-a.pk0022.a2 | − | Operon complement(2536692 . . . 2541548)/note = "documented cysPUWAM operon" |
| lux-a.pk0026.e10 | + | Operon (3610600 . . . 3611187)/note = "predicted operon"/note = "ordered genes contained in the operon: yhhU" |
| lux-a.pk032.b2 | + | Operon (3281811 . . . 3284666)/note = "predicted operon"/note = "ordered genes contained in the operon: agaB agaC agaD agaI" |
| lux-a.pk036.h9 | + | Operon (830095 . . . 831459)/note = "predicted operon"/note = "ordered genes contained in the operon: rhlE" |
| lux-a.pk041.a10 | − | Operon complement(3780269 . . . 3781755)/note = "predicted operon"/note = "ordered genes contained in the operon: gpsA secB" |
| lux-a.pk047.a11 | + | Operon (4016442 . . . 4021926)/note = "predicted operon"/note = "ordered genes contained in the operon: yigO yigP yigQ yigTa yigTb yigTc yigU yigW yigW" |
| lux-a.pk052.c5 | − | Operon complement(2574118 . . . 2576397)/note = "predicted operon"/note = "ordered genes contained in the operon: b2463" |
| lux-a.pk058.c11 | − | Operon complement(1980578 . . . 1984151)/note = "documented araFG-b1899-araH operon" |
| lux-a.pk065.f11 | − | Operon complement(3376505 . . . 3377632)/note = "predicted operon"/note = "ordered genes contained in the operon: yhcM" |
| lux-a.pk072.a10 | − | Operon complement(149715 . . . 152854)/note = "predicted operon"/note = "ordered genes contained in the operon: yadC yadK yadL yadM" |
| lux-a.pk077.f3 | + | Operon (3965531 . . . 3972101)/note = "predicted operon"/note = "ordered genes contained in the operon: rfe b3785 rffE rffD rffG rffH" |
| lux-a.pk085.f1 | − | Operon complement(54755 . . . 57109)/note = "predicted operon"/note = "ordered genes contained in the operon: imp" |
| lux-a.pk006.f7 | − | Operon complement(3865689 . . . 3866939)/note = "predicted operon"/note = "ordered genes contained in the operon: yidR" |
| lux-a.pk0017.d3 | + | Operon (4476036 . . . 4476452)/note = "predicted operon"/note = "ordered genes contained in the operon: yjgD" |
| lux-a.pk0022.b1 | − | Operon complement(4025199 . . . 4028561)/note = "documented fadBA operon" |
| lux-a.pk0026.f11 | − | Operon complement(78848 . . . 83708)/note = "documented leuLABCD operon" |
| lux-a.pk032.c3 | − | Operon complement(2744454 . . . 2745815)/note = "predicted operon"/note = "ordered genes contained in the operon: ffh" |
| lux-a.pk037.a3 | + | Operon (3857880 . . . 3858803)/note = "predicted operon"/note = "ordered genes contained in the operon: b3680" |
| lux-a.pk041.a6 | − | Operon complement(640662 . . . 641090)/note = "predicted operon"/note = "ordered genes contained in the operon: b0607" |
| lux-a.pk047.a6 | − | Operon complement(661975 . . . 663186)/note = "predicted operon"/note = "ordered genes contained in the operon: dacA" |
| lux-a.pk052.d6 | − | Operon complement(3892901 . . . 3894238)/note = "predicted operon"/note = "ordered genes contained in the operon: yieG" |
| lux-a.pk058.c9 | − | Operon complement(1187539 . . . 1189670)/note = "documented phoQP operon" |
| lux-a.pk065.f9 | + | Operon (2135858 . . . 2137507)/note = "predicted operon"/note = "ordered genes contained in the operon: b2063" |

TABLE 18-continued

Luxarray 1.0 Clone Collection

| Lux ID | Coding strand | Operon |
|---|---|---|
| lux-a.pk072.b1 | − | Operon complement(1846149 ... 1846700)/note = "predicted operon"/note = "ordered genes contained in the operon: ydjA" |
| lux-a.pk077.h3 | − | Operon complement(4534182 ... 4535162)/note = "predicted operon"/note = "ordered genes contained in the operon: yjhS" |
| lux-a.pk085.g10 | − | Operon complement(1015762 ... 1017522)/note = "predicted operon"/note = "ordered genes contained in the operon: b0955" |
| lux-a.pk006.h1 | + | Operon (989845 ... 992457)/note = "predicted operon"/note = "ordered genes contained in the operon: pepN" |
| lux-a.pk0017.e3 | − | Operon complement(2334813 ... 2337440)/note = "documented gyrA operon" |
| lux-a.pk0022.b3 | − | Operon complement(4188313 ... 4193677)/note = "documented thiCEFGH operon" |
| lux-a.pk0026.f3 | + | Operon (4276058 ... 4277407)/note = "predicted operon"/note = "ordered genes contained in the operon: yjcD" |
| lux-a.pk032.d2 | + | Operon (2461032 ... 2462090)/note = "predicted operon"/note = "ordered genes contained in the operon: b2345" |
| lux-a.pk037.c11 | − | Operon complement(824225 ... 829878)/note = "predicted operon"/note = "ordered genes contained in the operon: b0792 b0793 b0794 b0795 ybiH" |
| lux-a.pk041.b3 | − | Operon complement(3334604 ... 3337706)/note = "predicted operon"/note = "ordered genes contained in the operon: yrbB yrbC b3193 yrbE b3195" |
| lux-a.pk047.b4 | + | Operon (2735619 ... 2736925)/note = "documented pheLA operon" |
| lux-a.pk052.d7 | + | Operon (1732459 ... 1733274)/note = "predicted operon"/note = "ordered genes contained in the operon: b1655" |
| lux-a.pk058.e10 | + | Operon (1928905 ... 1930083)/note = "predicted operon"/note = "ordered genes contained in the operon: purT" |
| lux-a.pk065.g3 | − | Operon complement(2246757 ... 2247638)/note = "predicted operon"/note = "ordered genes contained in the operon: yeiE" |
| lux-a.pk072.b6 | + | Operon (538371 ... 539732)/note = "predicted operon"/note = "ordered genes contained in the operon: b0512" |
| lux-a.pk078.b3 | − | Operon complement(383283 ... 383693)/note = "predicted operon"/note = "ordered genes contained in the operon: b0364" |
| lux-a.pk085.h9 | + | Operon (532235 ... 533050)/note = "predicted operon"/note = "ordered genes contained in the operon: b0506" |
| lux-a.pk006.h2 | − | Operon complement(2595851 ... 2597780)/note = "documented dapA-nlpB operon" |
| lux-a.pk0017.e7 | + | Operon (3656862 ... 3661157)/note = "predicted operon"/note = "ordered genes contained in the operon: yhiU yhiV" |
| lux-a.pk0022.b5 | − | Operon complement(4148026 ... 4150677)/note = "predicted operon"/note = "ordered genes contained in the operon: ppc" |
| lux-a.pk0026.g10 | + | Operon (940269 ... 944119)/note = "documented dmsABC operon" |
| lux-a.pk032.d7 | + | Operon (432226 ... 434780)/note = "predicted operon"/note = "ordered genes contained in the operon: ybaD ribD ribH nusB" |
| lux-a.pk037.c3 | − | Operon complement(658474 ... 661435)/note = "predicted operon"/note = "ordered genes contained in the operon: lipA ybeF lipB" |
| lux-a.pk041.d4 | + | Operon (1737935 ... 1739146)/note = "predicted operon"/note = "ordered genes contained in the operon: ydhC" |
| lux-a.pk047.c5 | − | Operon complement(3322642 ... 3325305)/note = "documented ftsJ-hflB operon" |
| lux-a.pk052.e11 | − | Operon complement(2712459 ... 2713385)/note = "predicted operon"/note = "ordered genes contained in the operon: yfiE" |
| lux-a.pk058.f2 | − | Operon complement(1942370 ... 1944000)/note = "documented ruvBA operon" |
| lux-a.pk065.g6 | + | Operon (3155664 ... 3156593)/note = "predicted operon"/note = "ordered genes contained in the operon: +" |
| lux-a.pk072.b8 | + | Operon (3018561 ... 3022207)/note = "predicted operon"/note = "ordered genes contained in the operon: b2880 b2881" |
| lux-a.pk078.c2 | − | Operon complement(288525 ... 289529)/note = "documented argF operon" |
| lux-a.pk086.a5 | − | Operon complement(4302191 ... 4304188)/note = "predicted operon"/note = "ordered genes contained in the operon: yjcS" |
| lux-a.pk007.a10 | − | Operon complement(2338437 ... 2342189)/note = "predicted operon"/note = "ordered genes contained in the operon: yfaL" |
| lux-a.pk0017.f11 | − | Operon complement(2633619 ... 2635415)/note = "predicted operon"/note = "ordered genes contained in the operon: b2510 b2511" |

TABLE 18-continued

Luxarray 1.0 Clone Collection

| Lux ID | Coding strand | Operon |
|---|---|---|
| lux-a.pk0022.c1 | + | Operon (334504 . . . 339313)/note = "predicted operon"/note = "ordered genes contained in the operon: b0318 b0319 b0320 b0321 b0322" |
| lux-a.pk0026.g2 | − | Operon complement(786066 . . . 786818)/note = "predicted operon"/note = "ordered genes contained in the operon: gpmA" |
| lux-a.pk032.e4 | + | Operon (2141288 . . . 2144605)/note = "predicted operon"/note = "ordered genes contained in the operon: yegE" |
| lux-a.pk037.c8 | − | Operon complement(262552 . . . 263231)/note = "predicted operon"/note = "ordered genes contained in the operon: b0245 b0246" |
| lux-a.pk041.d8 | − | Operon complement(622777 . . . 623733)/note = "documented fepB operon" |
| lux-a.pk047.c6 | + | Operon (3154754 . . . 3155464)/note = "predicted operon"/note = "ordered genes contained in the operon: b3012" |
| lux-a.pk052.f1 | − | Operon complement(3665421 . . . 3666818)/note = "predicted operon"/note = "ordered genes contained in the operon: yhjA" |
| lux-a.pk058.f3 | − | Operon complement(3371333 . . . 3372124)/note "predicted operon"/note = "ordered genes contained in the operon: b3226" |
| lux-a.pk065.h2 | − | Operon complement(2009370 . . . 2009891)/note = "predicted operon"/note = "ordered genes contained in the operon: b1933 b1934" |
| lux-a.pk072.d1 | − | Operon complement(4300657 . . . 4301688)/note = "predicted operon"/note = "ordered genes contained in the operon: yjcR" |
| lux-a.pk078.c2 | − | Operon complement(4474870 . . . 4475874)/note = "documented argI operon" |
| lux-a.pk086.b7 | + | Operon (1481142 . . . 1484987)/note = "predicted operon"/note = "ordered genes contained in the operon: hrpA" |

The numbers in parenthesis represent each end of the nucleotide sequence designation in the *E. coli* genomic sequence. The sequence designation is based on Blattner et al. ((1997) Science 277:1453–1462)

TABLE 19

| | | |
|---|---|---|
| lux-z.pk013.a15 | − | Operon complement(3366649 . . . 3370239) note = "predicted operon" note = "ordered genes contained in the operon: b3221 yhcI b3223 nanT" |
| lux-z.pk013.g17 | − | Operon complement(4488774 . . . 4490093) note = "predicted operon" note = "ordered genes contained in the operon: yjgT" |
| lux-z.pk013.i9 | + | Operon 3128193 . . . 3129209 note = "predicted operon" note = "ordered genes contained in the operon: yi52_9" |
| lux-z.pk013.k1 | − | Operon complement(2978786 . . . 2980204) note = "documented araE operon" |
| lux-z.pk013.k11 | + | Operon 2027561 . . . 2028481 note = "predicted operon" note = "ordered genes contained in the operon: yedA" |
| lux-z.pk013.k5 | + | Operon 2418641 . . . 2419288 note = "predicted operon" note = "ordered genes contained in the operon: b2302" |
| lux-z.pk013.o5 | − | Operon complement(1347004 . . . 1348209) note = "predicted operon" note = "ordered genes contained in the operon: b1287" |
| lux-z.pk014.a14 | + | Operon 1063259 . . . 1064515 note = "predicted operon" note = "ordered genes contained in the operon: yccE" |
| lux-z.pk014.a22 | + | Operon 557402 . . . 557977 note = "predicted operon" note = "ordered genes contained in the operon: b0530" |
| lux-z.pk014.c16 | + | Operon 607288 . . . 608400 note = "predicted operon" note = "ordered genes contained in the operon: yi81_2" |
| lux-z.pk014.c5 | − | Operon complement(1561358 . . . 1565164) note = "predicted operon" note = "ordered genes contained in the operon: b1489 b1490" |
| lux-z.pk014.g11 | − | Operon complement(3055198 . . . 3056430) note = "documented serA operon" |
| lux-z.pk014.h9 | + | Operon 948891 . . . 949481 note = "predicted operon" note = "ordered genes contained in the operon: ycaK" |
| lux-z.pk014.k13 | + | Operon 3769908 . . . 3773786 note = "documented mtlADR operon" |
| lux-z.pk014.l1 | + | Operon 3132146 . . . 3132838 note = "predicted operon" note = "ordered genes contained in the operon: b2986" |

TABLE 19-continued

| | | |
|---|---|---|
| lux-z.pk014.m1 | + | Operon 2752917 ... 2753399 note = "predicted operon" note = "ordered genes contained in the operon: smpB" |
| lux-z.pk014.n19 | − | Operon complement(4439115 ... 4439753) note = "predicted operon" note = "ordered genes contained in the operon: msrA" |
| lux-z.pk014.o9 | − | Operon complement(2486043 ... 2488206) note = "predicted operon" note = "ordered genes contained in the operon: b2371 b2372" |
| lux-z.pk014.p3 | + | Operon 4077307 ... 4077549 note = "predicted operon" note = "ordered genes contained in the operon: yiiF" |
| lux-z.pk014.p4 | − | Operon complement(1930139 ... 1932628) note = "predicted operon" note = "ordered genes contained in the operon: eda edd" |
| lux-z.pk014.p8 | − | Operon complement(1122630 ... 1123277) note = "predicted operon" note = "ordered genes contained in the operon: grxB" |
| lux-z.pk015.a7 | + | Operon 3408908 ... 3409204 note = "documented fis operon" |
| lux-z.pk015.b23 | + | Operon 4059826 ... 4061091 note = "predicted operon" note = "ordered genes contained in the operon: yihN" |
| lux-z.pk015.c7 | + | Operon 2758568 ... 2759194 note = "predicted operon" note = "ordered genes contained in the operon: b2626" |
| lux-z.pk015.d10 | + | Operon 2745907 ... 2748081 note = "predicted operon" note = "ordered genes contained in the operon: b2611 b2612 yfjD" |
| lux-z.pk015.e17 | − | Operon complement(2794358 ... 2794807) note = "predicted operon" note = "ordered genes contained in the operon: b2665" |
| lux-z.pk015.f1 | + | Operon 2321467 ... 2325313 note = "documented atoDAB operon" |
| lux-z.pk015.g1 | + | Operon 1509678 ... 1515026 note = "predicted operon" note = "ordered genes contained in the operon: b1440 b1441 b1442 b1443 b1444" |
| lux-z.pk015.g13 | + | Operon 3214420 ... 3215043 note = "predicted operon" note = "ordered genes contained in the operon: b3071" |
| lux-z.pk015.g23 | − | Operon complement(2828798 ... 2830387) note = "predicted operon" note = "ordered genes contained in the operon: ygaA" |
| lux-z.pk015.i5 | − | Operon complement(376759 ... 377592) note = "predicted operon" note = "ordered genes contained in the operon: b0355" |
| lux-z.pk015.n1 | − | Operon complement(586314 ... 587204) note = "predicted operon" note = "ordered genes contained in the operon: ybcH" |
| lux-z.pk015.n24 | + | Operon 2576686 ... 2579659 note = "predicted operon" note = "ordered genes contained in the operon: b2464 tktB" |
| lux-z.pk015.n4 | − | Operon complement(4145045 ... 4145896) note = "predicted operon" note = "ordered genes contained in the operon: yijO" |
| lux-z.pk015.p2 | − | Operon complement(3111560 ... 3112492) note = "predicted operon" note = "ordered genes contained in the operon: b2972" |
| lux-z.pk015.p6 | + | Operon 1768612 ... 1768995 note = "predicted operon" note = "ordered genes contained in the operon: b1689" |
| lux-z.pk016.a4 | − | Operon complement(4580819 ... 4584385) note = "predicted operon" note = "ordered genes contained in the operon: hsdR" |
| lux-z.pk016.c22 | + | Operon 4210813 ... 4211196 note = "predicted operon" note = "ordered genes contained in the operon: yjaA" |
| lux-z.pk016.c9 | + | Operon 1073465 ... 1074103 note = "predicted operon" note = "ordered genes contained in the operon: b1013" |
| lux-z.pk016.e11 | − | Operon complement(2812905 ... 2814461) note = "predicted operon" note = "ordered genes contained in the operon: gshA" |
| lux-z.pk016.f16 | + | Operon 2405581 ... 2406798 note = "predicted operon" note = "ordered genes contained in the operon: b2290" |
| lux-z.pk016.f6 | + | Operon 1234161 ... 1234880 note = "predicted operon" note = "ordered genes contained in the operon: fadR" |
| lux-z.pk016.h16 | + | Operon 3054261 ... 3054809 note = "predicted operon" note = "ordered genes contained in the operon: ygfA" |
| lux-z.pk016.i17 | − | Operon complement(2817403 ... 2820033) note = "predicted operon" note = "ordered genes contained in the operon: alaS" |
| lux-z.pk016.l2 | + | Operon 4041737 ... 4043209 note = "predicted operon" note = "ordered genes contained in the operon: yihF" |
| lux-z.pk016.l24 | + | Operon 1055484 ... 1056512 note = "predicted operon" note = "ordered genes contained in the operon: torT" |
| lux-z.pk016.n14 | − | Operon complement(1228706 ... 1229623) note = "predicted operon" note = "ordered genes contained in the operon: b1182" |
| lux-z.pk016.o11 | − | Operon complement(4108320 ... 4109087) note = "predicted operon" note = "ordered genes contained in the operon: tpiA" |
| lux-z.pk016.o17 | + | Operon 2475867 ... 2478550 note = "documented dsdXA operon" |
| lux-z.pk017.c2 | + | Operon 3550718 ... 3553423 note = "documented malT operon" |
| lux-z.pk017.g19 | + | Operon 420210 ... 421583 note = "predicted operon" note = "ordered genes contained in the operon: b0402" |
| lux-z.pk017.g23 | − | Operon complement(4468560 ... 4469969) note = "documented pyrBI operon" |

TABLE 19-continued

| | | |
|---|---|---|
| lux-z.pk017.i21 | − | Operon complement(3633838 . . . 3635040) note = "predicted operon" note = "ordered genes contained in the operon: yhiN" |
| lux-z.pk017.i4 | + | Operon 3004356 . . . 3005447 note = "predicted operon" note = "ordered genes contained in the operon: b2870" |
| lux-z.pk017.k15 | − | Operon complement(2657583 . . . 2659575) note = "predicted operon" note = "ordered genes contained in the operon: yfhF b2529 b2530" |
| lux-z.pk017.m18 | + | Operon 2270378 . . . 2275909 note = "predicted operon" note = "ordered genes contained in the operon: yejA yejB yejE yejF" |
| lux-z.pk018.a16 | − | Operon complement(3738738 . . . 3739211) note = "predicted operon" note = "ordered genes contained in the operon: not-yiaI" |
| lux-z.pk018.e4 | + | Operon 4256816 . . . 4257025 note = "predicted operon" note = "ordered genes contained in the operon: b4045" |
| lux-z.pk018.g18 | − | Operon complement(2488276 . . . 2489970) note = "predicted operon" note = "ordered genes contained in the operon: b2373" |
| lux-z.pk018.i2 | + | Operon 2037500 . . . 2039140 note = "predicted operon" note = "ordered genes contained in the operon: b1971 b1972" |
| lux-z.pk018.o10 | + | Operon 959463 . . . 960251 note = "predicted operon" note = "ordered genes contained in the operon: b0909" |
| lux-z.pk019.a18 | − | Operon complement(2242798 . . . 2244789) note = "documented cirA operon" |
| lux-z.pk019.a24 | − | Operon complement(4559066 . . . 4560244) note = "predicted operon" note = "ordered genes contained in the operon: yjiJ" |
| lux-z.pk019.b15 | + | Operon 4611194 . . . 4611829 note = "predicted operon" note = "ordered genes contained in the operon: yjjV" |
| lux-z.pk019.b21 | − | Operon complement(3309474 . . . 3310819) note = "predicted operon" note = "ordered genes contained in the operon: truB rbfA" |
| lux-z.pk019.c6 | − | Operon complement(4388035 . . . 4389048) note = "predicted operon" note = "ordered genes contained in the operon: yjeQ" |
| lux-z.pk019.e12 | + | Operon 4263361 . . . 4264440 note = "predicted operon" note = "ordered genes contained in the operon: alr" |
| lux-z.pk019.e2 | + | Operon 1225823 . . . 1226191 note = "predicted operon" note = "ordered genes contained in the operon: b1177" |
| lux-z.pk019.g1 | − | Operon complement(663325 . . . 668151) note = "predicted operon" note = "ordered genes contained in the operon: rlpA mrdB mrdA ybeA ybeB" |
| lux-z.pk019.h5 | − | Operon complement(1555136 . . . 1561100) note = "predicted operon" note = "ordered genes contained in the operon: b1483 b1484 b1485 b1486 b1487 b1488" |
| lux-z.pk019.j11 | + | Operon 2662383 . . . 2663264 note = "predicted operon" note = "ordered genes contained in the operon: b2534" |
| lux-z.pk019.j15 | + | Operon 1498597 . . . 1500179 note = "documented tehAB operon" |
| lux-z.pk019.o21 | − | Operon complement(3961980 . . . 3963245) note = "predicted operon" note = "ordered genes contained in the operon: rhlB" |
| lux-z.pk020.a23 | + | Operon 3572704 . . . 3573297 note = "predicted operon" note = "ordered genes contained in the operon: b3434" |
| lux-z.pk020.c16 | − | Operon complement(3809518 . . . 3810192) note = "predicted operon" note = "ordered genes contained in the operon: radC" |
| lux-z.pk020.c8 | + | Operon 4292060 . . . 4293373 note = "predicted operon" note = "ordered genes contained in the operon: gltP" |
| lux-z.pk020.e3 | + | Operon 167484 . . . 173444 note = "documented fhuACDB operon" |
| lux-z.pk020.h21 | + | Operon 4007918 . . . 4008433 note = "predicted operon" note = "ordered genes contained in the operon: yigL" |
| lux-z.pk020.j20 | − | Operon complement(379293 . . . 380511) note = "predicted operon" note = "ordered genes contained in the operon: b0358 b0359" |
| lux-z.pk020.j9 | + | Operon 2322776 . . . 2324098 note = "predicted operon" note = "ordered genes contained in the operon: atoE" |
| lux-z.pk020.l21 | + | Operon 1329072 . . . 1331669 note = "predicted operon" note = "ordered genes contained in the operon: topA" |
| lux-z.pk020.n12 | − | Operon complement(216179 . . . 218775) note = "predicted operon" note = "ordered genes contained in the operon: yaeF proS" |
| lux-z.pk021.a14 | + | Operon 4277559 . . . 4279208 note = "predicted operon" note = "ordered genes contained in the operon: yjcE" |
| lux-z.pk021.b3 | − | Operon complement(2962383 . . . 2964059) note = "documented lgt-thyA operon" |
| lux-z.pk021.c10 | + | Operon 3407917 . . . 3408882 note = "predicted operon" note = "ordered genes contained in the operon: yhdG" |
| lux-z.pk021.d1 | + | Operon 1687876 . . . 1689384 note = "predicted operon" note = "ordered genes contained in the operon: b1614" |
| lux-z.pk021.d22 | − | Operon complement(4523674 . . . 4525548) note = "predicted operon" note = "ordered genes contained in the operon: yjhJ |

TABLE 19-continued

| | | |
|---|---|---|
| | | yjhK yjhL" |
| lux-z.pk021.e10 | − | Operon complement(2287085 . . . 2288101) note = "predicted operon" note = "ordered genes contained in the operon: yi52_8" |
| lux-z.pk021.g16 | − | Operon complement(2421756 . . . 2423936) note = "predicted operon" note = "ordered genes contained in the operon: hisP hisM hisQ" |
| lux-z.pk021.h14 | − | Operon complement(3096577 . . . 3097584) note = "predicted operon" note = "ordered genes contained in the operon: yggM" |
| lux-z.pk021.h3 | + | Operon 1805820 . . . 1806680 note = "predicted operon" note = "ordered genes contained in the operon: b1725" |
| lux-z.pk021.i24 | + | Operon 3814303 . . . 3815166 note = "predicted operon" note = "ordered genes contained in the operon: yicC" |
| lux-z.pk021.k6 | − | Operon complement(4375389 . . . 4376522) note = "predicted operon" note = "ordered genes contained in the operon: ampC" |
| lux-z.pk021.l19 | − | Operon complement(2660603 . . . 2661343) note = "predicted operon" note = "ordered genes contained in the operon: b2532" |
| lux-z.pk021.n20 | + | Operon 3225442 . . . 3228880 note = "predicted operon" note = "ordered genes contained in the operon: ygjJ ygjK" |
| lux-z.pk021.n20 | + | Operon 3225442 . . . 3228880 note = "predicted operon" note = "ordered genes contained in the operon: ygjJ ygjK" |
| lux-z.pk021.o16 | − | Operon complement(2710047 . . . 2710904) note = "predicted operon" note = "ordered genes contained in the operon: yfiC" |
| lux-z.pk021.o4 | + | Operon 3490205 . . . 3491386 note = "predicted operon" note = "ordered genes contained in the operon: yhfC" |
| lux-z.pk021.p19 | + | Operon 4199504 . . . 4200901 note = "documented hydH operon" |
| lux-z.pk022.b12 | − | Operon complement(635939 . . . 636841) note = "predicted operon" note = "ordered genes contained in the operon: b0603" |
| lux-z.pk022.b20 | − | Operon complement(156299 . . . 156883) note = "predicted operon" note = "ordered genes contained in the operon: yadN" |
| lux-z.pk022.c5 | − | Operon complement(2432102 . . . 2432761) note = "predicted operon" note = "ordered genes contained in the operon: dedA" |
| lux-z.pk022.f12 | + | Operon 2264265 . . . 2265731 note = "predicted operon" note = "ordered genes contained in the operon: yeiQ" |
| lux-z.pk022.g13 | − | Operon complement(2221958 . . . 2222899) note = "predicted operon" note = "ordered genes contained in the operon: pbpG" |
| lux-z.pk022.g8 | − | Operon complement(3960360 . . . 3961844) note = "predicted operon" note = "ordered genes contained in the operon: gppA" |
| lux-z.pk022.h21 | + | Operon 2163690 . . . 2165051 note = "predicted operon" note = "ordered genes contained in the operon: b2081" |
| lux-z.pk022.i1 | − | Operon complement(2940940 . . . 2941170) note = "predicted operon" note = "ordered genes contained in the operon: b2809" |
| lux-z.pk022.j21 | + | Operon 2597860 . . . 2598968 note= "predicted operon" note = "ordered genes contained in the operon: gcvR bcp" |
| lux-z.pk022.k8 | − | Operon complement(4486129 . . . 4487631) note = "predicted operon" note = "ordered genes contained in the operon: yjgR" |
| lux-z.pk022.n7 | + | Operon 4002473 . . . 4003342 note = "predicted operon" note = "ordered genes contained in the operon: pldA" |
| lux-z.pk022.p18 | + | Operon 1277180 . . . 1278571 note = "documented narK operon" |
| lux-z.pk023.a11 | − | Operon complement(4282992 . . . 4284950) note = "predicted operon" note = "ordered genes contained in the operon: acs" |
| lux-z.pk023.c18 | + | Operon 1194346 . . . 1195596 note = "documented icdA operon" |
| lux-z.pk023.c21 | + | Operon 3387155 . . . 3388084 note = "predicted operon" note = "ordered genes contained in the operon: b3243" |
| lux-z.pk023.e17 | + | Operon 3418958 . . . 3420830 note = "predicted operon" note = "ordered genes contained in the operon: yhdY yhdZ" |
| lux-z.pk023.f12 | + | Operon 855186 . . . 856778 note = "predicted operon" note = "ordered genes contained in the operon: b0820" |
| lux-z.pk023.g8 | − | Operon complement(2957082 . . . 2962199) note = "predicted operon" note = "ordered genes contained in the operon: recC ppdC ygdB ppdB ppdA" |
| lux-z.pk023.j2 | − | Operon complement(3436342 . . . 3437146) note = "predicted operon" note = "ordered genes contained in the operon: yhdM yhdN" |
| lux-z.pk023.k11 | − | Operon complement(3239467 . . . 3242381) note = "documented uxaCA operon" |
| lux-z.pk023.k5 | − | Operon complement(1690914 . . . 1694095) note = "predicted operon" note = "ordered genes contained in the operon: uidB uidA" |
| lux-z.pk023.l18 | − | Operon complement(1928481 . . . 1928771) note = "predicted operon" note = "ordered genes contained in the operon: yebG" |
| lux-z.pk023.m21 | + | Operon 3963846 . . . 3965291 note = "predicted operon" note = "ordered genes contained in the operon: rhoL rho" |
| lux-z.pk023.m22 | + | Operon 1426547 . . . 1427008 note = "predicted operon" note = "ordered genes contained in the operon: b1371" |
| lux-z.pk023.m22 | − | Operon complement(3127058 . . . 3128230) note = "predicted |

TABLE 19-continued

| | | |
|---|---|---|
| | | operon" note = "ordered genes contained in the operon: b2981" |
| lux-z.pk023.o7 | + | Operon 4380191 . . . 4381198 note = "predicted operon" note = "ordered genes contained in the operon: yjeA" |
| lux-z.pk023.o8 | + | Operon 2263215 . . . 2264042 note = "predicted operon" note = "ordered genes contained in the operon: yeiP" |
| lux-z.pk025.b18 | − | Operon complement(1186342 . . . 1187472) note = "predicted operon" note = "ordered genes contained in the operon: ycfD" |
| lux-z.pk025.b8 | − | Operon complement(1349852 . . . 1355134) note = "predicted operon" note = "ordered genes contained in the operon: sapF sapD sapC sapB sapA" |
| lux-z.pk025.c11 | + | Operon 1146017 . . . 1146538 note = "predicted operon" note = "ordered genes contained in the operon: yceD" |
| lux-z.pk025.d13 | − | Operon complement(2549297 . . . 2550269) note = "predicted operon" note = "ordered genes contained in the operon: b2433 b2434" |
| lux-z.pk025.e10 | + | Operon 1391230 . . . 1392864 note = "predicted operon" note = "ordered genes contained in the operon: b1329" |
| lux-z.pk025.f5 | − | Operon complement(4487709 . . . 4488707) note = "predicted operon" note = "ordered genes contained in the operon: yjgS" |
| lux-z.pk025.h13 | − | Operon complement(1731778 . . . 1732125) note = "predicted operon" note = "ordered genes contained in the operon: ydhD" |
| lux-z.pk025.h22 | + | Operon 4098391 . . . 4099011 note = "documented sodA operon" |
| lux-z.pk025.i24 | − | Operon complement(1261249 . . . 1262723) note = "predicted operon" note = "ordered genes contained in the operon: ychB hemM" |
| lux-z.pk025.j11 | − | Operon complement(529356 . . . 530450) note = "predicted operon" note = "ordered genes contained in the operon: ybbB" |
| lux-z.pk025.j16 | + | Operon 1712401 . . . 1713006 note = "predicted operon" note = "ordered genes contained in the operon: gst" |
| lux-z.pk025.j4 | + | Operon 3578769 . . . 3579257 note = "predicted operon" note = "ordered genes contained in the operon: b3441" |
| lux-z.pk025.m6 | − | Operon complement(1581786 . . . 1581983) note = "predicted operon" note = "ordered genes contained in the operon: b1500" |
| lux-z.pk025.m7 | + | Operon 3775026 . . . 3776681 note = "documented lldP operon" |
| lux-z.pk025.o12 | + | Operon 3057773 . . . 3058666 note = "predicted operon" note = "ordered genes contained in the operon: iciA" |
| lux-z.pk025.o8 | + | Operon 402927 . . . 404042 note = "predicted operon" note = "ordered genes contained in the operon: yaiC" |
| lux-z.pk018.i18 | − | surA |
| lux-z.pk013.g19 | + | yacK |
| lux-z.pk014.h24 | − | map |
| lux-z.pk014.l8 | + | betT |
| lux-z.pk020.g15 | + | yaiB |
| lux-z.pk017.o4 | − | proC |
| lux-z.pk023.g7 | − | bioA |
| lux-t.pk001.a1 | | osmY |
| lux-t.pk001.a2 | | inaA |
| lux-t.pk001.a3 | | hisP1 |
| lux-a.pk068.c1 | | hisP3 |
| lux-t.pk001.a4 | | katG |
| lux-t.pk001.a5 | | yebF |
| lux-t.pk001.a6 | | flhB |
| lux-t.pk001.a7 | | ppa |
| lux-t.pk001.a8 | | sgcR(yjhJ) |
| lux-t.pk001.a9 | | flhC |
| lux-a.pk0022.d4 | | recA |

TABLE 20

| 1st gene of the operon | 45 minutes | 90 minutes | 135 minutes |
|---|---|---|---|
| b0116 (lpdA) | >2X | >2X | * |
| b0168 (map) | >2X | >2X | * |
| b0767 (ybhE) | >2X | >2X | >2X |
| b0842 | >2X | >2X | >2X |
| b1186 (nhaB) | >2X | >2X | >2X |
| b1413 (hrpA) | >2X | >2X | >2X |
| b1676 (pykF) | >2X | >2X | >2X |
| b1993 (cobU) | >2X | >2X | >2X |
| b2081 | >2X | >2X | * |
| b2999 | >2X | * | * |
| b3012 | >2X | >2X | >2X |
| b3904 (rhaB) | >2X | >2X | >2X |
| b4106 (phnC) | >2X | >2X | >2X |
| b4392 (slt) | >2X | >2X | * |
| b0314 (betT) | * | >2X | >2X |
| b0417 | * | >2X | >2X |
| b0422 (xseB) | * | >2X | * |
| b0572 | * | >2X | >2X |
| b0593 (entC) | * | >2X | >2X |
| b0839 (dacC) | * | >2X | >2X |
| b1188 (ycgB) | * | * | * |
| b1223 (narK) | * | >2X | >2X |

TABLE 20-continued

| 1st gene of the operon | 45 minutes | 90 minutes | 135 minutes |
|---|---|---|---|
| b1872 (bisZ) | * | >2X | >2X |
| b2237 (inaA) | * | >2X | >2X |
| b2322 | * | >2X | >2X |
| b2367 (emrY) | * | >2X | * |
| b2451 | * | >2X | >2X |
| b2550 | * | >2X | * |
| b2699 (recA) | * | >2X | >2X |
| b3245 | * | >2X | >2X |
| b3267 (yhdV) | * | >2X | >2X |
| b3336 (bfr) | * | >2X | * |
| b3365 (nirB) | * | >2X | >2X |
| b3419 (yhgJ) | * | >2X | >2X |
| b3666 (uhpT) | * | >2X | >2X |
| b3942 (katG) | * | >2X | >2X |
| b4043 (lexA) | * | >2X | * |
| b4264 (yjgS) | * | >2X | * |
| b0005 | * | * | >2X |
| b0123 (yacK) | * | * | >2X |
| b0386 (proC) | * | * | >2X |
| b0450 (glnK) | * | * | >2X |
| b0774 (bioA) | * | * | >2X |
| b1847 (yebF) | * | * | >2X |
| b1852 (zwf) | * | * | >2X |
| b2019 (hisG) | * | * | >2X |
| b2114 (metG) | * | * | >2X |
| b2428 | * | * | >2X |
| b3573 | * | * | >2X |
| b3779 (gppA) | * | * | >2X |
| b4226 (ppa) | * | * | >2X |

What is claimed is:

1. A method for determining gene function comprising:

(a) providing a microorganism comprising genomic DNA;

(b) assembling at least one first genome-wide scale, genome-registered collection from the genomic DNA of the microorganism of (a) comprising a collection of reporter gene fusions each fusion comprising a reporter gene operably linked to a genomic DNA fragment, and assembling at least one second genome-wide scale, genome-registered collection from the genomic DNA of the microorganism of (a) which is not a collection of reporter gene fusions;

(c) perturbing each collection from (b) with at least one perturbation;

(d) measuring the response of each collection to each perturbation of (c); and (e) analyzing the results of the at least one perturbation to identify patterns of similarities and differences between the at least two genome-registered collections resulting in the determination of gene function.

2. A method according to claim 1 wherein the perturbation is the result the presence of chemicals.

3. A method according to claim 1 wherein the microorganism is selected from the group consisting of prokaryotes and fungi.

4. A method according to claim 3 wherein the prokaryote is an enteric bacteria.

5. A method according to claim 4 wherein the enteric bacteria are selected from the group consisting of Escherichia and Salmonella.

6. A method according to claim 1 wherein the reporter gene is selected from the group consisting of luxCDABE, lacZ, gfp, cat, galK, inaZ, luc, luxAB, bgaB, nptII, phoA, uidA and xylE.

7. A method according to claim 1 wherein at least 50% of the sequences of the genomic DNA are known.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 1
ggatcggaat tcccggggat                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 2
ctggccgtta ataatgaatg                                                    20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 3
ggaattgggg atcggagctc ccggg                                              25

<210> SEQ ID NO 4
<211> LENGTH: 25
<212> TYPE: DNA
<213> ORGANISM: Artificial Sequence
```

```
<220> FEATURE:
<223> OTHER INFORMATION: Description of Artificial Sequence:  primer

<400> SEQUENCE: 4
gaatggcgcg aattcggtac ccggg                                        25
```